(12) United States Patent
Hirata et al.

(10) Patent No.: US 10,130,883 B2
(45) Date of Patent: Nov. 20, 2018

(54) INFORMATION PROCESSING DEVICE AND INFORMATION PROCESSING METHOD

(71) Applicant: Sony Interactive Entertainment Inc., Tokyo (JP)

(72) Inventors: Shinichi Hirata, Kanagawa (JP); Naoki Numaguchi, Tokyo (JP); Takeshi Yamagishi, Kanagawa (JP); Hiroshi Osawa, Kanagawa (JP); Keiji Togawa, Tokyo (JP)

(73) Assignee: Sony Interactive Entertainment Inc., Tokyo (JP)

( * ) Notice: Subject to any disclaimer, the term of this patent is extended or adjusted under 35 U.S.C. 154(b) by 56 days.

(21) Appl. No.: 15/110,876

(22) PCT Filed: Oct. 20, 2014

(86) PCT No.: PCT/JP2014/077873
§ 371 (c)(1),
(2) Date: Jul. 11, 2016

(87) PCT Pub. No.: WO2015/111261
PCT Pub. Date: Jul. 30, 2015

(65) Prior Publication Data
US 2016/0332075 A1    Nov. 17, 2016

(30) Foreign Application Priority Data

Jan. 21, 2014 (JP) ................ 2014-008895
Jan. 21, 2014 (JP) ................ 2014-008896
Jan. 21, 2014 (JP) ................ 2014-008897

(51) Int. Cl.
*A63F 13/22* (2014.01)
*A63F 13/428* (2014.01)
(Continued)

(52) U.S. Cl.
CPC ............ *A63F 13/428* (2014.09); *A61B 5/025* (2013.01); *A63F 13/211* (2014.09);
(Continued)

(58) Field of Classification Search
CPC ...... A63F 13/213; A63F 13/211; A63F 13/25; A63F 13/65; A63F 13/98; A63F 2300/105; A63F 2300/1087
(Continued)

(56) References Cited

U.S. PATENT DOCUMENTS 6,290,565 B1    9/2001   Galyean, III
7,099,747 B2    8/2006   Mikami
(Continued)

FOREIGN PATENT DOCUMENTS

JP    10302085 A    11/1998
JP    2005125460 A   5/2005
(Continued)

OTHER PUBLICATIONS

Extended Search Report for corresponding EP Application No. 14879435.7, 9 pages, dated Jul. 12, 2017.
(Continued)

*Primary Examiner* — David L Lewis
*Assistant Examiner* — Shauna-Kay Hall
(74) *Attorney, Agent, or Firm* — Matthew B. Dernier, Esq.

(57) ABSTRACT

An information processing device communicates with a block set assembled by a user, and thereby obtains information on the structure of the block set. In addition, a corresponding position setting screen including an image of an object corresponding to the block set is displayed on a display device. The user moves a joint of the block set which joint is desired to be associated, by for example bending and stretching the joint. Next, the user indicates a joint to be
(Continued)

associated on a 3D object side in the image of the 3D object by a cursor, and performs a determination input. The joint of the block set and the joint of the 3D object are thereby associated with each other. The block set and the object are interlocked with each other bidirectionally by thus setting the corresponding positions of the block set and the object.

9 Claims, 29 Drawing Sheets

(51) Int. Cl.
    *A63F 13/211* (2014.01)
    *A63F 13/24* (2014.01)
    *A63F 13/213* (2014.01)
    *A63F 13/235* (2014.01)
    *A61B 5/025* (2006.01)

(52) U.S. Cl.
    CPC ............ *A63F 13/213* (2014.09); *A63F 13/22* (2014.09); *A63F 13/235* (2014.09); *A63F 13/24* (2014.09); *A63F 2300/105* (2013.01); *A63F 2300/1087* (2013.01)

(58) Field of Classification Search
    USPC .......................................................... 463/36
    See application file for complete search history.

(56) References Cited

U.S. PATENT DOCUMENTS

| | | | |
|---|---|---|---|
| 8,055,021 | B2 | 11/2011 | Caritu |
| 9,229,528 | B2 | 1/2016 | Numagguchi |
| 9,498,721 | B2 | 11/2016 | Horovitz |
| 9,609,031 | B1 | 3/2017 | Allen |
| 2002/0196250 | A1* | 12/2002 | Anderson .......... G02B 27/2214 345/419 |
| 2005/0125099 | A1 | 6/2005 | Mikami |
| 2006/0136180 | A1* | 6/2006 | Hansen ................ G06F 17/50 703/1 |
| 2006/0258447 | A1* | 11/2006 | Baszucki ................ A63F 13/12 463/31 |
| 2007/0063997 | A1 | 3/2007 | Scherer |
| 2007/0116326 | A1 | 5/2007 | Aonuma |
| 2007/0262984 | A1 | 11/2007 | Pruss |
| 2009/0067678 | A1 | 3/2009 | Caritu |
| 2009/0197658 | A1* | 8/2009 | Polchin .................. A63F 13/02 463/9 |
| 2011/0021107 | A1* | 1/2011 | Nag ..................... A63H 33/042 446/91 |
| 2012/0280993 | A1* | 11/2012 | Jakobsen ............... G06T 15/40 345/420 |
| 2013/0217295 | A1 | 8/2013 | Karunaratne |
| 2013/0321447 | A1 | 12/2013 | Horovitz |
| 2014/0015813 | A1* | 1/2014 | Numaguchi ............ G06F 3/01 345/184 |

FOREIGN PATENT DOCUMENTS

| | | |
|---|---|---|
| JP | 2007004732 A | 1/2007 |
| JP | 2009526980 A | 7/2007 |
| JP | 2009266241 A | 11/2009 |
| WO | 2007050885 A2 | 5/2007 |
| WO | 2007093641 A2 | 8/2007 |
| WO | 2008139482 A2 | 11/2008 |
| WO | 2012160057 | 11/2012 |
| WO | 2013122798 A1 | 8/2013 |
| WO | 2014010004 A1 | 1/2014 |

OTHER PUBLICATIONS

Michael Philetus Weller, et al., "Posey: Instrucmenting a Poseable Hub and Strut Construction Toy," Proceedings of the Second International Conference on Tangible and Embedded Interaction (TEI'08), Bonn, Germany, 8 pages, (Feb. 18-20, 2008).

International Preliminary Report on Patentability for corresponding PCT Application No. PCT/JP2014/077873, 13 pages, dated Aug. 4, 2016.

International Search Report for corresponding PCT Application No. PCT/JP2014/077873, 4 pages, dated Jan. 6, 2015.

Posey: Instrumenting a Poseable Hub and Strut Construction Toy, Michael Philetus Weller, Ellen Yi-Luen Do, Mark D Gross, Proceedings of the Second International Conference on Tangible and Embedded Interaction, 8 pages,(Jan. 2008).

Wataru Yoshizaki et al., "Character Shisei Nyuryoku no Temeno Sohoko Interface", The A Robotics and Mechatronics Conference '12 Koen Ronbunshu, The Japan Society of Mechanical Engineers, 4 pages (May 27, 2012) (for relevancy see International Search Report for corresponding PCT Application No. PCT/JP2014/ 077873, 4 pages, dated Jan. 6, 2015).

Yuki Tayama et al., "Using a Human-Shaped Input Device for Remote Pose Instruction", IPSJ SIG Notes Group and Network Services (GN), 2014-GN-090 [online], 7 pages, Jan. 16, 2014 (for relevancy see International Search Report for corresponding PCT Application No. PCT/JP2014/077873, 4 pages, dated Jan. 6, 2015).

Office Action for corresponding CN Application No. 201580004639. X, 32 pages, dated Jun. 21, 2018.

Office Action for corresponding CN Application No. 201480073221. X, 21 pages, dated Jun. 20, 2018.

International Preliminary Report on Patentability for related PCT Application No. PCT/JP2015/050789, 11 pages, dated Aug. 4, 2016.

International Search Report for related PCT Application No. PCT/ JP2015/050789, 4 pages, dated Mar. 31, 2015.

European Search Report for related EP Application No. 15739885, 13 pages, dated Aug. 10, 2017.

Miller A et al: "Interactive 3D Model Acquisition and Tracking of Building Block Structures". IEEE Transactions on Visualization and Computer Graphics. IEEE Service Center, vol. 18. No. 4, pp. 651-659 (Apr. 1, 2012).

International Preliminary Report on Patentability for related PCT Application No. PCT/JP2015/050791, 11 pages, dated Aug. 4, 2016.

International Search Report for related PCT Application No. PCT/ JP2015/050791, 4 pages, dated Mar. 31, 2015.

Office Action for related U.S. Appl. No. 15/110,873, 19 pages, dated Oct. 6, 2017.

Office Action for related U.S. Appl. No. 15/110,887, 13 pages, dated Oct. 6, 2017.

* cited by examiner

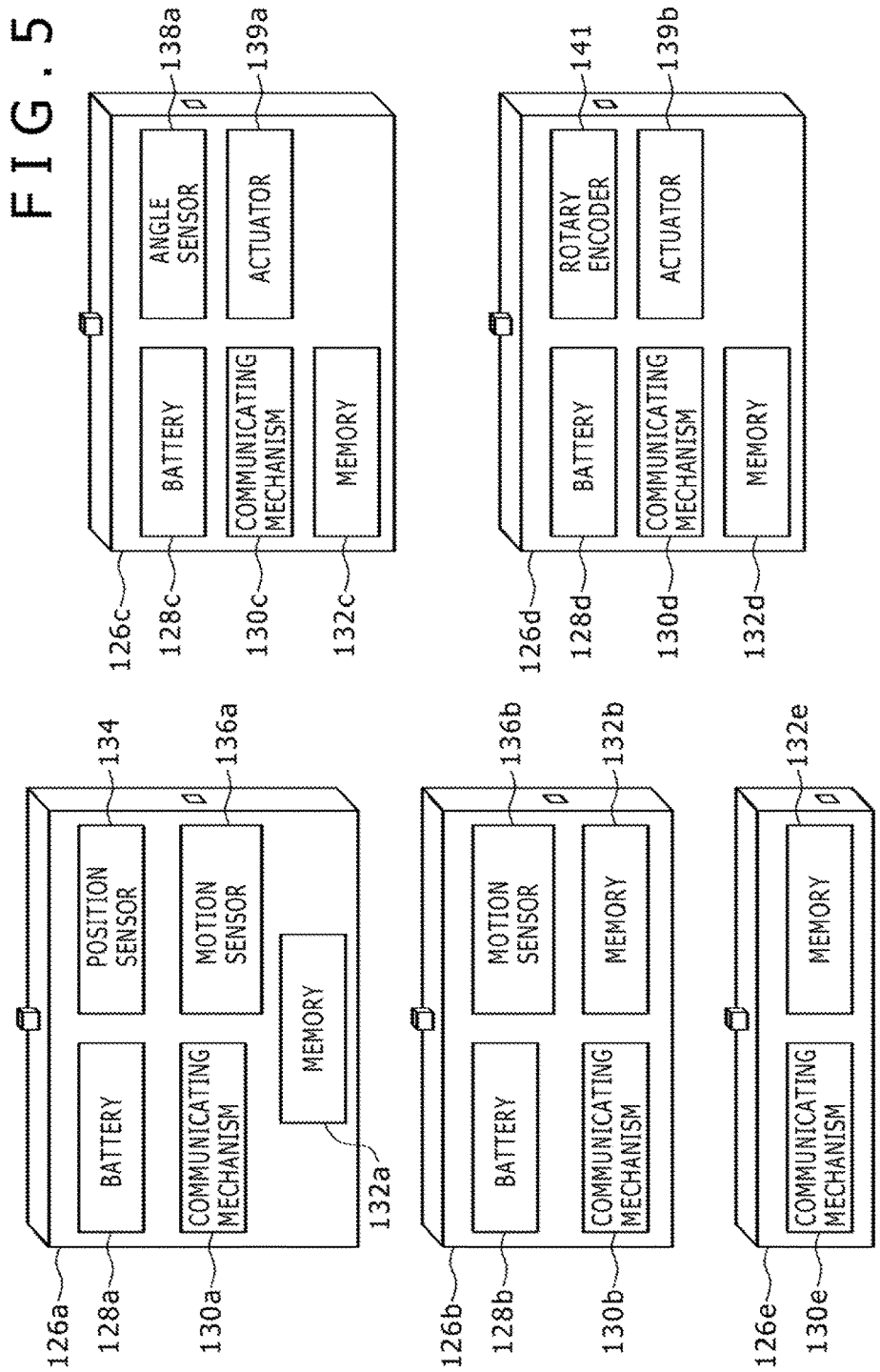

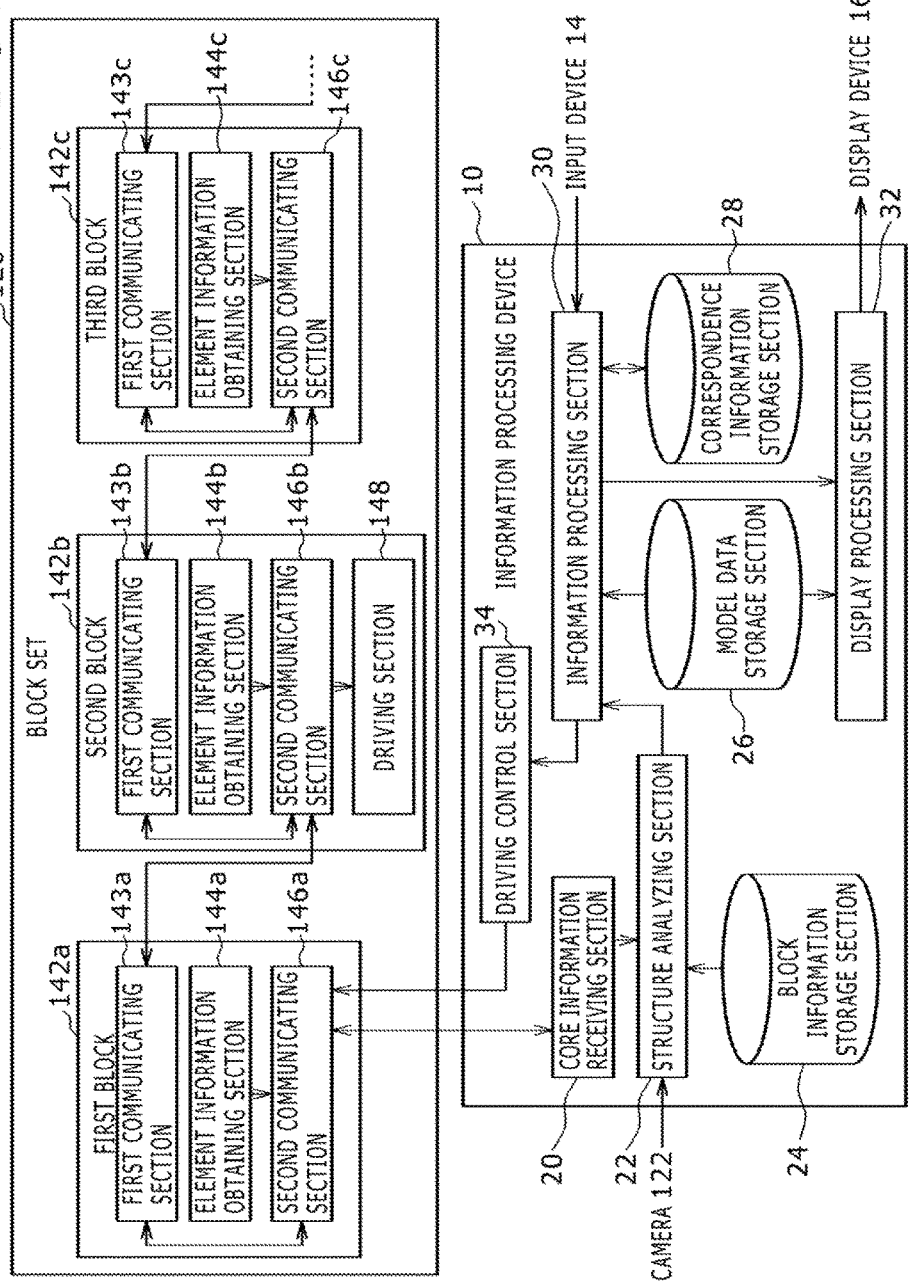

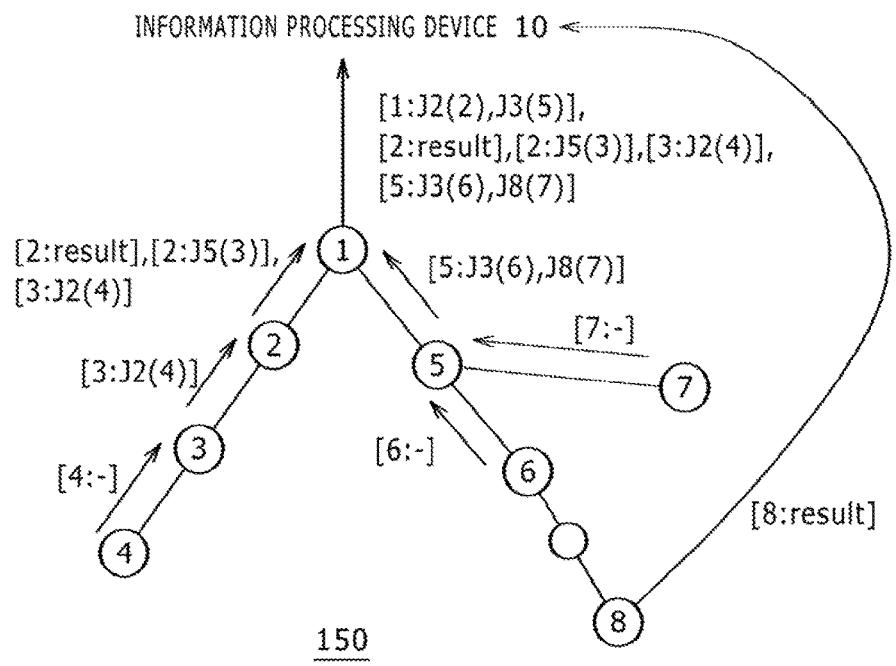

FIG.10

| IDENTIFICATION NUMBER (182) | SHAPE (184) | SIZE (186) | COLOR (188) |
|---|---|---|---|
| 1 | RECTANGULAR PARALLELEPIPED | 4×4×2 | BLUE |
| 2 | RECTANGULAR PARALLELEPIPED | 5×5×3 | YELLOW |
| 3 | CIRCULAR CYLINDER | 4×2 | GREEN |
| ... | ... | ... | ... |

180

| BLOCK SET | | 3D OBJECT | |
|---|---|---|---|
| JOINT | ANGLE CHANGE | JOINT | ANGLE CHANGE |
| RJ1 | $\theta/2$ | VJ3 | $\theta$ |
| RJ2 | $\theta/2$ | | |
| RJ3 | $\theta$ | VJ2 | $\theta/3$ |
| | | VJ1 | $2\theta/3$ |
| RJ4 | $\theta$ | VJ4 | $\theta$ |
| RJ5 | $\theta$ | VJ5 | $\theta + \psi$ |
| RJ6 | $\psi$ | | |
| RJ7 | $\theta$ | VJ6 | $\theta$ |
| | | VJ7 | $2\theta$ |
| | | JV8 | $\theta$ |
| ... | | ... | ... |

340

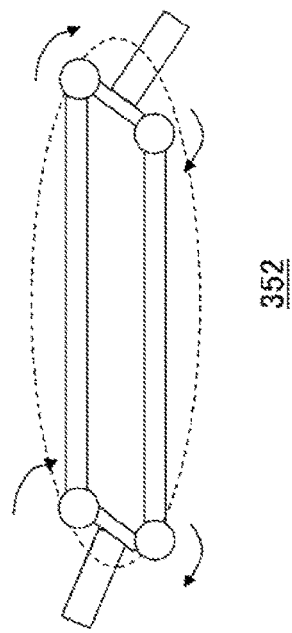
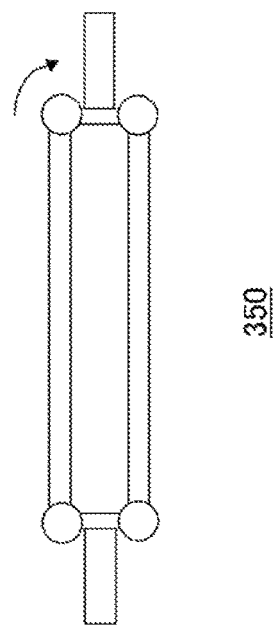
FIG. 31

INFORMATION PROCESSING DEVICE AND INFORMATION PROCESSING METHOD

TECHNICAL FIELD

The present invention relates to an information processing technology that uses an object in a real space.

BACKGROUND ART

Technologies that measure a parameter related to an object such as a human, a thing, or the like in a real space by some means, capture the parameter as an input value into a computer and analyze the input value, and display the input value as an image are used in various fields. In a field of computer games, intuitive and easy operation is realized by obtaining the movement of a user himself/herself or a marker held by the user and accordingly moving a character in a virtual world within a display screen (see PTL 1, for example). A technology that thus reflects movement or a change in shape of an object in a real space in screen display is expected to be applied to not only games but also toys, learning materials, and the like (see NPL 1, for example).

CITATION LIST

Patent Literature

[PTL 1] WO 2007/050885 A2

Non Patent Literature

[NPL 1] Posey: Instrumenting a Poseable Hub and Strut Construction Toy, Michael Philetus Weller, Ellen Yi-Luen Do, Mark D Gross, Proceedings of the Second International Conference on Tangible and Embedded Interaction, 2008, pp. 39-46

SUMMARY

Technical Problems

In order to produce a sense of realism and enable intuitive operation in a mode in which information processing is made to progress by using another object than an information processing layer that performs main operation, as described above, it is important to provide perceived affordance. A device that has a shape close to that of a real thing, such for example as the shape of a steering wheel of a car, the shape of a pistol, or the like and which can perform similar operation may be provided, but is limited in terms of uses. The range of the uses is widened when the shape of the device is made variable. However, a contrivance for measuring a change in shape or movement accordingly becomes necessary.

In a technology disclosed in NPL 1, for example, infrared LEDs and photosensors receiving light of the infrared LEDs are included in coupling portions of parts to measure angles of rotation of the parts and identify the shape of the parts. In this case, measurable angles of rotation are limited, and therefore the variable range of the shape is also limited. In addition, all parts need to include the elements, so that manufacturing cost is increased. Thus, the more flexible the form of the device, the more complex a mechanism for measuring the form of the device. As a result, manufacturing cost and processing cost tend to be increased.

The present invention has been made in view of such problems. It is an object of the present invention to realize various and advanced expressions by using a device that can be formed freely.

Solution to Problems

A mode of the present invention relates to an information processing device. The information processing device includes a structural information obtaining section obtaining information related to a position of a movable part in an overall structure of an external object. The information processing device further includes an information processing section displaying, on a display device, a setting screen for receiving a setting input related to an interlocking rule for the movable part from a user in order to interlock the object with an object model associated with the object, generating information related to the interlocking rule on a basis of the received setting input, and storing the information related to the interlocking rule in a storage device.

Another mode of the present invention relates to an information processing device. The information processing device includes a structural information obtaining section obtaining information related to a position of a movable part in an overall structure of an external object. The information processing device further includes an information processing section displaying, on a display device, a corresponding position setting screen for receiving a setting input for associating the movable part of the object and a movable part of an object model associated with the object from a user in order to interlock the object and the object model with each other by reflecting a change in the movable part of one of the object and the object model in the associated movable part of the other of the object and the object model, generating correspondence information on a basis of the received setting input, and storing the correspondence information in a storage device.

Yet another mode of the present invention relates to an information processing method. The information processing method is performed by an information processing device. The information processing method includes a step of obtaining information related to a position of a movable part in an overall structure of an external object. The information processing method further includes a step of displaying, on a display device, a corresponding position setting screen for receiving a setting input for associating the movable part of the object and a movable part of an object model associated with the object from a user in order to interlock the object and the object model with each other by reflecting a change in the movable part of one of the object and the object model in the associated movable part of the other of the object and the object model. The information processing method further includes a step of generating correspondence information on a basis of the received setting input, and storing the correspondence information in a storage device.

Yet another mode of the present invention relates to an information processing device. The information processing device includes a structural information obtaining section obtaining information related to a position of a movable part in an overall structure of an external object. The information processing device further includes an information processing section displaying, on a display device, a movement correspondence setting screen for receiving, from a user, a setting input for setting a movement reflecting rule for the movable part of the object and a movable part of an object model associated with the object, the movable parts being associated with each other, in order to interlock the object and the object model with each other by reflecting a change in the movable part of one of the object and the object model in the associated movable part of the other of the object and the object model, generating correspondence information on a basis of the received setting input, and storing the correspondence information in a storage device.

Yet another mode of the present invention relates to an information processing method. The information processing method is performed by an information processing device. The information processing method includes a step of obtaining information related to a position of a movable part in an overall structure of an external object. The information processing method further includes a step of displaying, on a display device, a movement correspondence setting screen for receiving, from a user, a setting input for setting a movement reflecting rule for the movable part of the object and a movable part of an object model associated with the object, the movable parts being associated with each other, in order to interlock the object and the object model with each other by reflecting a change in the movable part of one of the object and the object model in the associated movable part of the other of the object and the object model. The information processing method further includes generating correspondence information on a basis of the received setting input, and storing the correspondence information in a storage device.

Yet another mode of the present invention relates to an information processing device. The information processing device includes a structural information obtaining section obtaining information related to a position of a movable part in an overall structure of an external object. The information processing device further includes an information processing section displaying, on a display device, a corresponding position setting screen for receiving a setting input for associating the movable part of the object with a movable part of an object model associated with the object from a user in order to interlock the object and the object model with each other by reflecting a change in the movable part of one of the object and the object model in the associated movable part of the other of the object and the object model, receiving a setting input for associating different numbers of movable parts with each other between the object and the object model, generating correspondence information on a basis of the received setting inputs, and storing the correspondence information in a storage device.

Yet another mode of the present invention relates to an information processing method. The information processing method is performed by an information processing device. The information processing method includes a step of obtaining information related to a position of a movable part in an overall structure of an external object. The information processing method further includes a step of displaying, on a display device, a corresponding position setting screen for receiving a setting input for associating the movable part of the object with a movable part of an object model associated with the object from a user in order to interlock the object and the object model with each other by reflecting a change in the movable part of one of the object and the object model in the associated movable part of the other of the object and the object model. The information processing method further includes a step of receiving a setting input for associating different numbers of movable parts with each other between the object and the object model. The information processing method further includes a step of generating correspondence information on a basis of the received setting inputs, and storing the correspondence information in a storage device.

It is to be noted that arbitrary combinations of the above constituent elements and modes obtained by converting expressions of the present invention between a method, a device, a system, a computer program, a recording medium on which the computer program is recorded, and the like are also effective as modes of the present invention.

Advantageous Effect of Invention

According to the present invention, it is possible to realize various and advanced expressions using a device that can be formed freely.

BRIEF DESCRIPTION OF DRAWINGS

FIG. 5 is a diagram schematically depicting an example of internal configurations of communicating blocks included in the block set in the present embodiment.

FIG. 6 is a diagram depicting in detail configurations of the block set and an information processing device in the present embodiment.

FIG. 7 is a diagram schematically depicting an example of an information transmission path and transmitted information in the block set in the present embodiment.

FIG. 8 is a diagram depicting an example of a structure of data of basic information on communicating blocks in the present embodiment.

FIG. 10 is a diagram depicting an example of a structure of data of basic information on non-communicating blocks in the present embodiment.

FIG. 31 is a diagram of assistance in explaining a case where settings related to wheels of a block set are extended to a composite link in the present embodiment.

DESCRIPTION OF EMBODIMENTS

In a present embodiment, a plurality of blocks are assembled or modified, and the shape, posture, and position of the blocks are used as an input value for information processing. That is, such blocks can be regarded as an input device for an information processing device. Further, there are cases where the shape, posture, and position of the assembled blocks are changed so as to reflect a result of processing performed by the information processing device. In this case, the blocks are regarded as an output device for the information processing device. Though the processing performed by the information processing device in this case is not particularly limited, a preferred mode thereof will be illustrated later. A unity of such blocks or an assembly of the blocks will hereinafter be referred to collectively as a "block set." In addition, as will be described later, the block set may include an object other than blocks in a general sense, such as a thing imitating a clothing ornament, a clay work, or the like, and the shape and material of the object are not limited. Blocks, including these objects, will hereinafter be referred to as "blocks."

Figure 1:
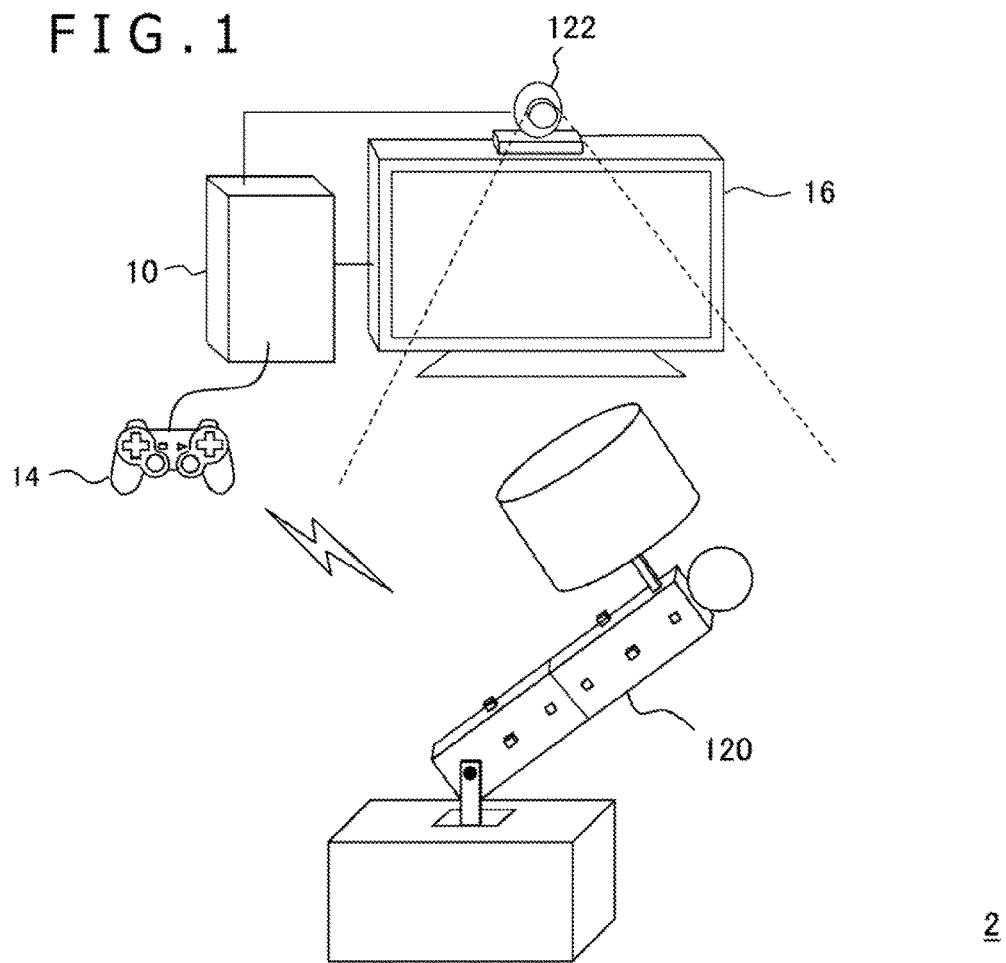
FIG. 1 is a diagram depicting an example of configuration of an information processing system to which a present embodiment can be applied.

FIG. 1 depicts an example of configuration of an information processing system to which the present embodiment can be applied. An information processing system 2 includes a block set 120, a camera 122 imaging the block set 120, an information processing device 10 that performs predetermined information processing with the block set 120 as an input device or an output device, an input device 14 that receives a user operation on the information processing device 10, and a display device 16 that displays data output by the information processing device as an image.

The information processing device 10 may be for example a game device or a personal computer, and may implement an information processing function by loading a necessary application program. The display device 16 may be an ordinary display such as a liquid crystal display, a plasma display, an organic EL display, or the like. The display device 16 may also be a television set including one of these displays and a speaker. The input device 14 may be one of ordinary input devices such as a game controller, a keyboard, a mouse, a joystick, a touch pad disposed on a screen of a display device 12, and the like, or any combination thereof.

The connection of the information processing device 10 to the camera 122, the input device 14, and the display device 16 may be made whether by wire or by radio, and may be made via various networks. Alternatively, two or more or all of the camera 122, the information processing device 10, the input device 14, and the display device 16 may be combined and provided integrally. In addition, the camera 122 does not necessarily need to be mounted on the display device 16. There may be a plurality of block sets 120 depending on contents processed by the information processing device 10. The block set 120 and the information processing device 10 establish a wireless connection using a Bluetooth (registered trademark) protocol, an IEEE 802.11 protocol, or the like. Alternatively, one block of the block set 120 and the information processing device 10 may be connected to each other via a cable.

As described above, the block set 120 according to the present embodiment may be used as an input device for the information processing device 10, or may be used as an output device for the information processing device 10. Specifically, in the former case, the information processing device 10 performs information processing using a result of a user changing the position, posture, or shape of the block set 120 as an input value, and displays a result of the processing as an image on the display device 16. In the latter case, the information processing device 10 performs information processing according to an operation of the input device 14 by the user, and moves the block set 120 itself as a result of the information processing. The present embodiment may be configured to be able to implement both of the modes, or may be configured to be able to implement only one of the modes.

Figure 2:
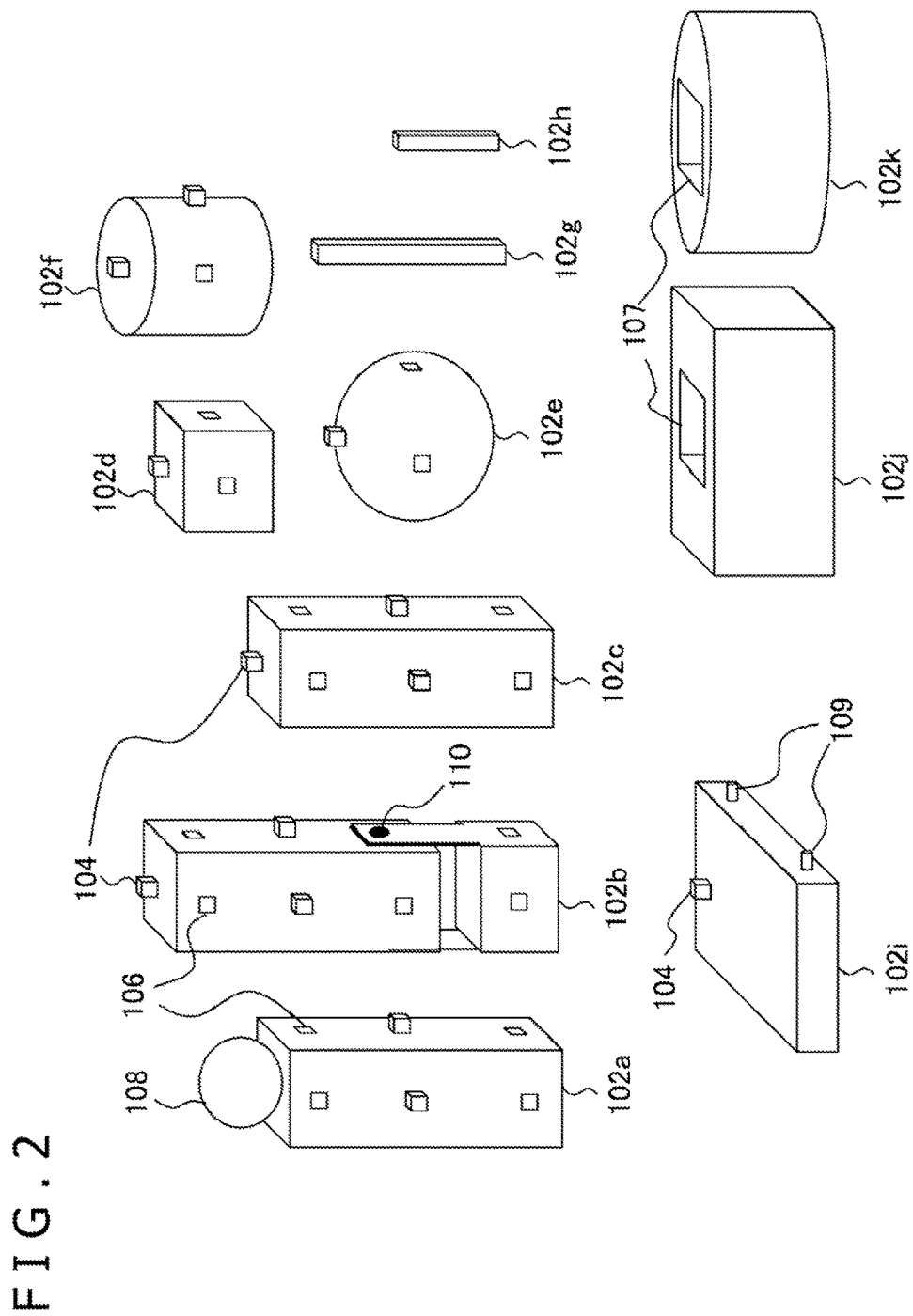
FIG. 2 is a diagram depicting an example of an external appearance of a block set in the present embodiment.

FIG. 2 depicts an example of external appearances of individual blocks constituting a block set. In the present embodiment, blocks are roughly classified into two kinds. One is a block configured to be able to communicate with another block or the information processing device 10. The other is a block without communicating means. Hereinafter, the former will be referred to as a "communicating block,"

and the latter will be referred to as a "non-communicating block." A communicating block may include various kinds of sensors that measure physical quantities such as the orientation, angle, position, and the like of the block in addition to a mechanism for communicating with another block.

Irrespective of whether blocks are communicating blocks or non-communicating blocks, as depicted in the figure, blocks can have various shapes, such as those of quadrangular prism blocks 102a, 102b, and 102c, a cube block 102d, circular cylinder blocks 102f and 102k, a sphere block 102e, a plate-shaped block 102i, a rectangular parallelepiped block 102j, and the like. Each block is provided with a projecting portion 104 and a recessed portion 106 having a predetermined size and shape. Blocks can be coupled to each other at desired positions by inserting a projecting portion 104 into a recessed portion 106. Alternatively, as with the rectangular parallelepiped block 102j, the circular cylinder block 102k, or the like, a block may be provided with a recessed portion 107 having a shape into which another block itself can be fitted, and thereby able to include the other block.

The block set may further include joint blocks 102g and 102h having both ends that can be inserted into recessed portions 106 of different blocks in order to adjust an interval between the blocks coupled to each other. In addition, a joint block may be capable of changing position and posture relation between blocks connected to each other by rotation or the like.

Projecting portions 104 and recessed portions 106 of communicating blocks also have a role of a terminal that enables signal transmission between blocks. For this purpose, ends of the respective portions are provided with a connector having a structure complying with the standard of a bus or the like provided within the blocks. Signal transmission and physical coupling between the blocks can be achieved at the same time by employing various kinds of connectors in general use or providing a dedicated special connector. Incidentally, when a path of signal transmission can be prepared separately, and coupling positions can be identified separately, means for connecting the blocks to each other is not limited to coupling between a projecting portion 104 and a recessed portion 106, but may be realized by a hook-and-loop fastener, a magnet, an adhesive tape, an adhesive, or the like. The path of signal transmission which path is prepared separately may be a mechanism of radio communication.

In addition, a certain block (quadrangular prism block 102b in the case of FIG. 2) of the communicating blocks may include two blocks, a bending and stretching shaft 110 that enables the two blocks to be bent and stretched, and a potentiometer that detects an angle formed between the blocks. Incidentally, in addition to the form in which both ends of the bending and stretching shaft 110 penetrating one block are joined with projections of the other block as depicted in the figure, a bending and stretching mechanism may be in a form in which two blocks are coupled to each other by a hinge, a metal capable of being bent and stretched, or the like, or may be a mechanism having a plurality of degrees of freedom which mechanism is similar to a joint in a ball-jointed doll, or the like, and is not particularly limited. The angle between the blocks may be made changeable continuously, or may be made changeable in a plurality of steps. In addition, the orientation of the shaft is not limited to that depicted in the figure.

The angle between the blocks as constituent elements is preferably maintained even after the user takes hands off the blocks. Incidentally, the angle between the blocks may be measured by an angle sensor other than a potentiometer. For example, when a block includes therewithin a sensor measuring a relative angle to another block, the blocks do not necessarily need to be connected to each other. In addition, as will be described later, one block may be configured to be capable of being bent and stretched or capable of being rotated, and the bending and stretching angles or angle of rotation of the block may be measured.

Hereinafter, a mechanism for thus making the angle variable may be referred to as a "joint," and two blocks whose relative angle changes according to the movement of the joint may be referred to as "links." Further, the joint angle of a communicating block thus having a joint may be made controllable according to a request from the information processing device 10. In this case, the communicating block is provided with an actuator for controlling the joint angle, such as a servomotor or the like.

In addition, a certain block (plate-shaped block 102i in the case of FIG. 2) of the communicating blocks may have rotatable shafts 109 that project from a side surface. Wheels mounted on the plurality of shafts 109 enable the block to be moved as in the case of a vehicle. The movement may be realized by the user by pushing the block, or may be realized according to a request from the information processing device 10. In the latter case, the communicating block is provided with an actuator such as a motor or the like for rotating the shafts. In a case where the shafts 109 are axles, a mechanism such as a rack and pinion or the like for changing the orientation of the wheels may be provided, and this mechanism is also made controllable by an actuator according to a request from the information processing device 10.

In addition, a certain block of the communicating blocks includes therewithin one or a combination of a plurality of an acceleration sensor, a gyro sensor, a geomagnetic sensor, and the like and a motion sensing function such as a method of tracking an attitude using a camera and a marker attached to an object or the shape itself of the object, or the like. Blocks in which to include the sensors as well as kinds and combinations of the sensors to be included are determined according to information processing to be realized by using the block set. Alternatively, the blocks in which to include the sensors as well as kinds and combinations of the sensors to be included are selected by the user from various variations at a time of assembly.

Further, a certain block (quadrangular prism block 102a in the case of FIG. 2) of the communicating blocks may be provided with a marker 108. The marker 108 is used to identify a position in a three-dimensional space from the position and size of the marker 108 in an image photographed by the camera to be described later. Hence, the marker 108 is formed so as to have a size, shape, and a color that can be detected from the photographed image by matching processing or the like. For example, the marker 108 may be a spherical body including an ordinary light emitting body such as a light emitting diode, an electric bulb, or the like within an optically transparent spherical resin, or the marker 108 may be a bar code, a two-dimensional code, or the like. When a plurality of blocks are provided with a marker 108, the markers 108 may be varied in color from one block to another.

The outer shells of communicating blocks and non-communicating blocks are typically formed of a synthetic resin. However, the materials of the outer shells of communicating blocks and non-communicating blocks are not limited, but may be a metal, a glass, or the like. Because non-communicating blocks, in particular, do not include a communicating mechanism or the like, the material, shape, and size of the non-communicating blocks can be determined freely. For example, the non-communicating blocks may be various kinds of parts such as clothes created using cloth, the head of a doll created using rubber, and the like, or may be additional things such as a weapon, an accessory, and the like. A non-communicating block may be made by the user himself/herself. A non-communicating block may be for example a solid body formed by whittling an eraser, a clay work, a piece of work made of paper, a piece of work made by folding paper, or the like. In addition, a non-communicating block may be for example a block having an LED that emits light of a predetermined color by being energized from a communicating block or a display device that displays an image.

The information processing device 10 according to the present embodiment identifies the state of blocks with high accuracy by complementarily using information on the skeletal shape, posture, and the like of the block set which information can be obtained by communication with a communicating block and information on an external shape photographed by the camera 122. Therefore the external appearance of the block set can be represented freely by using non-communicating blocks. For example, a block having a shape that includes a communicating block, such as the rectangular parallelepiped block 102j or the circular cylinder block 102k in FIG. 2, may be realized as a non-communicating block.

Figure 3:
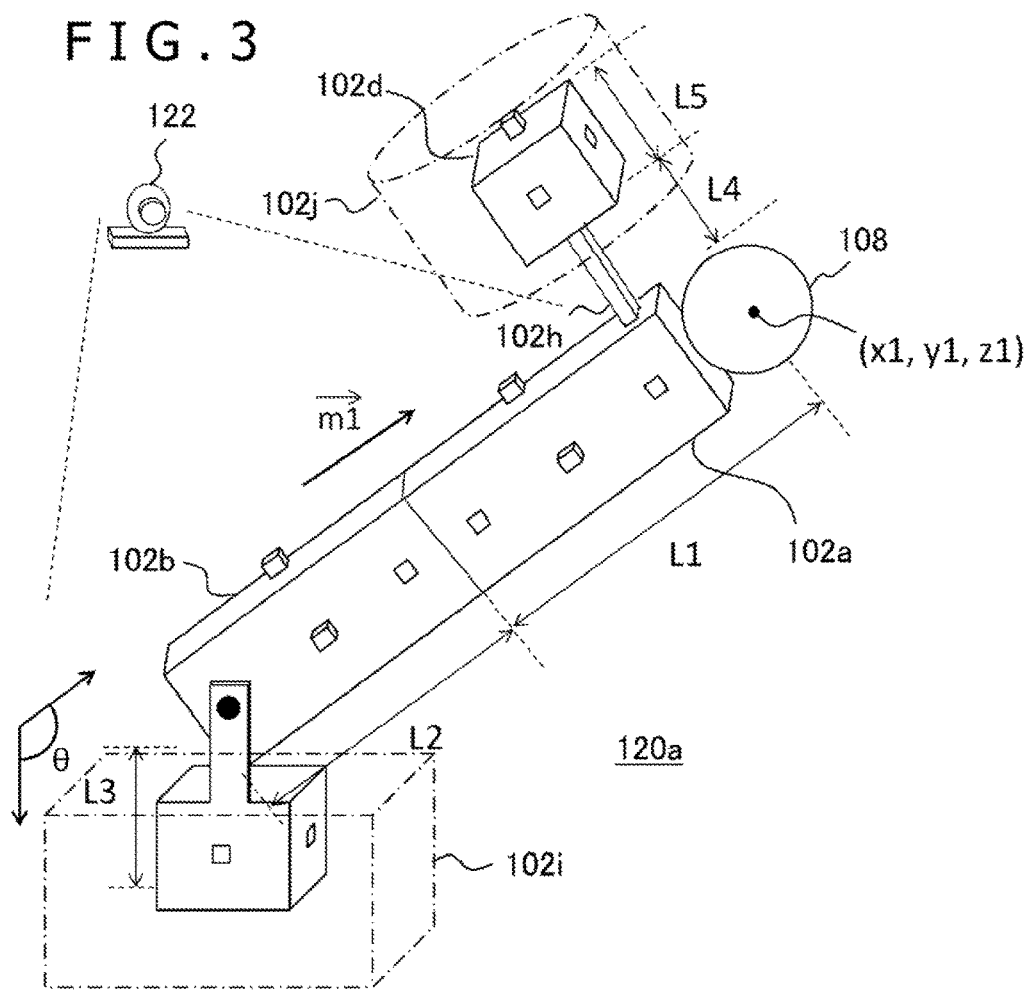
FIG. 3 is a diagram depicting only a structure of communicating blocks of the block set depicted in FIG. 1.

FIG. 3 depicts only the structure of communicating blocks of the block set 120 depicted in FIG. 1. Specifically, a block set 120a in the figure is formed by excluding the rectangular parallelepiped block 102j and the circular cylinder block 102k as non-communicating blocks from the block set 120 in FIG. 1, and is formed by the quadrangular prism blocks 102a and 102b, the cube block 102d, and joint block 102h depicted in FIG. 2. Of the blocks, the lower block of the quadrangular prism block 102b and the cube block 102d are contained by the rectangular parallelepiped block 102j and the circular cylinder block 102k, respectively, which are non-communicating blocks, in the block set 120 in FIG. 1. The lower block of the quadrangular prism block 102b and the cube block 102d are thus not seen from the outside. A structure constituted of such communicating blocks can also be regarded as constituting a skeleton of the whole of the block set 120. A part constituted of the communicating blocks of the assembled block set 120 will hereinafter be referred to as a "core."

The present embodiment efficiently calculates the posture and shape of the block set 120 by detecting necessary parameters by a motion sensor and a potentiometer included in the communicating blocks constituting the core. For example, in the case of the block set 120a in FIG. 3, the orientation of each block and in turn the shape and posture of a central axis of the block set 120 can be derived on the basis of (1) coupling positions of each block and kinds of blocks, (2) an inclination vector m1 of the quadrangular prism block 102a or 102b, (3) an angle θ between the two blocks constituting the quadrangular prism block 102b, and (4) lengths L1, L2, L3, L4, and L5 of the respective blocks.

Supposing that the above-described (1) and (4) are identified by signal transmission between the blocks, and that the above-described (3) can be measured by a potentiometer, it is necessary and sufficient to include a motion sensor in the quadrangular prism block 102a or 102b in order to measure the above-described (2). Alternatively, it suffices to select a block including a motion sensor as the quadrangular prism block 102a or 102b.

Further, the position coordinates of the block set in the three-dimensional space of a real world are identified by using an image photographed by the camera 122. Here, when the camera 122 is a stereo camera, it is possible to obtain the absolute position of the block set in a three-dimensional space formed by a depth direction with respect to the camera 122 and a field plane of the camera. A technology is widely known which obtains the position of an object in a three-dimensional space according to principles of triangulation by using a parallax in images photographed by a stereo camera from a left viewpoint and a right viewpoint different from each other. Depth or three-dimensional information obtaining means other than binocular stereopsis may be used in place of a stereo camera. For example, a viewpoint moving camera may be used, or the position of the block set may be identified by a method of time of flight (TOF) using an infrared irradiating mechanism and an infrared sensor detecting the reflected light. A touch panel may be provided on a top surface of a stand on which the block set 120 is placed, and a position at which the block set 120 is placed may be detected by the touch panel.

Alternatively, as depicted in the figure, when the quadrangular prism block 102a provided with the marker 108 is used, the position may be identified on the basis of a still image or a frame image of a moving image photographed by a monocular camera 122. When the marker 108 is a light emitting body having a color, a luminance, and a size that are known, as described above, an image of the marker can be easily detected from the photographed image. Then, the position coordinates (x1, y1, z1) of the marker in the three-dimensional space can be identified from the position and size of the image of the marker in the photographed image. In cases where other markers are employed, ordinary image recognizing technologies such as pattern matching, feature point extraction, and the like can be applied. In a case where the block set 120 is moved, and the moving block set 120 is photographed as a moving image, efficient detection can be performed by applying an existing tracking technology.

Figure 4:
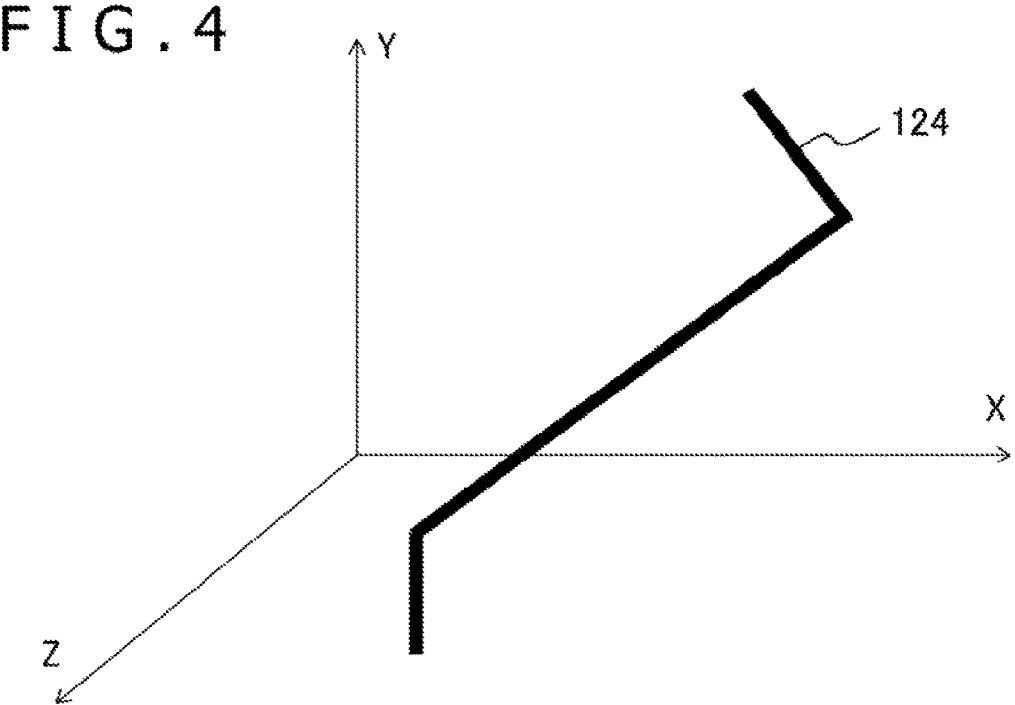
FIG. 4 is a diagram schematically depicting the central axis of a core which central axis is derived in the present embodiment.

Incidentally, the marker 108 may be a device that emits invisible light such as infrared rays or the like. In this case, a device that detects invisible light is introduced separately to detect the position of the marker 108. Similarly, a depth sensor, an ultrasonic sensor, a sound sensor, or the like may be used. Final position coordinates may be calculated by combining two or more of the absolute position detecting methods described above. FIG. 4 schematically depicts the thus derived central axis of the core. As depicted in the figure, the position, posture, and shape of a central axis 124 in the three-dimensional space are identified. The three-dimensional space may be the camera coordinate system of the camera 122, or may be a desired coordinate system into which the camera coordinate system of the camera 122 is converted. The position, posture, and shape of the core or the block set may hereinafter be referred to collectively as a "state."

FIG. 5 schematically depicts an example of internal configuration of communicating blocks. Blocks can be used properly according to uses by providing various variations as internal configurations of the blocks, as described above. In addition, when sensors assumed to be necessary to identify the state of the core are provided so as to be distributed in a plurality of blocks, excessive inclusion of sensors can be avoided, and thus manufacturing cost can be reduced.

In the example of FIG. 5, a block 126a includes a battery 128a, a communicating mechanism 130a, a memory 132a, a position sensor 134, and a motion sensor 136a. Suppose in this case that the communicating mechanism 130a includes not only a wire communicating mechanism that receives a signal from another block via a connecting terminal but also a mechanism that performs radio communication with the information processing device 10. The memory 132a retains the identification number of the block 126a. The identification number is associated with information such as the size of the block 126a, the position of a recessed portion or a projecting portion of the block 126a, and the like in the information processing device 10. The same identification number may be given to blocks of the same kind. Alternatively, the identification number may be set uniquely for each block so as to be usable for the routing of signal transmission within the assembled block set or the like.

The position sensor 134 is a sensor for obtaining the absolute position of the block 126a. The position sensor 134 also includes a marker for image recognition. In the case of a marker, however, the absolute position is detected by a combination of the marker and the camera 122 installed outside, as described above. The motion sensor 136a is one or a combination of two or more of an acceleration sensor, a gyro sensor, and a geomagnetic sensor, a method using a camera, or the like, as described above.

A block 126b includes a battery 128b, a communicating mechanism 130b, a memory 132b, and a motion sensor 136b. The mechanisms may be similar to the above-described mechanisms of the block 126a. However, the communicating mechanism 130b may be formed by only a wire communicating mechanism that receives a signal from another block. Such a block is used in combination with the block 126a that can communicate with the information processing device 10. The same is true for the communicating mechanisms of other blocks.

A block 126c includes a battery 128c, a communicating mechanism 130c, a memory 132c, an angle sensor 138, and an actuator 139a. The block 126c is a communicating block having a joint, such as the quadrangular prism block 102b in FIG. 2. The angle sensor 138 is a sensor such as a potentiometer or the like that detects a joint angle. The actuator 139a changes the joint angle according to a control signal from the information processing device 10. An ordinary technology corresponding to the kind of the actuator can be adopted for the driving of the actuator according to the control signal.

A block 126d includes a battery 128d, a communicating mechanism 130d, a memory 132d, a rotary encoder 141, and an actuator 139b. The block 126d is a communicating block having rotatable shafts projecting outside, such as the plate-shaped block 102i in FIG. 2. When the block 126d is fitted with wheels, the block 126d itself can be propelled manually or automatically. Alternatively, the shafts and the wheels may be provided integrally in advance.

The rotary encoder 141 is a sensor that detects an amount of rotation of a wheel. The actuator 139b is a motor or the like that rotates wheels according to a control signal from the information processing device 10. A block 126e includes a communicating mechanism 130e and a memory 132e. That is, the block 126e does not include a battery nor a sensor. Therefore the block 126e is used in combination with another block 126a or 126b including a battery.

Incidentally, the communicating blocks of FIG. 5 are a mere example, and various kinds of sensors and other mechanisms may be combined in any manner. For example, not only joints and axles but also mechanisms of changing a steering direction and displacing a part of a block may be provided as moving parts of the block set. These mechanisms may be moved by an actuator driven according to a control signal from the information processing device 10. In addition, an LED or a display device may be provided. A mechanism that energizes a connected non-communicating block may be provided. Further, in addition to the sensors depicted in the figure, any sensor in practical use may be included.

Communicating blocks having such various internal configurations are prepared in various shapes as depicted in FIG. 2. A plurality of blocks of a same kind may be prepared. Alternatively, all of blocks may have a uniform shape and a uniform size, or may have a uniform internal configuration. When the shape and the internal configuration are varied, and various kinds of blocks can be purchased individually, a desired block set can be assembled flexibly at a minimum cost according to a use of each individual user. A basic set of blocks that can be assembled may be provided first, and additional blocks may be purchased afterward.

FIG. 6 depicts in detail a configuration of the block set 120 and the information processing device 10. Elements to be described as functional blocks performing various processing in FIG. 6 can be configured by a central processing unit (CPU), a memory, or another LSI in terms of hardware, or implemented by a program loaded into a memory or the like in terms of software. In addition, as already described, the blocks of the block set 120 include communicating mechanisms, memories, various kinds of sensors, and actuators. Hence, it is to be understood by those skilled in the art that these functional blocks can be implemented in various forms by only hardware, only software, or a combination thereof, and are not limited to any one of the forms.

As described above, the block set 120 is formed by the user by selecting and assembling each block. FIG. 6 depicts functional blocks of the part of the core in the assembled block set. Communicating blocks constituting the core are set as a first block 142a, a second block 142b, a third block 142c, . . . , and the like. In order to prevent complication of information, among the communicating blocks forming the block set 120, basically only one block establishes communication with the information processing device 10. The first block 142a is accordingly given a role of a hub. Then, information is transmitted starting with a communicating block in remotest connection relation to the first block 142a, and information on the entire core is aggregated in the first block 142a.

Hereinafter, a block relatively close to the first block 142a in the connection of the blocks will be referred to as a "higher-level" block, and a block relatively remote from the first block 142a in the connection of the blocks will be referred to as a "lower-level" block. One block to be set as the first block 142a may be determined in advance. Alternatively, blocks having a mechanism of communicating with the information processing device 10 may be provided with a switch not depicted in the figure or the like, and a block whose switch is turned on by the user may be set as the first block 142a. Alternatively, a block that first establishes communication with the information processing device 10 in an assembly stage may be set as the first block 142a.

When the user couples another communicating block to the thus determined first block 142a, the block becomes a second block 142b. When yet another communicating block is coupled to the second block 142b, the block becomes a third block 142c. Incidentally, while the figure depicts only three communicating blocks, the number of communicating blocks constituting the core is not limited. The configuration and operation of one communicating block or four or more communicating blocks can be considered in a similar manner.

The first block 142a, the second block 142b, and the third block 142c include first communicating sections 143a, 143b, and 143c, element information obtaining sections 144a, 144b, and 144c, and second communicating sections 146a, 146b, and 146c, respectively. The second block 142b further includes a driving section 148. However, the driving section 148 may be provided in any of the other communicating blocks. The first communicating sections 143a, 143b, and 143c receives information transmitted from lower-level blocks directly connected to the first communicating sections 143a, 143b, and 143c. The information received in this case includes the identification numbers of blocks connected at lower levels than the corresponding blocks, the identification numbers of coupling positions, and results of measurement by built-in sensors. When a plurality of blocks are coupled to each other, information is superimposed with each passage through a block from a lowest-level block.

The element information obtaining sections 144a, 144b, and 144c include sensors built in the corresponding blocks and terminals provided at positions for connecting other blocks. The element information obtaining sections 144a, 144b, and 144c obtain information related to results of measurement by the sensors and the positions to which lower-level blocks are connected. The second communicating sections 146a, 146b, and 146c add information obtained by the element information obtaining sections 144a, 144b, and 144c of the corresponding blocks to the information received by the first communicating sections 143a, 143b, and 143c, the information received by the first communicating sections 143a, 143b, and 143c including the identification numbers of the lower-level blocks, the identification numbers of the coupling positions, and the results of measurement by the built-in sensors. The second communicating sections 146a, 146b, and 146c transmit resulting information as signals to the directly connected higher-level blocks. However, the second communicating section 146a of the first block 142a transmits the information to the information processing device 10. Further, the second communicating section 146a functions as an interface with the information processing device 10, for example by receiving processing starting and ending request signals, various kinds of signals necessary to establish communication, a control signal for driving an actuator of the block set, and the like from the information processing device 10.

When a control signal for driving an actuator is transmitted from the information processing device 10, the signal is sequentially transferred from the first block 142a to the lower-level blocks. Specifically, the first communicating sections 143a, 143b, and 143c of the respective blocks transmit the signal to the directly connected lower-level blocks. The second communicating sections 146b and 146c of the respective blocks receive the signal from the directly connected higher-level blocks. The driving section 148 of the second block 142b includes the actuator that changes a joint angle or rotates an axle. When the second block 142b is specified as an object to be driven in the control signal transmitted from the higher-level block, the driving section 148 moves the actuator by an amount corresponding to the control signal.

The information processing device 10 includes: a core information receiving section 20 that receives information related to the state of the core from the first block 142a of the block set 120; a structure analyzing section 22 that identifies the shape, posture, and position of the block set 120 on the basis of an image photographed by the camera 122 and the information related to the state of the core; an information processing section 30 that performs predetermined information processing according to the shape, posture, and position of the block set 120 or a user operation on the input device 14; a display processing section 32 that generates an image to be displayed as a result of the information processing, and outputs the image to the display device 16; and a driving control section 34 that transmits a signal for controlling the operation of the block set 120. The information processing device 10 further includes: a block information storage section 24 that stores information related to the individual blocks; a model data storage section 26 that stores the model data of a 3D object to be displayed on the display device 16; and a correspondence information storage section 28 that stores correspondence information between parts and movements of the block set and the 3D object.

The core information receiving section 20 receives the signal including the information related to the identification numbers of the communicating blocks constituting the core, the coupling positions of the communicating blocks, and the results of measurement by the built-in sensors, the information being aggregated by the first block 142a of the block set 120. The structure analyzing section 22 obtains, from the camera 122, the data of a moving image or a still image obtained by photographing the block set 120. Then, the information received by the core information receiving section 20 and the information obtained from the photographed image are integrated to identify the position, posture, and shape of the whole of the block set 120. The signal from the block set 120 and the image data from the camera 122 are input instantly. Thus, a temporal correspondence is assumed to be established between the signal from the block set 120 and the image data from the camera 122. However, synchronizing processing or the like may be performed depending on a necessary temporal resolution.

The structure analyzing section 22 identifies the shape and posture of the core of the block set 120 on the basis of the information from the core information receiving section 20. For example, information on L1 to L5 in FIG. 3 is derived on the basis of the identification numbers of the communicating blocks constituting the core. Further, coupling positions and an angle formed between blocks are identified from the identification numbers of the real coupling positions and the information of the angle sensor. Further, the vector m1 in FIG. 3 is derived from the information of the motion sensor. Information related to the position of the block set 120 in the three-dimensional space and the superficial shape of the block set 120 including the non-communicating blocks is identified on the basis of the photographed image transmitted from the camera 122, a depth image generated from the photographed image, or the like.

At this time, an image of a communicating block included in the core, such for example as the marker 108 in FIG. 3 or the like, is detected from the image. The marker 108 is set as a reference part, and the position of the marker 108 is derived from the depth image or the like. Then, positional relation between the core and the non-communicating blocks, and in turn the position, posture, and shape of the whole of the block set, can be identified from the structure of the core connected from the reference part, such as the central axis 124 in FIG. 4, and positional relation of an image of the non-communicating blocks to an image of the reference part. When this processing is performed at a predetermined frequency, the structure of even a block set in a process of being assembled by the user can be recognized in real time.

The block information storage section 24 stores basic information on the blocks used as the block set. In a case of a communicating block, the basic information is information associating an identification number given to the block in advance with information related to a shape, a size, and positions to which other blocks can be connected. In a case of a non-communicating block, the basic information is information associating an identification number given to the block in advance with external features such as a color, a pattern, a material, a texture, and the like. In the case of a non-communicating block, the more detailed such external features, the higher the accuracy of identifying the block. However, the information on the non-communicating blocks does not need to be stored when information processing performed by the information processing device 10 does not require identification of each non-communicating block.

The information processing section 30 performs processing to be performed according to the state of the block set 120 which state is identified by the structure analyzing section 22 or a user operation via the input device 14. For example, after the block set 120 is assembled, a 3D object representing the shape of the block set or a 3D object of a model associated with the block set is displayed. Then, the displayed 3D object is made to move according to the movement of the block set 120. Alternatively, a computer game is started, and made to progress according to user operations via the input device 14, and the block set 120 is moved according to the progress of the computer game.

For this purpose, the model data storage section 26 stores data necessary to render the object model displayed on the display device 16 by the information processing section 30. This object model may be designed in advance, such as a character appearing in a game or the like, or may be created by the user according to the assembled block set. The information processing section 30 further performs processing for associating parts of the block set and the object such as joints, wheels, and the like with each other, and further associating movements of the parts of both of the block set and the object with each other. At this time, the information processing section 30 may set all of correspondences, or may display a setting screen allowing the user to establish the associations and receive setting input. Alternatively, those may be combined with each other as appropriate. The correspondence information storage section 28 stores information related to the thus set correspondence relation of the parts and the movements.

Thus, even when the user creates the block set freely, not only the position but also the shape and posture of the block set can be interlocked with the object on the screen. For example, the world of a game can be reflected in the block set in the real world, or the movement of the block set can be reflected in a character in a virtual world. At this time, movements of both of the block set and the object do not necessarily need to be completely identical with each other, but various changes are allowed to be set by associating movements. In addition, the movement does not need to be reflected in real time. For example, when changes in the state of the block set moved by the user with the passage of time are stored, a mode can be realized in which the corresponding object reproduces the movements in arbitrary timing. In turn, movements of a character in a computer game or an animation can be created by simple operations.

In a mode in which the information processing device 10 moves the block set 120, the driving control section 34 transmits a control signal to the block set 120 according to a request from the information processing section 30. Specifically, the transmitted signal varies depending on a control system, and a technology commonly used in a field of robotics or the like may be adopted as appropriate. The transmitted control signal is received by the second communicating section 146a of the first block 142a in the block set 120, and is reflected in the operation of the driving section 148 in the target block (second block 142b in the case of FIG. 6) by signal transmission within the block set 120. Alternatively, the control signal may be directly transmitted to the target block by radio communication or the like.

The display processing section 32 creates image data as a result of processing performed by the information processing section 30, and displays the image data on the display device 16. In an example in which the object moving according to the movement of the block set 120 is displayed, the object is rendered so as to correspond to the movement of the block set 120 at an output frame rate of the display device 16, and is output as a video signal on the display device 16. An ordinary computer graphics technology can be applied to the rendering processing itself. The display processing section 32 further displays, on the display device 16, a screen for setting associations of parts and movements of the block set 120 and the object with each other. In a case where the information processing section 30 makes all of the associations, a screen for the user to check or correct the set correspondences may be displayed. In addition, the display processing section 32 displays an image corresponding to information processing being performed by the information processing section 30, such as a game screen or the like, as appropriate.

FIG. 7 schematically depicts an example of an information transmission path in the block set 120 and transmitted information. Each of circles within which a number is written in an information transmission path 150 represents a block. A straight line between circles represents a state in which the blocks are coupled to each other. In addition, the numbers within the circles are set as the identification numbers of the respective blocks. The block having an identification number "1" corresponds to the first block 142a in FIG. 6, and establishes communication with the information processing device 10. Further, the blocks having identification numbers "2" and "3" in FIG. 7 are connected in series with the block having the identification number 1, and can therefore be regarded as corresponding to the second block 142b and the third block 142c, respectively, in FIG. 6.

On the other hand, a plurality of blocks may be coupled to one block. In the example of FIG. 7, the block having the identification number "2" and the block having an identification number "5" are connected to the block having the identification number "1." As described above, the block having the identification number "3" and the block having an identification number "4" are connected in series with the block having the identification number "2" in this order. The block having an identification number "6" and the block having an identification number "7" are connected in parallel with each other to the block having the identification number "5." In the present example, a block having no identification number is further connected to the block having the identification number "6," and the block having an identification number "8" is connected to the block having no identification number. The block having no identification number in this case corresponds to a non-communicating block.

As described above, information is basically transmitted from a lower-level block to a higher-level block. FIG. 7 depicts the contents of the transmitted information together with arrows indicating transmission directions. The information transmitted from the block having the identification number "3" to the block having the identification number "2," for example, is expressed as [3:J2(4)]. This is a signal formed in a format "own identification number: the identification number of a connecting position provided to the block (the identification number of a block connected to the connecting position)," and indicates that the block having the identification number "4" is connected to the position having the identification number "J2" among the connecting positions of the identification number "3." However, the figure does not limit the format nor contents of the information.

Directions corresponding to higher levels of blocks can be determined by ranking or the like, which is performed by a block having a role of a hub by searching a network formed by coupling the blocks to each other. A networking technology in a device tree constituting an ordinary information processing system can be applied to such a procedure.

The block having the identification number "4" in FIG. 7 is at a lowest level in a connection series to which the block having the identification number "4" belongs. The block having the identification number "4" therefore transmits information to the block having the identification number "3" at the level immediately above. Supposing that no other block is connected to the block having the identification number "4," that a connecting position of the block having the identification number "4" is identified uniquely, and that the block having the identification number "4" does not include any sensor, the transmitted information is only the identification number "4" of the block itself, and therefore the transmitted contents are expressed as "[4:-]." "-" indicates that there is neither a sensor measurement result nor a connected block.

When the block having the identification number "3" has received the signal from the identification number "4," the block having the identification number "3" transmits, to the block having the identification number "2" at the level immediately above, a signal obtained by associating the number of a terminal that has received the signal from the identification number "4" or the like as the identification number of a connecting position with the identification number "4" and further associating the identification number "3" of the block itself with the identification number "4." The transmitted contents of this signal are [3:J2(4)], as described above. The block having the identification number "2" similarly generates a signal obtained by associating the own identification number with the identification number of a connecting position ("J5" in the example of the figure) and the identification number "3" of the connected block, that is, [2:J5(3)]. In addition, supposing that the block having the identification number "2" includes a sensor, the block having the identification number "2" also generates a signal obtained by associating a signal indicating a result of measurement of the sensor with the own identification number. In the example of the figure, the measurement result is expressed as a "result." In actuality, however, a concrete numerical value is substituted according to the type of the sensor.

The block having the identification number "2" transmits the thus generated data and the data transmitted from the lower-level block, that is, [3:J2(4)] to the block having the identification number "1" at the level immediately above. However, these signals do not always need to be transmitted simultaneously. When the contents of the signals once transmitted are changed, only information on the change may be transmitted, for example. Meanwhile, supposing that the blocks having the identification numbers "6" and "7" which blocks are connected to the block having the identification number "5" do not include a sensor, and that connecting positions of the blocks having the identification numbers "6" and "7" are identified uniquely, signals [6:-] and [7:-] are transmitted from these blocks, respectively, to the block having the identification number "5," as in the case of the block having the identification number "4." The block having the identification number "6" is connected with yet another block. However, the block is a non-communicating block, and therefore information is not obtained from the non-communicating block.

The block having the identification number "5" generates a signal obtained by associating the own identification number with the identification numbers of connecting positions and the identification numbers of the connected blocks, and transmits the signal to the block having the identification number "1" at the level immediately above. When a plurality of blocks are connected as depicted in the figure, these blocks are collectively indicated by [5:J3(6), J8(7)] or the like. Here, "J3" and "J8" are the identification numbers of the connecting positions to which the blocks having the identification numbers in the parentheses are connected.

The information on the core of the block set is thus aggregated in the block having the identification number "1." As with the other blocks, the block having the identification number "1" generates a signal obtained by associating the own identification number with the identification numbers of connecting positions and the identification numbers of the blocks connected to the connecting positions. Then, the block having the identification number "1" transmits the signal to the information processing device 10 together with the signals transmitted from the lower-level blocks. The information processing device 10 can therefore successively obtain the identification numbers of the blocks constituting the core, the connection relation of each block, and the measurement result in the block including the sensor.

When one block is thus set as a block having a role of a hub, and the information is thus aggregated and then transmitted to the information processing device 10, complication of the information and unnecessary communication processing can be prevented. On the other hand, in some cases, communication may be performed from a plurality of blocks to the information processing device 10. For example, in the example of FIG. 7, the block having an identification number "8" is coupled to the block having the identification number "6" via the non-communicating block.

In this case, the block having the identification number "8" may directly transmit own data to the information processing device 10. When the block in question includes a position sensor, for example, the own identification number of the block and a result of measurement by the position sensor are directly transmitted to the information processing device 10. The information processing device 10 can therefore grasp the presence of the block coupled farther than the block having the identification number "6," and further estimate the shape of the block in question and approximate connecting conditions of the block in question. The larger the number of sensors included in the block having the identification number "8," the higher the accuracy of the information. When blocks from which a plurality of pieces of position information can be obtained are combined with each other, the structure of a block in a blind spot from the camera 122 can also be identified accurately.

FIG. 8 depicts an example of a data structure of basic information of communicating blocks, the basic information being stored in the block information storage section 24 of the information processing device 10. A communicating block information table 160 includes an identification number field 162, a shape field 164, a size field 166, and a connecting position field 168. The identification number field 162 describes an identification number given in advance to a communicating block forming the block set. The shape field 164 describes a kind of shape of each communicating block, that is, a type of block as illustrated in FIG. 2, such as a "quadrangular prism," a "cube," or the like. The size field 166 describes the horizontal width, depth, and vertical length of each communicating block.

The connecting position field 168 describes connecting positions provided to each communicating block in association with the identification numbers of the connecting positions. In the example of FIG. 8, a connecting position is described in a format "the identification number of the connecting position (face number, an x-coordinate within the face, a y-coordinate within the face)." The face number is uniquely determined for each face of the block in advance. For example, the communicating block having the identification number "1" is a quadrangular prism block having a horizontal width of 4 cm, a depth of 4 cm, and a vertical length of 8 cm. The connecting position having an identification number "J1" is located at the position of coordinates (2, 2) in a first face. The connecting position having an identification number "J2" is located at the position of coordinates (1, 2) in a second face. However, the format of the notation is not particularly limited as long as these pieces of information are represented.

Figure 9:
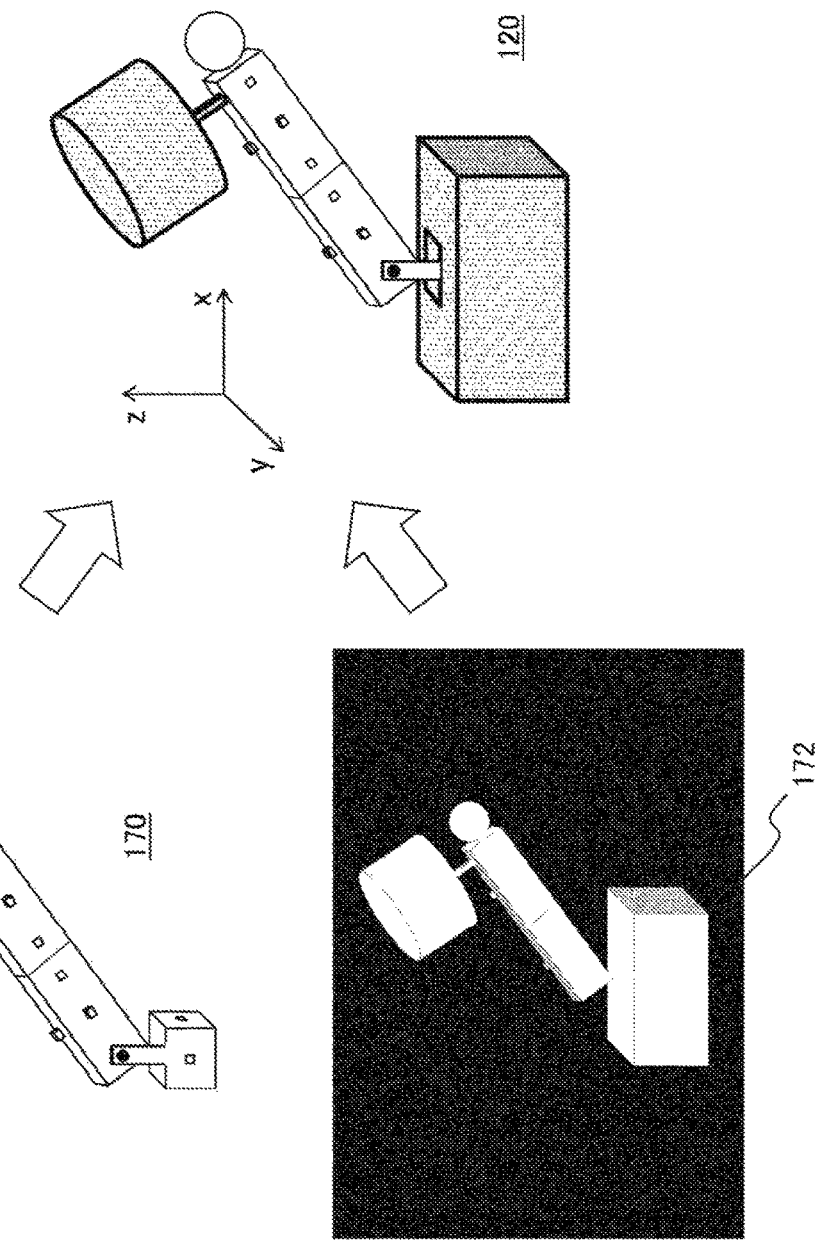
FIG. 9 is a diagram of assistance in explaining basic processing of identifying a state of the block set including non-communicating blocks in the present embodiment.

When the information processing device 10 retains such a communicating block information table 160, parameters as expressed in FIG. 3 are identified for the core on the basis of the signals transmitted from the block set 120. The structure analyzing section 22 identifies the position, posture, and shape of the whole of the block set 120 including the non-communicating blocks on the basis of the thus identified state of the core and the image photographed by the camera 122. FIG. 9 is a diagram of assistance in explaining basic processing for identifying the state of the block set including the non-communicating blocks. An upper left of the figure depicts the state of a core 170 which state is identified on the basis of the information received by the core information receiving section 20. Identified from this information are the connection relation of the communicating blocks and the shape of the core which shape is based on the connection relation of the communicating blocks. However, when a position sensor is internally provided, the position in the real space is also identified.

Meanwhile, the structure analyzing section 22 generates a depth image 172 from the image photographed by the camera 122. The depth image is an image showing an object within a field of view of the camera 122 with distances from the camera as pixel values. The depth image can be generated using a stereo camera or the like as the camera 122, as described above. The depth image 172 in the figure schematically represents an image in which the larger the distance, the lower the luminance. An image of the whole of the block set 120 is shown in the depth image 172 without distinction between the communicating blocks and the non-communicating blocks. When an image of at least a part of the blocks belonging to the core such for example as the marker or the like in the depth image is detected, the position coordinates of the part in the three-dimensional space, including the distance of the part from the camera, can be identified. Then, a camera coordinate system with respect to the core 170 is set such that the part detected in the image in the previously identified state of the core 170 is present at the position coordinates.

Incidentally, when the image of the core is detected, the color image photographed by the camera 122 may be used. Then, the state of the non-communicating blocks excluding the part of the core in the block set can be identified by obtaining a volume difference between the core 170 as viewed from the camera 122 side and the block set appearing as the image of the depth image 172. Shaded parts of the block set 120 depicted on the right of FIG. 9 are the non-communicating blocks obtained as the difference. As a result, as depicted in the figure, the position, posture, and shape of the whole of the block set 120 including the core and the non-communicating blocks can be identified. Incidentally, when an image of the block set 120 can be identified by background separation or the like, and the image and the core can be positioned on the basis of an apparent size of the core or the like, only the ordinary photographed image may be used without dependence on the depth image.

Incidentally, in the basic processing depicted in FIG. 9, the information obtained with regard to the non-communicating blocks is only two-dimensional information in the field plane of the camera. Accordingly, when basic information of the non-communicating blocks is stored in the block information storage section 24, and a search is made for blocks coinciding with apparent shapes and sizes in the field plane, accuracy of identifying three-dimensional shapes including the depth direction can be increased. FIG. 10 depicts an example of data structure of basic information of non-communicating blocks which information is stored in the block information storage section 24 of the information processing device 10.

A non-communicating block information table 180 includes an identification number field 182, a shape field 184, a size field 186, and a color field 188. The identification number field 182 describes an identification number given in advance to a non-communicating block forming the block set. Blocks whose shape, size, and color are the same may have a same identification number. The shape field 184 describes a kind of shape of each non-communicating block, that is, a type of block as illustrated in FIG. 2 such as a "rectangular parallelepiped," a "circular cylinder," or the like. The size field 186 describes the horizontal width, depth (or diameter), and vertical length of each non-communicating block. The color field 188 describes the color of each non-communicating block.

The information of the shape field 184, the size field 186, and the color field 188 may be information on a polygon, a texture, or the like, as in the case of data on an object model in 3D graphics. In addition, the information retained by the non-communicating block information table 180 is not limited to that depicted in the figure. For example, when the shape of a recessed portion or the like limits connectable communicating blocks, and the identification numbers of the connectable communicating blocks are retained, non-communicating blocks that may be connected to a communicating block belonging to the already identified core can be narrowed down on the basis of the communicating block. The structure analyzing section 22 refers to the non-communicating block information table 180, and identifies the non-communicating blocks coinciding individually with the images of the parts other than the core in the depth image 172 depicted in FIG. 9.

Incidentally, accurate shape of a block that is hidden by another block and thus unable to be seen is identified in a time evolving manner by tracking the movement of the block set after assuming that the block is not present in an initial state. When a part is hidden, and the shape of the part cannot be determined even when reference is made to the non-communicating block information table 180, some candidate shape is assumed or some face is assumed for only the hidden part, and correction is made gradually at later times to increase accuracy of shape recognition.

Figure 11:
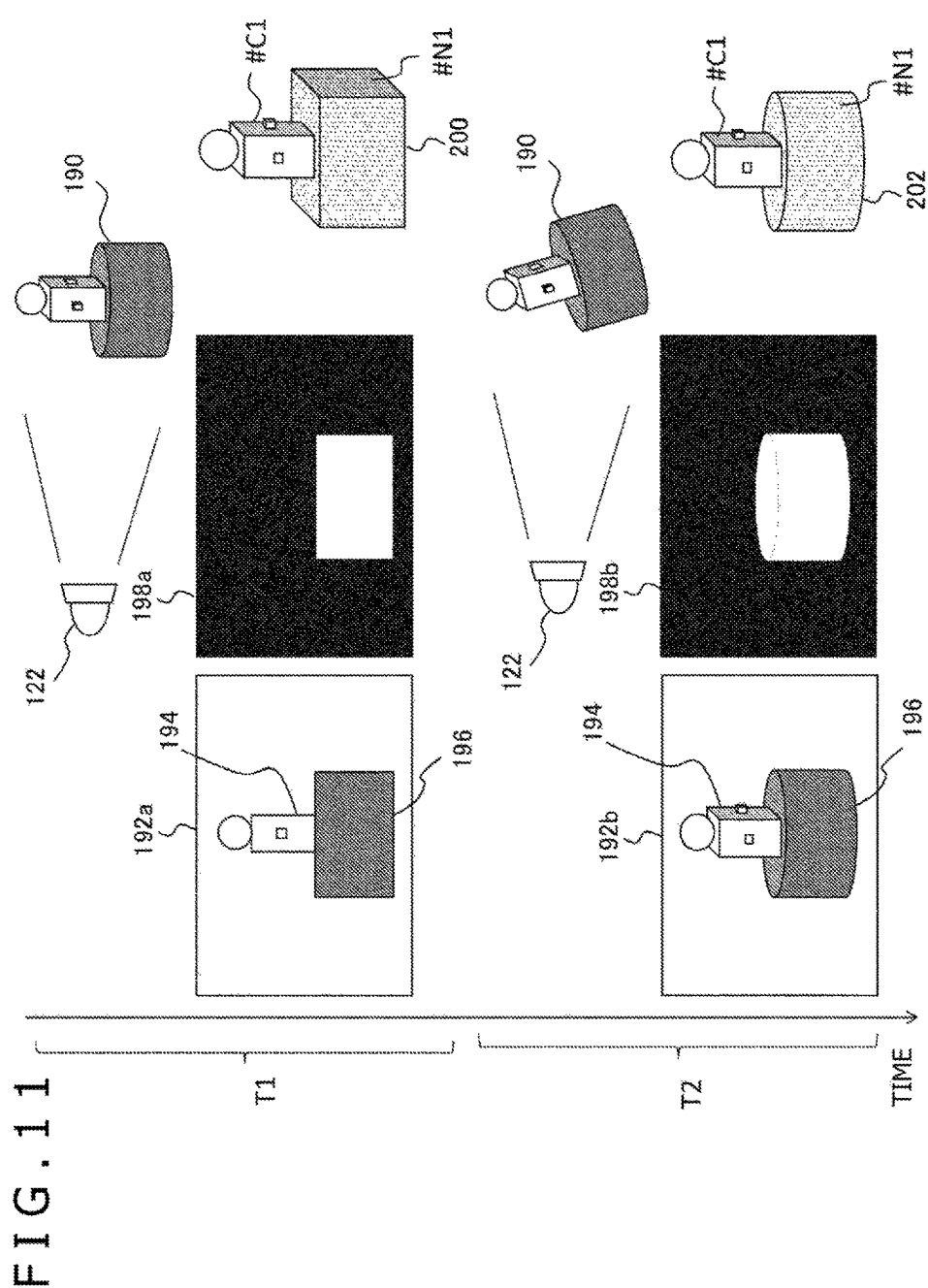
FIG. 11 is a diagram of assistance in explaining processing of identifying the shape of a block set in a time evolving manner in the present embodiment.

FIG. 11 is a diagram of assistance in explaining processing of identifying the shape of the block set in a time evolving manner. An axis of ordinates in the figure indicates time. Suppose that time passes from time "T1" to "T2." In addition, as an example, as depicted in an uppermost row in the figure, a block set 190 is formed by fitting a lower half of a communicating block of a quadrangular prism type provided with a marker (depicted outlined) with a non-communicating block of a circular cylinder type (depicted shaded). First, suppose that at time T1, as in the figure, the camera 122 photographs the block set 190 placed on a horizontal surface from a front. In this case, as depicted in the figure, only the side surface of each block appears as an image in a photographed image 192a.

When a depth image is generated from such an image as described above, and a volume difference from a core whose shape is identified separately is obtained, the remaining part is apparently a quadrangle, which is an image of the side surface of the non-communicating block (depth image 198a). That is, there is a possibility that the three-dimensional shape of the non-communicating block cannot be identified at time T1. However, depending on the resolution of the depth image, distinction between a circular cylinder and a rectangular parallelepiped may be made clear by the presence or absence of a curve of a front surface. In addition, in a case where there is only one non-communicating block coinciding with a size, an aspect ratio, or the like among blocks registered in the non-communicating block information table 180, the shape of the non-communicating block can be identified. Incidentally, the depth image 198a represents volume data generated by obtaining a volume difference between the image of the block set in the depth image obtained from the photographed image and the core, and is not necessarily generated as an image. The same is true for subsequent figures.

In other cases, the structure analyzing section 22 detects candidate non-communicating blocks from the non-communicating block information table 180, and assumes that one of the candidate non-communicating blocks is coupled to the core. Alternatively, a plane identical to a plane of the communicating block whose shape is identified is assumed to be an indefinite face of the non-communicating block. The figure depicts, as an example of the former, a shape 200 of the block set when the non-communicating block is assumed to be a rectangular parallelepiped. Incidentally, the shape 200 of the block set depicted in the figure is a shape recognized at the time point of time T1 in the information processing device 10, and is not necessarily intended to be used for display. The assumed shape depicted in the figure may be rendered as it is during the execution of an application that displays the state of the block set as the 3D object as it is, for example. Alternatively, the assumed shape may not be displayed in any manner, but may only be used as a basis when the shape is corrected in a next time step.

In order to identify the shape of the non-communicating block in a time evolving manner regardless of whether or not display thereof is made, or enable the user to recognize changes in the shape of the block set in a process of being assembled in real time and efficiently, information related to the assumed shape is stored for at least a predetermined period, and is used for later processing. The shape of the block set is managed by giving structural identification numbers (hereinafter referred to as "element numbers") to the communicating block and the non-communicating block constituting the block set. In the figure, the communicating block of the block set is given an element number "#C1," and the non-communicating block of the block set is given an element number "#N1." In the present example, the communicating block and the non-communicating block are distinguished from each other by "C" and "N" of the alphabet. However, this does not limit the format of the element numbers.

These element numbers are associated with the identification numbers given to the respective blocks in advance, the identification numbers being depicted in FIG. 8 and FIG. 10, and are recorded together with information related to connection relation between the non-communicating block and the communicating block (connected faces, connected positions, and orientations). Such information related to the structure of the whole of the block set will hereinafter be referred to as "structure data." Thus managing the structure of each block not only enables display as described above but also can improve efficiency of identifying the shape of the block set in a process of being assembled or the block set that has been modified, because the block set appearing as one body in the image can be divided into units that can be attached and detached by the user. In a case where the shape of the block set is rendered as it is, a polygon and a texture used for the rendering may be generated at this point in time. Then, in subsequent shape identification processing, this 3D model may be corrected, or blocks may be added or deleted.

After a shape such as the shape 200 of the block set or the like is recognized at time T1, photographing and shape identifying processing are continued. At this time, when the user tilts the vertex of the block set 190 to the side of the camera 122, as depicted in the figure, the top surfaces of a communicating block 194 and a non-communicating block 196 are somewhat included in a photographed image 192b at time T2. When a depth image is generated from such an image, and a volume difference from the core in the state at the point in time is obtained, the remaining part includes the top surface of the circular cylinder of the non-communicating block (depth image 198b). It can be determined from the shape of the image that the non-communicating block is highly likely to be a circular cylinder rather than the rectangular parallelepiped assumed at time T1. Reliability of recognition of the shape of the block set is increased by repeating such corrections as the posture of the block set is changed.

At the point in time that the non-communicating block is found to be a circular cylinder, the structure analyzing section 22 replaces the shape of the non-communicating block assumed to be the rectangular parallelepiped at time T1 with the circular cylinder. An accurate shape 202 of the block set is thereby recognized. This processing is actually processing of correcting the identification number of the block of the rectangular parallelepiped type associated with the element number #N1 to the identification number of the block of the circular cylinder type. Alternatively, a polygon model may be corrected. The example of FIG. 11 illustrates the block set having a very simple structure in order to facilitate understanding. However, in actuality, for example, another non-communicating block may be connected in the rear of a non-communicating block, or only a part of a non-communicating block may be seen with the non-communicating block and another block superposed on each other.

In this case, in addition to a method of assuming the shape of each non-communicating block and gradually identifying only a part identified as the user holds the block set and tilts the block set or changes the orientation of the block set, as described above, display may be made to prompt the user to rotate the block set with respect to the camera 122 so that the block set can be photographed from a plurality of directions. In addition, candidate non-communicating blocks may be extracted from the non-communicating block information table 180 on the basis of the shape and color of a part that is not hidden, and be displayed in a list so that the user can specify the real block. In addition, when a two-dimensional bar code indicating a shape or a marker of a figure is affixed to each non-communicating block, the shape may be identified from the photographed image.

Figure 12:
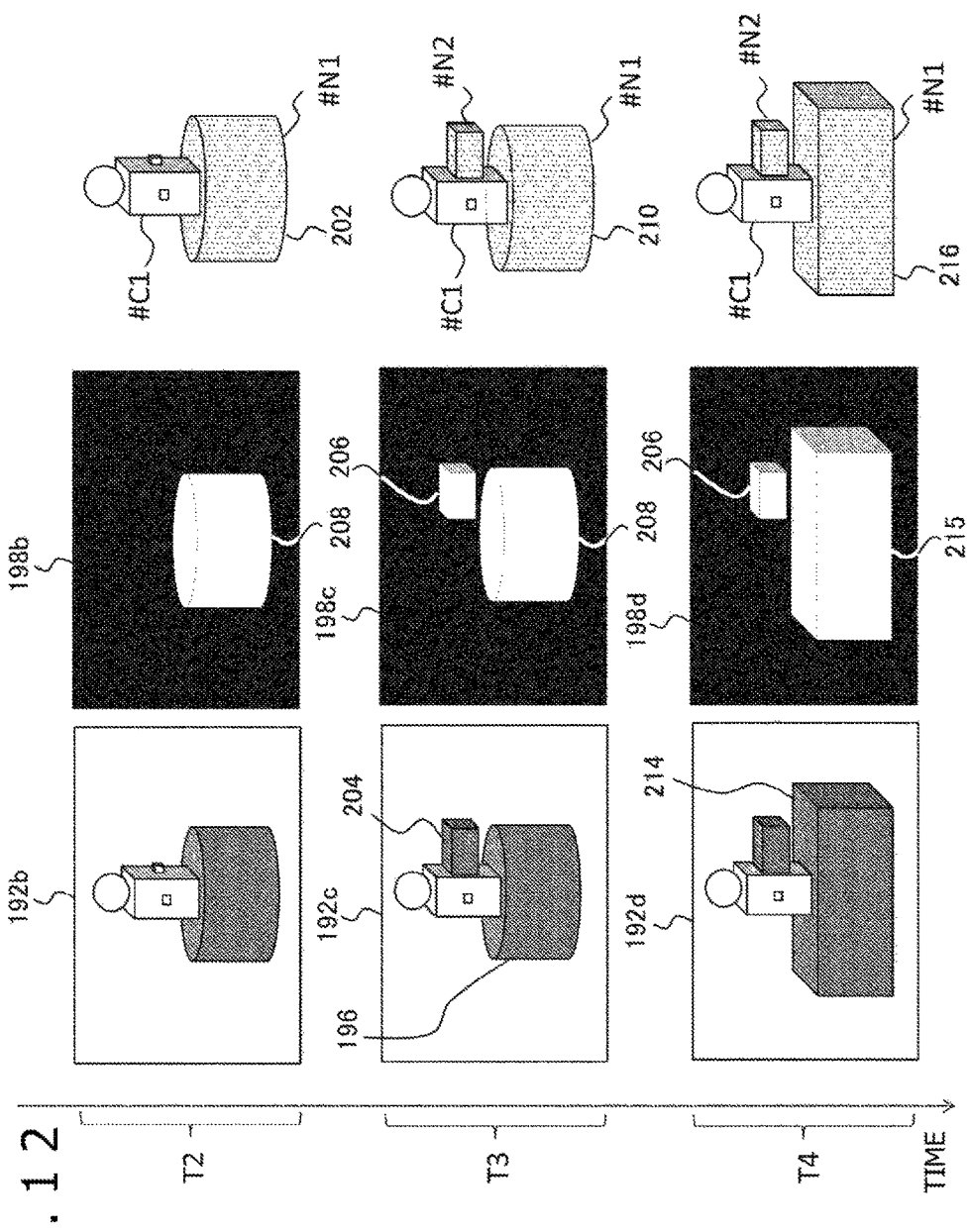
FIG. 12 is a diagram of assistance in explaining processing of identifying the shape of the block set whose structure changes in the present embodiment.

FIG. 12 is a diagram of assistance in explaining processing of identifying the shape of the block set that changes in structure during assembly or the like. A manner of representation of the figure is similar to that of FIG. 11. Depicted in order from the left with an axis of ordinates as a time axis are photographed images 192b to 192d at respective times, depth images 198b to 198d of images excluding the part of the core, and recognized shapes 202, 210, and 216 of the block set. Time T2 in an uppermost row of the figure corresponds to time T2 in FIG. 11. The photographed image 192b, the depth image 198b, and the recognized shape 202 of the block set are also the same. Suppose that from this state, at subsequent time T3, the user connects a new non-communicating block 204 (photographed image 192c). A comparison of the depth image 198c at this time with the depth image 198b at previous time T2 indicates that an image 206 of the new non-communicating block is added.

The structure analyzing section 22 recognizes the connection of the new non-communicating block 204 by comparing the depth image 198b at previous time T2 with the depth image 198c at present time T3. Here, the non-communicating block 196 present also at previous time may be changed in orientation with respect to the camera, or the non-communicating block 196 may not be distinguished from the newly connected block. Accordingly, by continuing to track the position and posture of the once recognized non-communicating block, the structure analyzing section 22 can recognize the same block as identical even when the position and posture of the block are changed. An ordinary tracking technology using an active contour model or the like may be applied as the tracking of the position and posture. Alternatively, a change in orientation of the non-communicating block in the state of being connected to the core may be derived from a change in the position and posture of the core which position and posture can be identified by a signal from the core.

After the connection of the new non-communicating block 204 can be thus detected as a result of comparison of the image after the volume difference, the shape of the non-communicating block is identified by referring to the non-communicating block information table 180, for example, in a manner similar to that described with reference to FIG. 11. Then, the connection relation to the core is identified on the basis of the shape and posture of the core at the identical time. As a result, the shape 210 of the block set at time T3 can be recognized as depicted in the figure. At this time, the structure data is updated by giving a new element number "#N2" to the added non-communicating block, associating the new element number "#N2" with the identification number given in advance to the block in question, and recording the connection relation to the communicating block.

Incidentally, in order to determine whether the non-communicating block present in the field of view of the camera is connected or not connected yet, relative speed between the block set including the core and the block present in the field of view may be monitored. In this case, it is determined that the new block is connected when the relative speed is zero. Suppose that at time T4 subsequent to time T3, the user replaces the previously connected non-communicating block 196 with a non-communicating block 214 of another shape (photographed image 192d). A comparison of a depth image 198d at this time with the depth image 198c at previous time T3 indicates that the shape of an image 215 of the non-communicating block is changed.

When the replacement of the non-communicating block with the other non-communicating block of another shape can be detected as a result of thus comparing the images after the volume differences with each other, the shape of the new non-communicating block is identified by referring to the non-communicating block information table 180 in a similar manner to that described thus far. The connection relation to the core is the same as that of the previously connected non-communicating block. Therefore the previous information can be used as it is. Hence, the shape 216 of the block set at time T4 is recognized as depicted in the figure by updating only the identification number of the previously connected block associated with the same element number "#N1" in the structure data to the identification number of the block identified this time.

Figure 13:
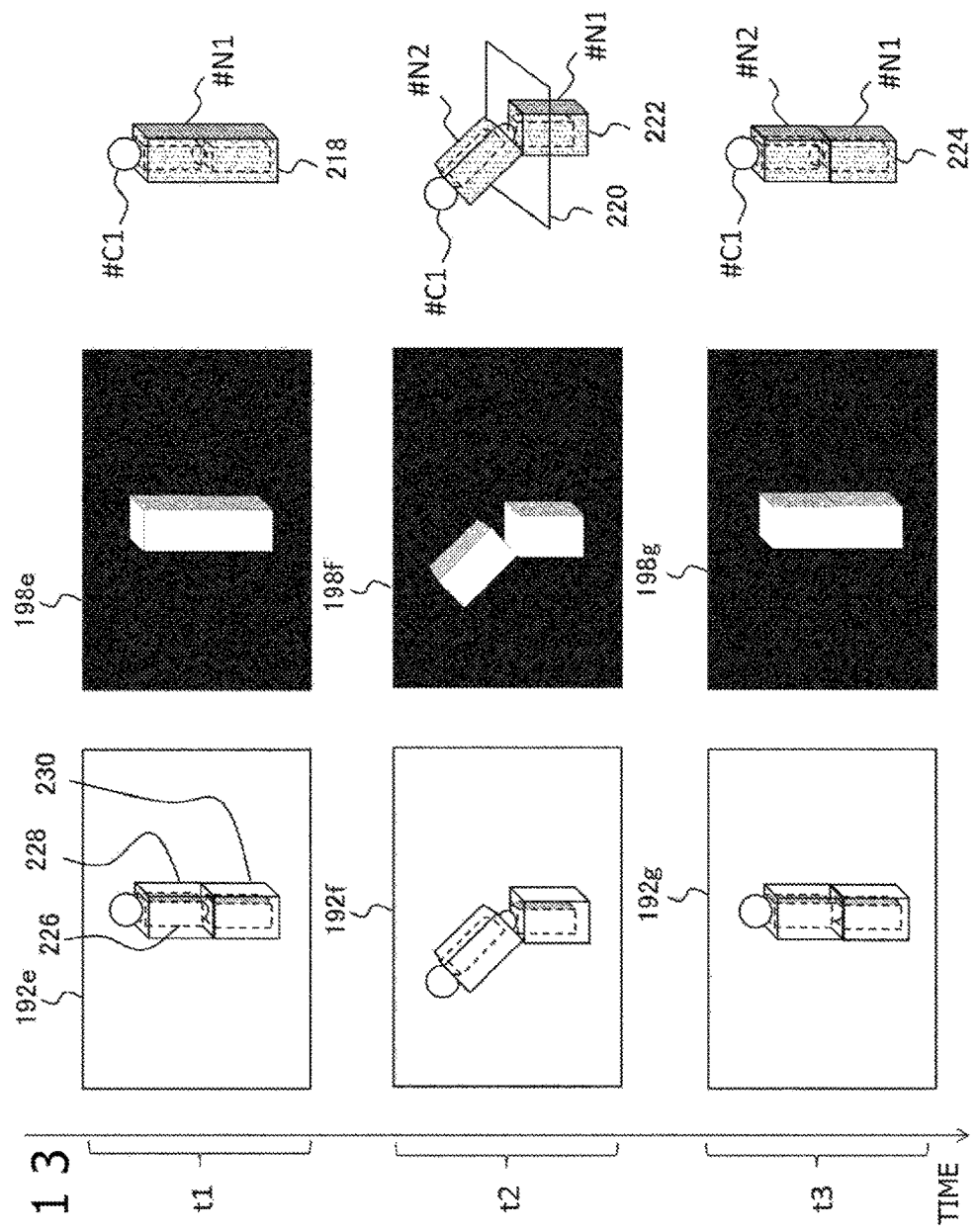
FIG. 13 is a diagram of assistance in explaining processing of identifying the shape of a block set that is modified due to a change in joint angle of a core in the present embodiment.

As an example in which the non-communicating block is modified in other than cases where a non-communicating block of another shape is connected, there may be a case where the joint angle of the core included in non-communicating blocks is changed. FIG. 13 is a diagram of assistance in explaining processing of identifying the shape of a block set modified due to a change in the joint angle of a core. A manner of representation of the figure is similar to that of FIGS. 11 and 12. Depicted in order from the left with an axis of ordinates as a time axis are photographed images 192e to 192g at respective times, depth images 198e to 198g, and recognized shapes 218, 222, and 224 of the block set. However, suppose that the shape of the block set is different from that depicted in FIGS. 11 and 12, and that non-communicating blocks 228 and 230 are respectively fitted so as to include an upper link and a lower link of a communicating block 226 having a marker and a joint.

The non-communicating blocks apparently appear as one body in the depth image 198e after a volume difference which depth image is generated on the basis of the photographed image 192e at time t1 at which the joint is not bent. Hence, the structure analyzing section 22 recognizes the shape 218 of the block set as depicted in the figure by giving element numbers "#C1" and "#N1" respectively to the one (series) communicating block and the non-communicating block assumed to be one block, associating the element numbers with the identification numbers of the respective blocks, and recording connection relation between the communicating block and the non-communicating block as structure data.

Suppose that at time t2, the user next bends the joint of the core (photographed image 192f). A comparison of the depth image 198f at this time with the depth image 198e at previous time t1 indicates that the shape of the non-communicating block is changed. The structure analyzing section 22 has obtained the state of the core included by the non-communicating block from information on the core which information has been separately transmitted from the block set. That is, the structure analyzing section 22 also grasps the joint angle of the communicating block. Hence, when the joint angle of the communicating block present inside is changed at an angle corresponding to the modification of the non-communicating block, it can be determined that the modification of the non-communicating block is caused by the bending of the core.

It is therefore possible to determine that there are actually a plurality of blocks, which have originally been recognized as one block, instead of determining that another block is reconnected. In this case, the structure data is corrected by giving a new element number "#N2" to the non-communicating block (upper block in the figure) whose inclination has changed and using the element number "#N1" as it is for the block whose inclination has not changed, for example. The connection relation to the core is corrected as appropriate as the element numbers are corrected. Thereby the shape 222 of the block set at time t2 can be recognized as depicted in the figure.

In the example of the figure, the distinction between the upper block and the lower block is clear from the inclination angle and the shape of the blocks. However, when the inclination angle is small or the blocks have a shape or a material that makes a gap therebetween inconspicuous even when the angle is changed, a break between the blocks may not be detected easily. In this case, the blocks originally regarded as one block may be divided into two blocks by for example setting a dividing plane 220 perpendicular to the axis of the core when the joint is not bent at the position of the joint, and dividing the blocks by the dividing plane. In this case, the flat surface of the dividing plane 220 is assumed as the upper surface of the lower block and the bottom surface of the upper block, the upper surface of the lower block and the bottom surface of the upper block having been originally in contact with each other, and corrections are made in subsequent shape identification processing.

As a result of the processing at time t2, the non-communicating block is recognized as being constituted of two blocks. Thus, even when a return is made at subsequent time t3 to the state in which the joint of the block set is not bent at time t1 (the photographed image 192g and the depth image 198g), the information processing device 10 can recognize the state as the state in which the two non-communicating blocks are linked to each other (block set 224). Even when the joint of the core is subsequently bent and stretched, processing of identifying a shape anew or the like is not needed because the non-communicating blocks that include the links are managed individually.

In a case where a plurality of blocks are assembled as one body without being thus temporarily changed in orientation or interval, data management may be simplified by treating those blocks collectively as one block. On the other hand, even in a case where a plurality of blocks are assembled as one body, when the plurality of blocks are different from each other in color or texture, and can thus be recognized as different blocks, the blocks may be managed individually on the basis of information on the colors or the textures of the blocks. When even a process in which the user attaches and detaches blocks needs to be recognized correctly, in particular, the correction of the structure data can be limited to parts where a change occurs, by managing each block individually. This is therefore advantageous in terms of processing efficiency.

In addition, when the obtained state of the block set is displayed as an object on the display device 16, or when the structure data is retained as information on a polygon and a texture, low polygon modeling, which roughens resolution, may be performed to reduce a processing load or memory consumption, instead of reflecting the identified shape as it is. Alternatively, each non-communicating block may be further associated with another object model in the non-communicating block information table, and the object model associated with the part of the non-communicating block may be rendered so as to replace the part of the non-communicating block at a time of display. Thus, even when a block has a rough shape such as a rectangular parallelepiped or the like, the block is converted into a realistic object and the object is displayed at a time of display. A setting as to whether to thus make the level of detail of the information lower than, equal to, or higher than that of the real block set is made as appropriate according to processing to be performed by the information processing section 30 using the state of the block set, the processing performance of the information processing device 10, a memory capacity, and the like.

Incidentally, as depicted in FIGS. 11 to 13, the present embodiment obtains temporal changes in the block set with regard to both of the core and the non-communicating blocks. Hence, various modes can be realized by storing the temporal changes as a history for a predetermined time, and reading out and using the history as required. For example, when the user desires to return the block set in a process of being assembled to a state preceding by a few stages, and the user makes a request via the input device 14, a state of the block set in the corresponding stage is displayed as a 3D object. The user can return the real block set to the previous state while viewing the 3D object. When a virtual viewpoint with respect to the block set rendered as the 3D object is changed by the input device 14, the previous state of the block set can be checked from a plurality of directions. When the history is stored for a long time, the block set created in the past can be displayed as an object in each making stage, and the real block set can be reproduced by assembly according to the object.

In addition, information on a block once detached, such as the non-communicating block 196 of the circular cylinder type in FIG. 12, may remain provided with the previous element number without being deleted from the structure data immediately, and may be managed by a flag indicating that the block is detached or the like. In this case, when another block is attached to the same position, the same element number is given to the plurality of non-communicating blocks. However, the flag can distinguish the present information from the past information. When the user then makes a request to return the block set to the previous state, the object of the block set in the previous state can be displayed by detecting and returning the previous block from the structure data.

Figure 14:
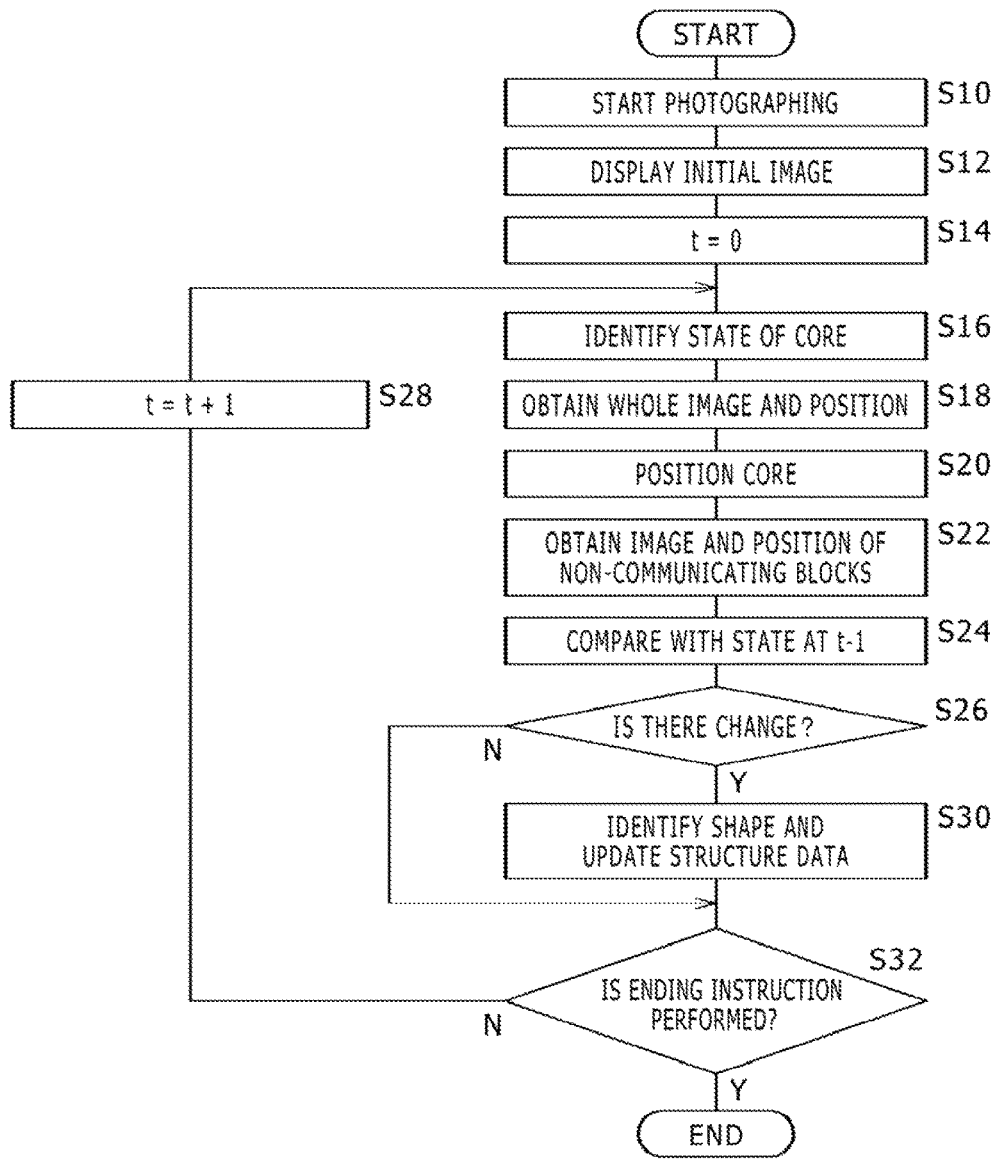
FIG. 14 is a flowchart depicting a processing procedure for identifying the state of a block set including a non-communicating block in the present embodiment.

Description will next be made of operation of the information processing device in relation to identification of the state of the block set, which operation can be realized by the configuration described thus far. FIG. 14 is a flowchart depicting a processing procedure for identifying the state of a block set including a non-communicating block. This flowchart is started when the user turns on power to a block having a battery among blocks of the block set 120, and inputs an instruction to start processing via the input device 14 by selecting an application on the information processing device 10, for example.

Incidentally, suppose that a signal indicating the state of the core is transmitted in predetermined timing from the block set being assembled or lifted up by the user, in parallel with the processing of the information processing device 10 which processing is to be depicted in the following. In addition, this flowchart directs attention to a change in a non-communicating block, and suppose that a change in the state of the core is separately obtained from the signal indicating the state of the core or the like. First, the structure analyzing section 22 makes the camera 122 start photographing the block set (S10). Meanwhile, a predetermined initial image is displayed on the display device 16 by cooperation between the information processing section 30 and the display processing section 32 (S12). The image displayed at this time may be a live video photographed by the camera 112, an image created in advance as a part of an application, such as a game image, or the like.

In time step t=0 (t is an integer indicating the passage of time in ascending order), when the core information receiving section 20 receives information transmitted from the block set, the structure analyzing section 22 identifies the posture and shape of the core in the three-dimensional space on the basis of the information (S14 and S16). When the position of the core is identified by means other than a photographed image, the position of the core is also identified. Meanwhile, the structure analyzing section 22 obtains the whole image and position of the block set by for example obtaining the photographed image from the camera 122 and generating a depth image on the basis of the photographed image (S18). A thing other than the block set, a background, a hand of the user, and the like may appear in the photographed image. Thus, processing of removing these images is performed in some stage.

An ordinary method such as foreground extraction, a simultaneous localization and mapping (SLAM) method, color segmentation, dictionary-based object recognition, or the like can be used for this processing. How the core is located with respect to the thus extracted whole image of the block set is identified (S20). Specifically, as described above, a part having a characteristic shape, color, or pattern or the like, such as the marker of the core or the like, is detected from the image of the block set, and the position of the core is determined with reference to the part. Then, how the core is seen from the camera is identified on the basis of the shape and posture of the core which shape and posture are identified in S16. This is the image of the block set when there is no non-communicating block. Thus, the image and position of the non-communicating block are obtained by taking a volume difference between the image of the block set when there is no non-communicating block and the whole image of the real block set (S22).

When the state of the non-communicating block is obtained in previous time step t−1, the state of the non-communicating block in previous time step t−1 and the present image of the non-communicating block are compared with each other (S24) to check whether or not there is a change (S26). When there is a change in the shape of the image (Y in S26), processing of identifying the shape of the non-communicating block and updating the structure data of the block set is performed (S30). Incidentally, at time step t=0, the state itself of the non-communicating block which state is obtained in S22 is regarded as a change, and structure data is newly created on the basis of the state of the non-communicating block.

As for the processing of S30, as described with reference to FIGS. 11 to 13, the processing of S30 is classified into processing in a case of addition or removal of a non-communicating block, processing in a case of replacement with another non-communicating block, and processing in a case of a change in shape of the non-communicating block due to bending of the joint of the core, and the processing to be performed for each case is performed. Specifically, when non-communicating blocks are added, element numbers are given and are each associated with shapes, connecting directions, and the like, and connection relation to the core is recorded. When a non-communicating block is removed, the non-communicating block is managed by deleting the non-communicating block from the structure data or setting a flag indicating that the non-communicating block is removed, for example. When replacement with another non-communicating block is performed, the shape, connecting direction, and the like of the block corresponding to the corresponding element number are updated.

At a time of a change in shape due to bending of the joint of the core, when the non-communicating blocks are not managed in such a manner as to correspond to the respective links having the joint interposed therebetween, these blocks are set as separate blocks, a new element number is given to one of the blocks, and the shapes and connecting directions of the respective blocks are updated. The non-communicating blocks are thus managed individually. In addition, even when the shape of the core or the non-communicating block is not changed, the image of the non-communicating block is changed according to a change in position or posture. In this case, whether at least a part of the shape of a part assumed because the shape of the part cannot be determined due to hiding of the part or the like can be identified is checked. When a part of the shape of the assumed part is identified, the structure data is updated accordingly. The shape is thus identified in a time evolving manner. As described above, the structure data may be represented as model data of 3D graphics.

When there is no change in the shape of the image in S26 (N in S26), at least the state of the non-communicating block is not changed, and therefore the processing of S30 is not performed. Until the user performs input for ending the processing, the processing from S16 to S30 is sequentially repeated while time step t is incremented (N in S32 and S28). The processing is ended when an instruction input for ending the processing is performed by turning off the power to the block set, for example (Y in S32). Incidentally, when the whole of the core is hidden by the non-communicating block as viewed from the camera in the processing of S20, the positioning of the core cannot be performed. In this case, a display may be made which prompts the user to change the orientation of the block set so that the core comes into the field of view of the camera. Alternatively, a camera coordinate system with respect to the core may be assumed such that the whole image of the core does not protrude from the whole image of the block set, and may be corrected in a subsequent time step.

Incidentally, attention has been directed mainly to a change in shape of the non-communicating block in the description thus far. The structure data can be updated by similar processing also in a case where the color or texture of the non-communicating block is changed. In this case, however, the part of the core is first removed from the whole image of the block set by positioning the whole image and the core in the depth image, and then the change in the color or texture is identified by feeding back a region of an image of the remaining non-communicating block to the photographed color image.

Figure 15:
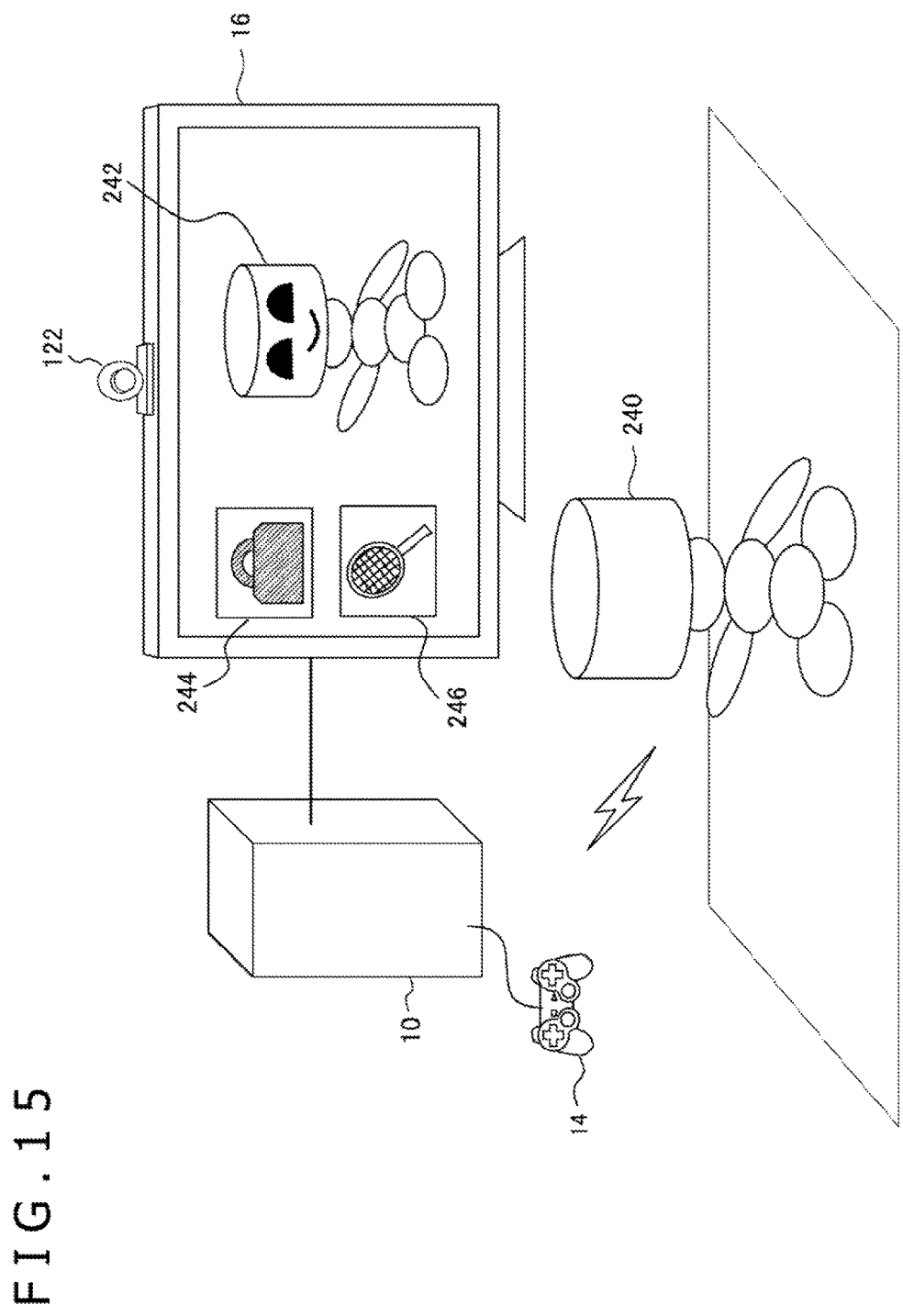
FIG. 15 is a diagram illustrating relation between a block set and display that can be realized in the present embodiment.

FIG. 15 illustrates relation between the block set that can be realized by the mode described thus far and display. In the example of the figure, a block set 240 including a communicating block and a non-communicating block is rendered as a 3D object 242 as recognized by the information processing device 10, and displayed on the display device 16. Because the shape, posture, color, and the like of the non-communicating block are obtained by the camera 122, a thing not registered in the non-communicating block information table, for example a thing made by the user himself/herself can be recognized. For example, even when the user writes the face of a doll assembled as the block set 240 in the figure with a felt-tip pen or pastes a sticker to the doll, a doll having a face similar to the written face or a doll to which the sticker is pasted is rendered as a 3D object.

In the present example, the block set present in the field of view of the real camera 122 is flipped horizontally by mirror processing, and is represented as an object. Because the block set 240 faces the camera 122 on the display device 16, the 3D object 242 on the display is displayed such that the block set 240 appears in a mirror. On the other hand, the information processing device 10 recognizes the three-dimensional shape of the block set 240 as described above, and can therefore change a virtual viewpoint with respect to the 3D object 242 freely. Hence, even an image on the back side of the doll which side is in a blind spot from the camera 122 at this point in time can be displayed without the block set 240 being rotated. However, depending on the shape identification processing thus far, details of the shape on the back side may not be determined.

The description thus far is based on recognition of the state of the actually assembled block set. However, a thing not actually connected may be allowed to be virtually connected. A screen illustrated in FIG. 15 displays images 244 and 246 of options of items to be provided, together with the 3D object 242 reflecting the block set 240. When the user selects one image, and makes the 3D object 242 on the screen have a corresponding item via the input device 14 or by moving the block set 240, for example, the information processing device 10 may update the structure data so as to indicate that the corresponding item is connected to the corresponding position of the block set already recognized.

The three-dimensional shapes of the items as options are retained in the block information storage section 24 or the model data storage section 26 of the information processing device 10. Consequently, in subsequent processing, regardless of whether an item on the screen is actually connected to the block set or virtually connected, the item can be represented so as to move in the virtual world in a state of being held by the 3D object 242 according to the movement of the block set in the real space. When three-dimensional shape information is obtained by capturing a real thing made by the user himself/herself or the like by a 3D scanner, the three-dimensional shape information serves as a substitute for the above-described item. That is, even when a real thing of a non-communicating block is not actually connected, the non-communicating block can be displayed as if the non-communicating block were connected on the screen.

Figure 16:
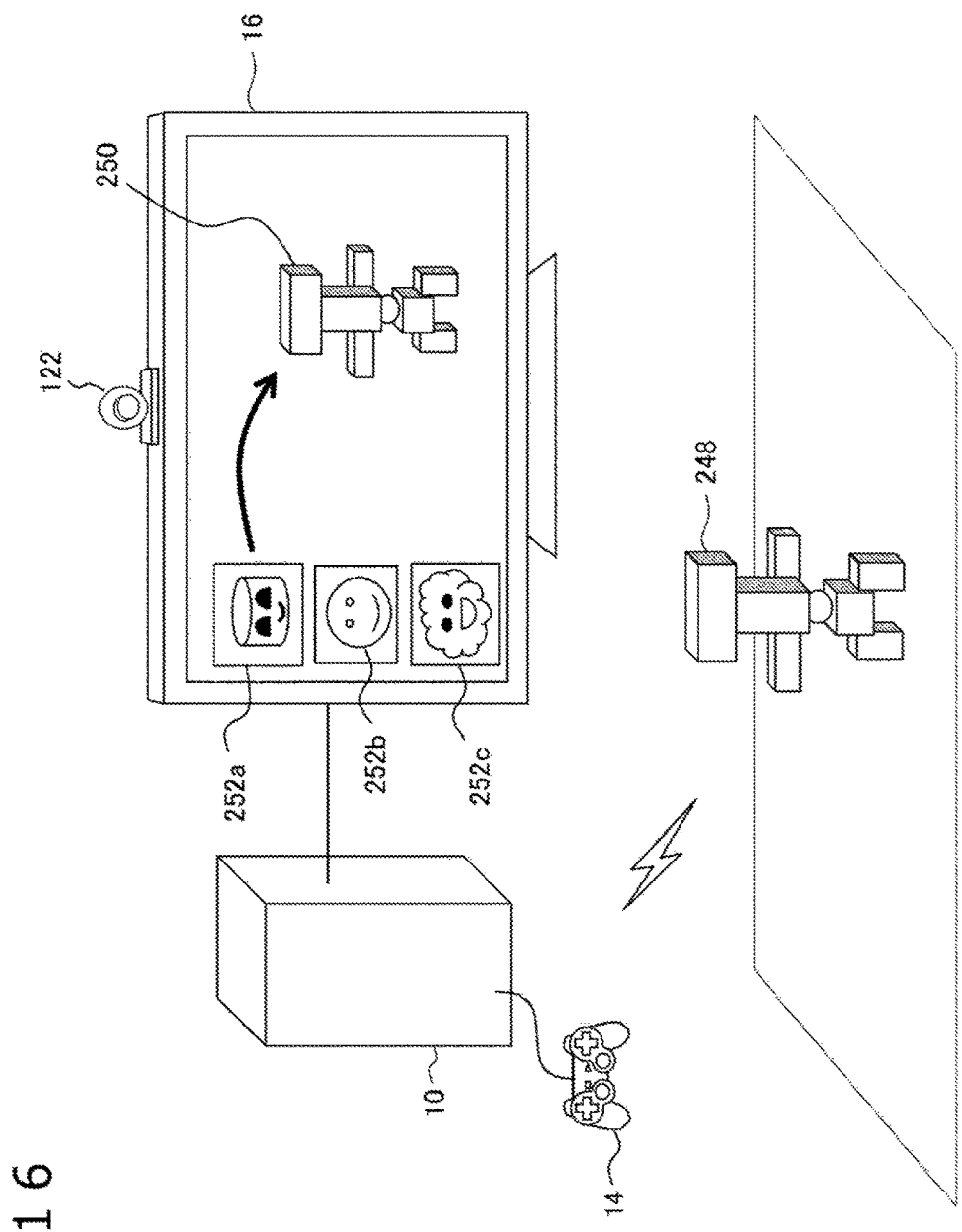
FIG. 16 is a diagram illustrating relation between a block set and display in a case where an external appearance is set to the block set in the present embodiment.

The external appearance itself of the block set may be created in the virtual world on the display by a similar method. FIG. 16 illustrates relation between a block set and display when an external appearance is set to the block set. In the present example, as compared with the case of FIG. 15, the block set 248 itself is of a simple configuration such for example as only communicating blocks or the like. When recognizing the state of such a block set 248, the information processing device 10 displays, on the display device 16, the state of the recognized block set as it is or as a 3D object 250 after flipping the block set horizontally. Then, as in the case of the items of FIG. 15, images 252a, 252b, and 252c of options of 3D objects as candidates are displayed for each part such for example as a face or the like.

The user performs selecting input from the image 252a, 252b, or 252c for each block of the block set or each part formed by a plurality of blocks, and thereby virtually makes connections to the 3D object 250. An external appearance is thus completed. It is consequently possible to create the 3D object having various external appearances freely, and further move the 3D object according to the movement of the real block set 248 or change the virtual viewpoint. In addition, virtual 3D objects may be coupled to each other on the display by connecting a plurality of block sets whose virtual external appearances are thus created.

For example, a mode can be realized such that when a block set and an external appearance corresponding to the block set are created for each part in the completed form of a 3D object as an objective and a block set is finally connected, the completed form having an external appearance in which even detailed parts are set is displayed. Alternatively, a procedure of storing a 3D object having a virtual external appearance once created and creating a 3D object having another external appearance using the same block set may be repeated, and a plurality of 3D objects thus created may be coupled to each other only in the virtual world. In this case, a mode can be realized in which all of the 3D objects coupled to each other move according to the block set as a 3D object associated finally with the block set is interlocked with the block set.

In the examples of FIGS. 15 and 16, the movement of the block set is reflected in the 3D object in the virtual world. Conversely, the movement of the 3D object may be reflected in the movement of the block set. For example, a 3D object representing a block set assembled by the user or a 3D object virtually created by the user so as to correspond to the block set is made to appear as a character in a game executed by the information processing section 30. When the user performs game operation using the input device 14, and the 3D object moves accordingly, the real block set is also made to move. In this case, the driving control section 34 transmits a signal for controlling the driving section 148 of the block set in such a manner as to correspond to the movement of the 3D object.

In the example of FIG. 16, a mode is assumed in which the user applies 3D objects in units of one or a plurality of blocks. Thus, correspondence relation between the real blocks and the virtual objects is similar to that of non-communicating blocks, and management can also be performed in a similar manner. That is, when the joint angle of the real block set is changed, a position where a modification is caused by the change is also clear in the 3D object, and therefore the change can be reflected in screen display easily. The same is true for a case where the movement of the 3D object is reflected in the block set. On the other hand, when one 3D object is associated with the whole of the assembled block set, corresponding positions of the block set and the 3D object need to be set appropriately in order to interlock the block set and the 3D object with each other suitably.

Figure 17:
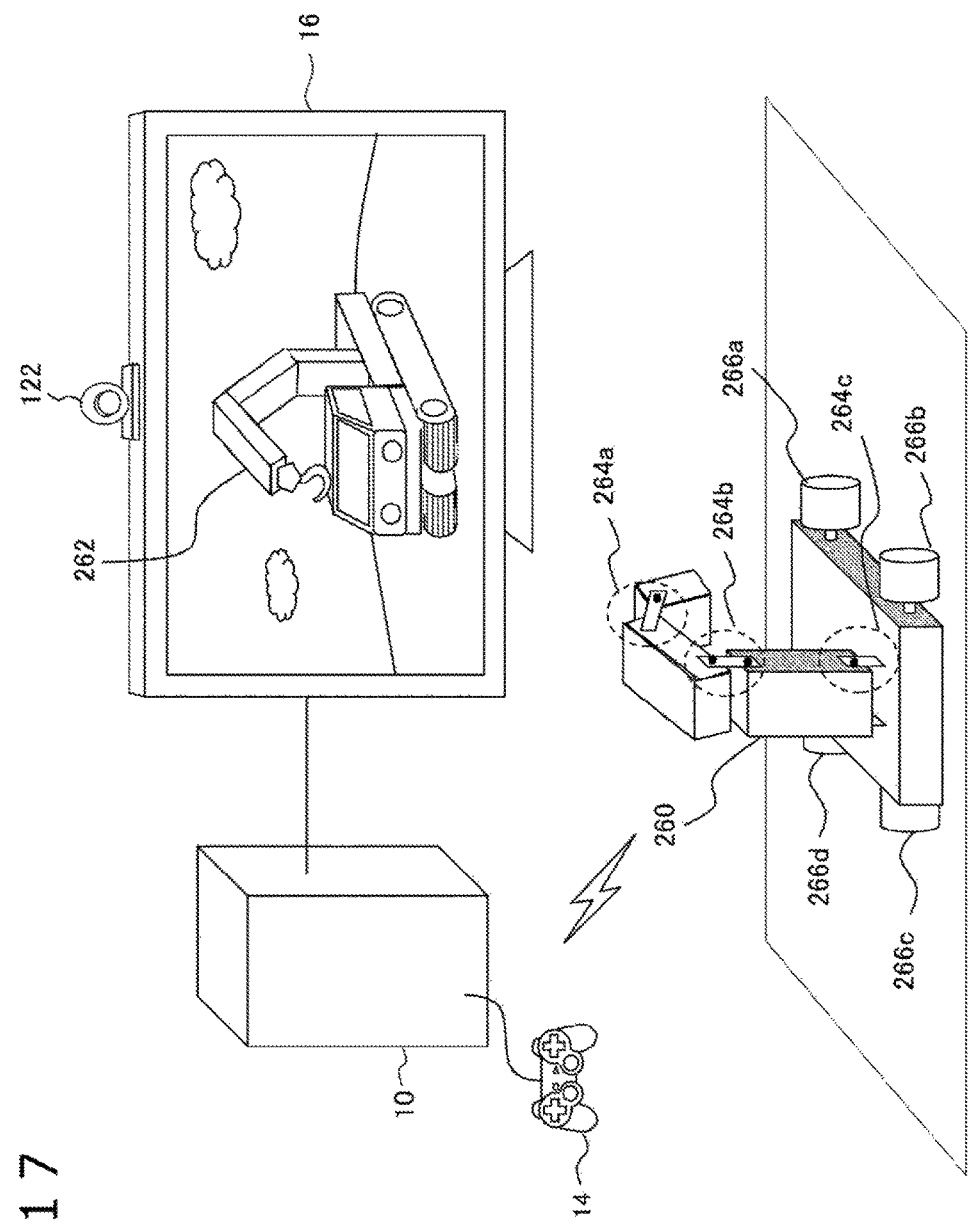
FIG. 17 is a diagram illustrating relation between a block set and display in a case where one 3D object is associated with the assembled block set in the present embodiment.

FIG. 17 illustrates relation between a block set and display in a case where one 3D object is associated with the assembled block set. The present example assumes a case where the user creates a block set 260 assumed to represent a crane truck, and selects a crane truck 262 as a 3D object on display. The block set 260 includes a plurality of joints 264a, 264b, and 264c provided to a block assumed to represent a crane, and further includes wheels 266a, 266b, 266c, and 266d fitted to a block serving as a platform.

When the user bends and stretches the joints of the block set 260, and moves the crane truck 262 on the screen in the same manner, for example, positions of the crane truck 262 at which positions the bending and stretching of the joints 264a, 264b, and 264c is to be reflected need to be set. In addition, when the movement of the crane truck 262 on display is to be reflected in the actual movement of the block set 260, the role, rotational speed, steering angle, and the like of each wheel need to be determined according to the movement on display. The block set 260 in the present embodiment is assembled by the user freely. Thus, parts desired to be moved as parts of the crane, the front-rear relation of the crane truck, and the like largely depend on intentions of the user. Accordingly, description will be made of a method of setting correspondence relation between the movement of a thing thus freely assembled and the movement of a 3D object prepared in advance.

Figure 18:
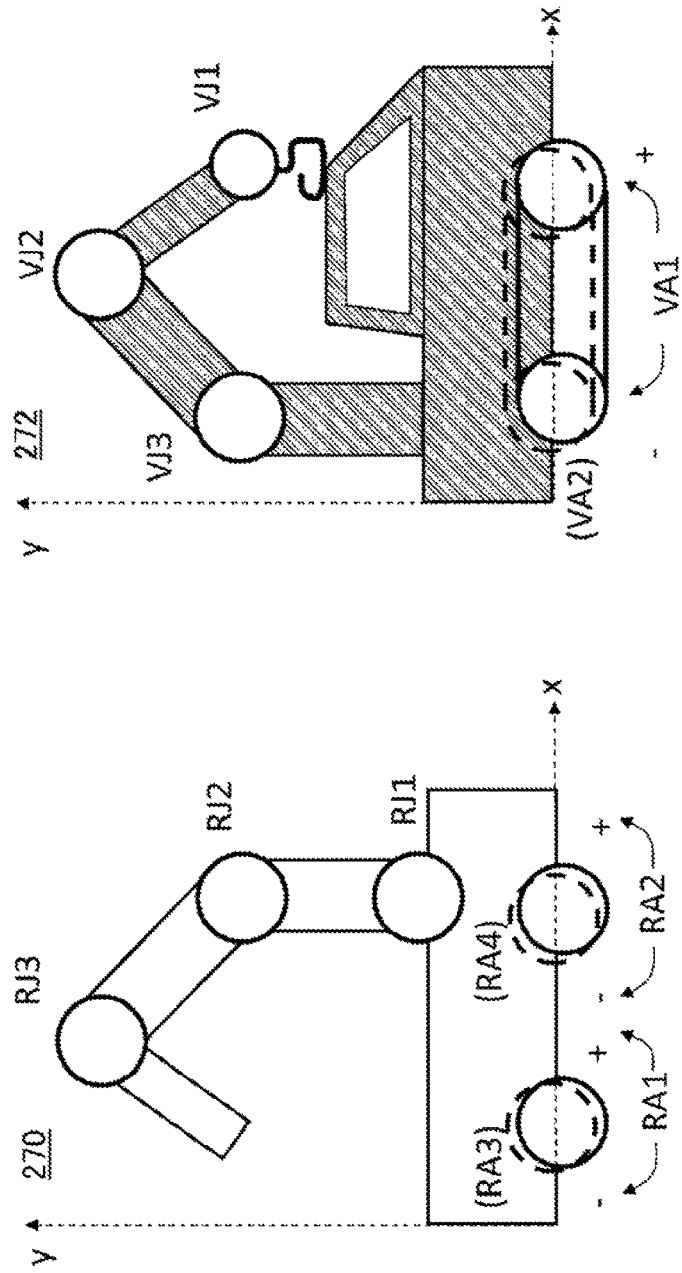
FIG. 18 is a diagram illustrating information necessary to associate movements of the block set and the 3D object with each other in the present embodiment.

FIG. 18 illustrates information necessary to associate the movements of the block set and the 3D object with each other. The left side of the figure is a schematic diagram of a block set 270 corresponding to the block set 260 in FIG. 17. The right side of the figure is a schematic diagram of a crane truck 272 corresponding to the crane truck 262 of the 3D object in FIG. 17. As depicted in the figure, a coordinate system used when the information processing device 10 recognizes the shape is set to the block set 270, and a local coordinate system with respect to the 3D model is set to the crane truck 262. The two coordinate systems are set independently of each other. The orientations of the block set 270 and the crane truck 272 in the respective coordinate systems therefore vary.

In order to facilitate understanding, the example of FIG. 18 illustrates shapes in a two-dimensional plane formed by an x-axis and a y-axis, that is, side surface shapes when the block set 270 and the crane truck 272 are defined in a state of being parallel with the x-axes of the respective coordinate systems. However, the orientations of the block set 270 and the crane truck 272 with respect to the respective coordinate systems are opposite from each other with respect to the x-axes. Here, three joints of the block set 270 are denoted by RJ1, RJ2, and RJ3, and three joints of the crane truck 272 are denoted by VJ1, VJ2, and VJ3. In addition, four wheels of the block set 270 are denoted by RA1, RA2, RA3, and RA4, and caterpillar tracks of the crane truck are denoted by VA1 and VA2. Incidentally, the wheels RA3 and RA4 and the caterpillar track VA2 are on the opposite side surface from the display surface, and are normally hidden. In FIG. 18, however, the wheels RA3 and RA4 and the caterpillar track VA2 are depicted shifted as indicated by dotted lines, and the references are depicted in parentheses.

A simplest method for interlocking such a block set 270 and such a crane truck 272 with each other may be to respectively associate the joints RJ1, RJ2, and RJ3 of the block set 270 with the joints VJ1, VJ2, and VJ3 of the crane truck 272, and associate the wheels RA1 and RA2 with the caterpillar track VA2 not depicted in the figure and associate the wheels RA3 and RA4 with the caterpillar track VA1. In the present example, however, the positions of the joints of the cranes differ between the block set 270 and the crane truck 272. Thus, when the corresponding joints of the block set 270 and the crane truck 272 are bent at same angles individually, for example, a movement as expected by the user may not occur.

In addition, in general, the joint angles of the block set 270 have a physical movable range, and the joints of the crane truck 272 also have a movable range as a model. When such constraint conditions are not considered, there may be a case where the 3D model is bent at an impossible angle, or a case where the joint angle of the block set reaches a limit and the block set does not move further. In addition, due to the difference in orientation with respect to the coordinate systems, there may be a case where the crane truck 272 on display is backed when the block set 270 is advanced. In order to prevent such a problem, the interlocking of a real thing with a thing in the virtual world is coordinated by performing processing of setting a common coordinate system, setting corresponding positions, and associating concrete movements of the corresponding positions with each other.

Figure 19:
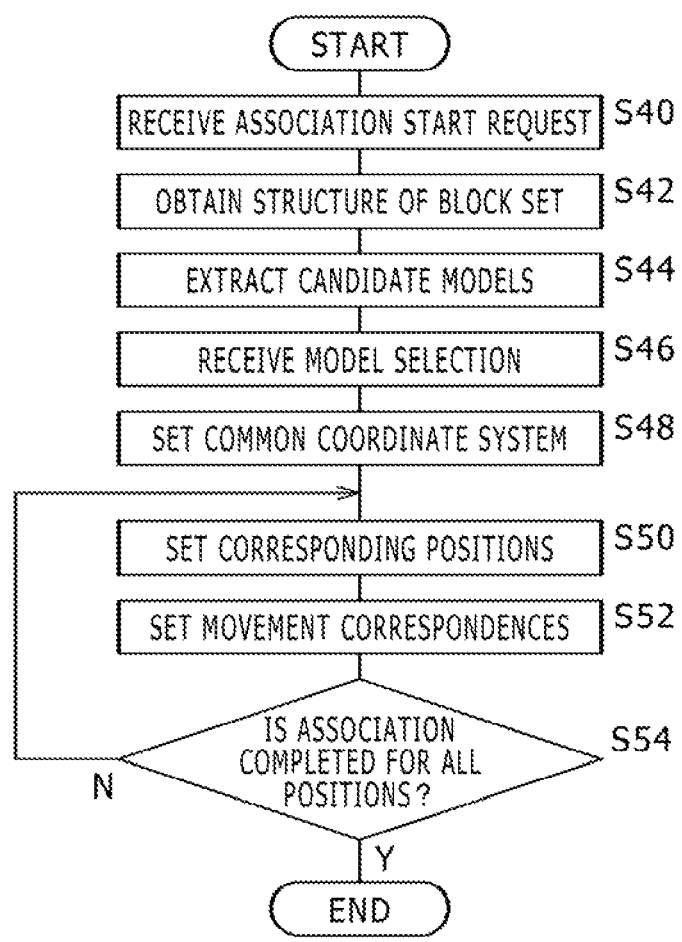
FIG. 19 is a flowchart depicting a processing procedure by which the information processing device associates the movements of the block set and the 3D object with each other in the present embodiment.

FIG. 19 is a flowchart depicting a processing procedure by which the information processing device 10 associates the movements of the block set and the 3D object with each other. First, after the user assembles the block set into a desired shape, the user inputs an instruction request to start association with a 3D object via the input device 14. When the information processing section 30 of the information processing device 10 receives the request (S40), the information processing section 30 obtains information related to the structure of the assembled block set from the structure analyzing section 22 (S42). Then, a suitable model is extracted as a candidate from among 3D objects whose rendering data is prepared in the model data storage section 26 on the basis of the shape of the block set or the like (S44).

The model data storage section 26 associates the rendering data of various kinds of object models such as a crane truck and the like with metadata indicating the features of each model, and stores the rendering data and the metadata associated with each other. The metadata includes features as things, structural features, and external features, when roughly classified. The features as things include for example items such as a human, an animal, a vehicle, a food, and the like, proper nouns such as the name of a movie, an animation, or a game in which a character appears, the name of the character, and the like, and related periods such as the primitive age, the Middle Ages, the present age, the future, a particular year, and the like. The structural features include the number of joints, the movable angle and degree of freedom of each joint, the length and thickness of a link, the connection relation of a joint, a driving force, a tire diameter, and the like.

The external features include a color, a surface shape, the number or volume of non-communicating blocks, the covering ratio of a non-communicating block in the block set, the number of LEDs or display devices when the LEDs or the display devices are provided, the kinds of the display devices, and the like. In the model data storage section 26, such various features are associated with each model. The more the associated features, the higher the accuracy of extraction of suitable candidates. However, not all of the features are intended to be associated. In S44, the information processing section 30 extracts candidate models having high degrees of similarity to the real block set from the information related to the shape or structure of the block set which information is obtained in S42 on the basis of the structural features and the external features.

For example, letting $N_{RJ}$ be the number of joints of the block set, $N_{RA}$ be the number of wheels of the block set, $N_{VJ}$ be the number of joints of the 3D object, and $N_{VA}$ be the number of wheels of the 3D object, a similarity degree evaluation value is calculated by the following equation.

$$\text{Similarity Degree Evaluation Value} = (N_{RJ} - N_{VJ}) \times w_J + (N_{RA} - N_{VA}) \times w_A$$

where $w_J$ and $w_A$ are weights for the evaluation of the number of joints and the evaluation of the wheels, and are determined according to the importance of the evaluation of the number of joints and the evaluation of the wheels. The closer to zero the evaluation value, the higher the degree of similarity. In addition, when the evaluation value is positive, the evaluation value indicates a tendency for the block set to have a large number of joints or wheels. When the evaluation value is negative, the evaluation value indicates a tendency for the 3D object to have a large number of joints or wheels. When there is a 3D object that makes the evaluation value zero, the 3D object is extracted as a most probable candidate model.

Further, when there are a plurality of 3D objects for which evaluation values having a same absolute value but different from each other in sign are obtained, the 3D object providing the negative evaluation value is extracted preferentially. This is because as the number of joints or wheels of the 3D object is increased, more detailed movement can be expressed on the screen, and the movement of the block set can be expressed more richly. Before the evaluation of such a degree of similarity, the candidates may be narrowed down on the basis of a feature selected by the user from among the features as things. Features as things, structural features, and external features may be combined with each other as appropriate to extract candidates, or the user may be allowed to specify also features other than the features as things.

The information processing section 30 displays the plurality of candidate models thus extracted on the display device 16, and receives a selecting input performed by the user via the input device 14 or the like (S46). An example of the model thereby selected is the crane truck 272 depicted in FIG. 18. Next, a coordinate system common to the block set and the object in the image is set (S48). Thus, parameters determining the posture and traveling direction of the block set can be similarly handled also in the 3D object. For example, when the block set 270 in FIG. 18 is advanced in the negative direction of the x-axis, the coordinate system is set such that the crane truck 272 of the 3D object is also advanced in the negative direction of the x-axis. In addition, the common coordinate system makes it possible to make a common definition of a joint angle, and properly determine which link is moved with respect to the joint when the joint angle is changed.

The various kinds of parameters defined in the common coordinate system are subjected to coordinate transformation into values in the local coordinate system originally set to the 3D object, and is thereby reflected in the rendering of the 3D object. When the shapes of the block set and the 3D object are similar to each other, and the front and rear thereof or the like are clear, the information processing section 33 sets the common coordinate system such that both of the block set and the 3D object have the same orientation. Alternatively, the user may adjust the orientation of the 3D object on the screen so that the orientation of the 3D object becomes the same as the orientation of the block set, and the information processing section 30 may set the coordinate system with the orientation as a reference. Thus, even the block set whose front and rear are unclear can be interlocked with the 3D object in the orientation intended by the user.

Next, corresponding positions of the block set and the 3D object are set (S50). When the numbers of joints or the connection relations of links of the block set and the 3D object coincide with each other, this processing can be performed collectively by the information processing section 30. Specifically, on the basis of the structure of the block set which structure is obtained in S42 and the structure of the object model selected in S46, the information processing section 30 geometrically derives corresponding joints of the block set and the object model, and associates the corresponding joints of the block set and the object model with each other. Alternatively, a setting screen is displayed to allow the user to make the setting. The positions associated in this case are typically joints or wheels in FIG. 18. However, for a position at which a change such as bending, rotation, displacement, or the like of the block set is desired to be reflected, the user is allowed to set the corresponding point on the 3D object side freely. This makes it possible to move an animal without any joint, such as a mollusk or the like, or make a thing that does not bend in actuality bow.

Incidentally, the associated positions do not necessarily need to be in one-to-one relation. That is, a plurality of joints of the block set may be associated with one joint of the 3D object, or a plurality of joints of the 3D object may be associated with one joint of the block set. The same is true for wheels. In a case where the overall structures of the block set and the 3D object can be made to coincide with each other by regarding a plurality of joints as one joint even when the block set and the 3D object have different numbers of joints, the information processing section 30 may group the joints in such a manner.

In this case, for example, one group of joints of one of the block set and the 3D object is associated with one joint of the other. At this time, a change in the joint angle of the latter is allocated to the movements of the one group of joints of the former. A concrete example will be described later. Irrespective of whether or not the joints are grouped, the information processing section 30 sets the correspondence in consideration of not only the overall structures of the block set and the 3D object but also the movable angles of the respective joints. For example, joints having a same movable angle are associated with each other. Thus, a degree of similarity between joints may be evaluated from various viewpoints such as the overall structures, movable angles, and the like, and joints whose evaluation value is higher than a threshold value may be associated with each other. Information on the corresponding positions set by the information processing section 30 or the user is stored in the correspondence information storage section 28.

Next, movement correspondences are set for the thus associated positions (S52). That is, a setting is made as to whether or not to reflect a change in the joint angle as it is, or when a joint is not associated on a one-to-one basis, a ratio at which to allocate the change in the joint angle or the like is set. When the structures of the block set and the 3D object coincide with each other, and the movable angles of corresponding joints are equal to each other, the joint angles can be basically regarded as similar to each other, and therefore the information processing section 30 makes a setting in such a manner. When the structures are made similar to each other by grouping joint angles, a change in one joint angle is allocated to the movements of joints belonging to one corresponding group, as described above. At this time, an allocation ratio may be determined according to a ratio between the movable angles of the respective joints.

When a movement correspondence can be thus set by a rule set in advance, the information processing section 30 may make the setting. Further, a setting screen is displayed to allow the user to set a movement correspondence freely, or correct an already set correspondence relation. In addition, when the movement of the vehicle of the 3D object is reflected in the movement of the vehicle of the block set, the speed of the vehicle of the 3D object on display and the rotational speed of the axles of the block set are associated with each other. This relation changes according to the diameter of the wheels connected to the block set. Thus, when the diameter of the wheels is known, the information processing section 30 can determine the rotational speed of the axles of the block set by operation. When the diameter of the wheels is not known, a necessary parameter is obtained when the user actually moves the block set, as will be described later. The processing of S50 and S52 is repeated for all of positions to be associated (N in S54). When all of the positions are associated, the processing is ended (Y in S54).

Figure 20:
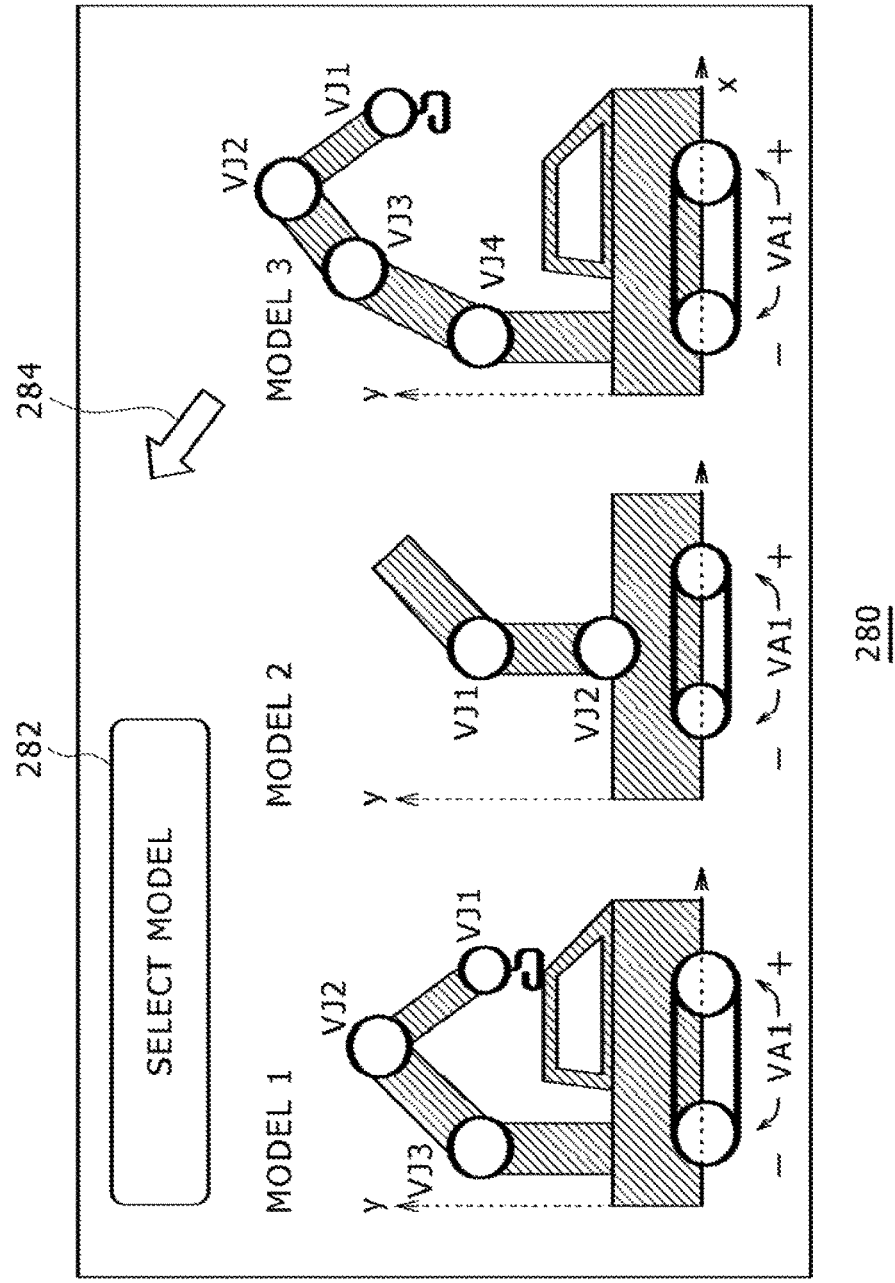
FIG. 20 is a diagram depicting an example of a screen displayed on a display device to receive a model selecting input by a user in S46 in FIG. 19.

FIG. 20 depicts an example of a screen displayed on the display device 16 to receive a model selecting input by the user in S46 in FIG. 19. A model selection receiving screen 280 includes images of a plurality of models, that is, a "model 1," a "model 2," and a "model 3," a character string 282 that prompts for a selecting input, and a cursor 284 movable by the input device 14. The "model 1," the "model 2," and the "model 3" are the candidate models extracted in S44 in FIG. 19, and are a result of filtering by at least one of the features as things, the structural features, and the external features, as described above. When the user specifies "crane truck" as a feature as a thing, for example, the extracted models are all crane trucks. In this case, a screen for receiving the selection of "crane truck" is also displayed before the display of the model selection receiving screen 280.

The extracted number is not limited to three. All of things matching the condition may be extracted. Alternatively, models are ranked by using similarity degree evaluation values described above, and a predetermined number of models ranking high may be extracted. In this case, the model selection receiving screen 280 may arrange the images of the models in decreasing order of ranking from the left. In FIG. 20, the "model 1," the "model 2," and the "model 3" are each a crane truck, but the shapes of crane parts of the models, such as the numbers of joints or the like, are different from each other. The user selects one model by indicating a desired model or a model similar to the block set by the cursor 284, and performing a determination input by the input device 14, for example.

Incidentally, means other than the means for the selecting input via the cursor 284 may be used for the selection of the model. For example, a technology is proposed which photographs the user by the camera 122, and which detects the position of a fingertip of the user and, in turn, a position indicated on the display screen from a depth image or the like. When this technology is used, and the user indicates the model to be selected, the information processing device 10 may recognize the selected model. Inputs by the user on respective setting screens depicted in FIGS. 21 and 22 may be realized in a similar manner.

Figure 21:
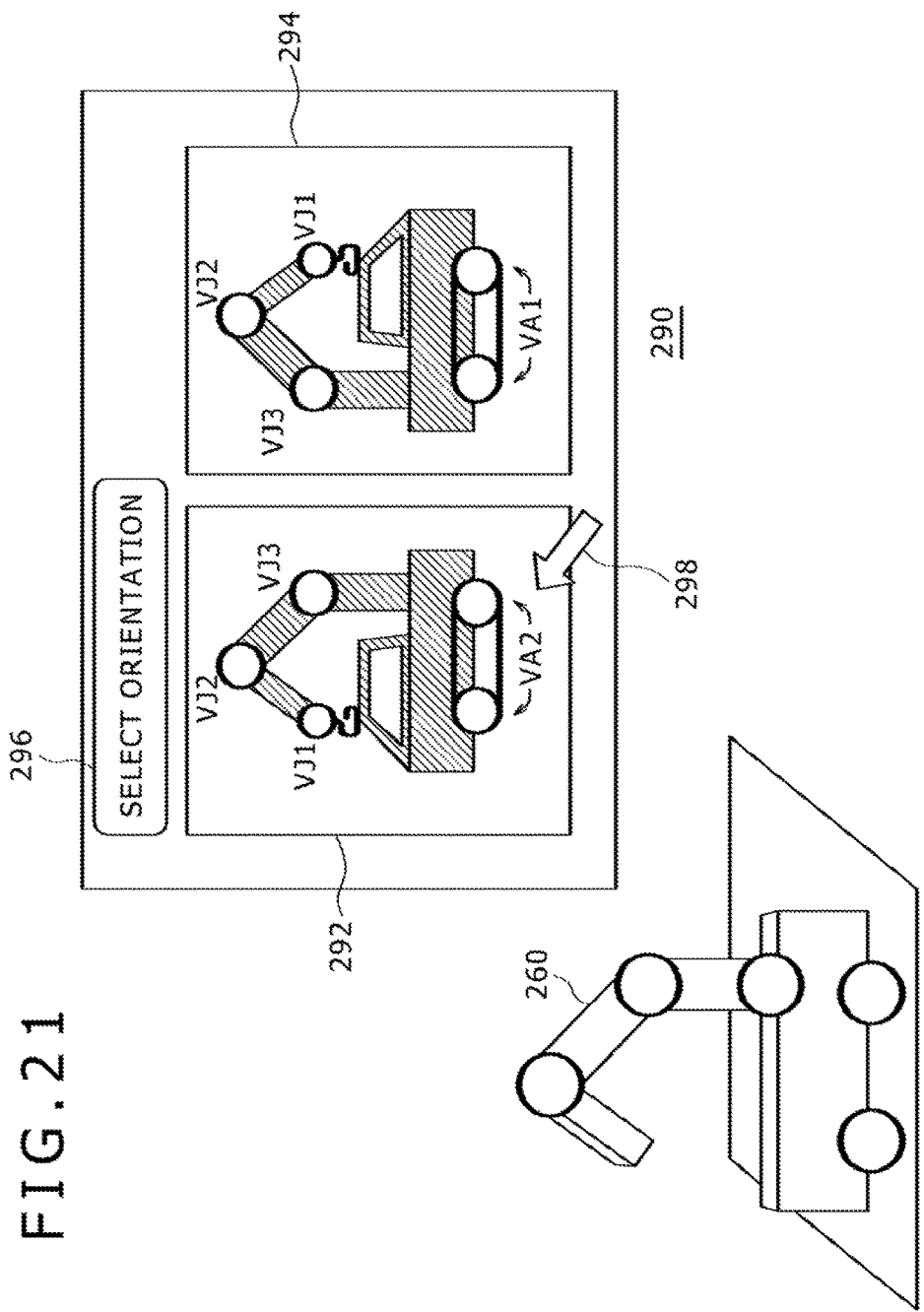
FIG. 21 is a diagram depicting an example of a screen displayed on the display device to set a coordinate system common to the block set and a selected model in S48 in FIG. 19.

FIG. 21 depicts an example of a screen displayed on the display device 16 to set the coordinate system common to the block set and the selected model in S48 in FIG. 19. In the present example, the user specifies the common coordinate system by adjusting the orientation of the 3D object on the screen according to the orientation of the block set. Consequently, as described above, the front-rear orientation of the overall structures, the positional relation of each link with respect to the joint, the definition of the joint angle, and the like can be made uniform. A model display orientation setting receiving screen 290 includes an image 292 in which the front of the crane truck is oriented to the left, an image 294 in which the front of the crane truck is oriented to the right, a character string 296 that prompts for the specification of an orientation, and a cursor 298 movable by the input device 14.

The present example assumes that the user selects the "model 1" on the model selection receiving screen 280 in FIG. 20. The images in which the object of the same model is viewed from the two left and right directions are displayed. For example, the user places the block set 260 as depicted in the figure, indicates an image depicting an orientation similar to that of the block set or depicting an orientation that the user considers to be the same as the orientation of the block set by the cursor 298, and performs a determination input by the input device 14. In the example of the figure, the left oriented image 292 is selected. Then, the information processing section 30 sets the coordinate system to the block set 260 and the 3D object such that the orientation of the block set 260 which orientation is obtained by the structure analyzing section 22 and the orientation of the 3D object in the selected image are defined as the same orientation. Incidentally, as in the present example, when the front and rear of the block set 260 and the 3D object can be estimated on the basis of a structure such as the position of the crane with respect to the platform vehicle or the like, the information processing section 30 may set the coordinate system as described above.

Figure 22:
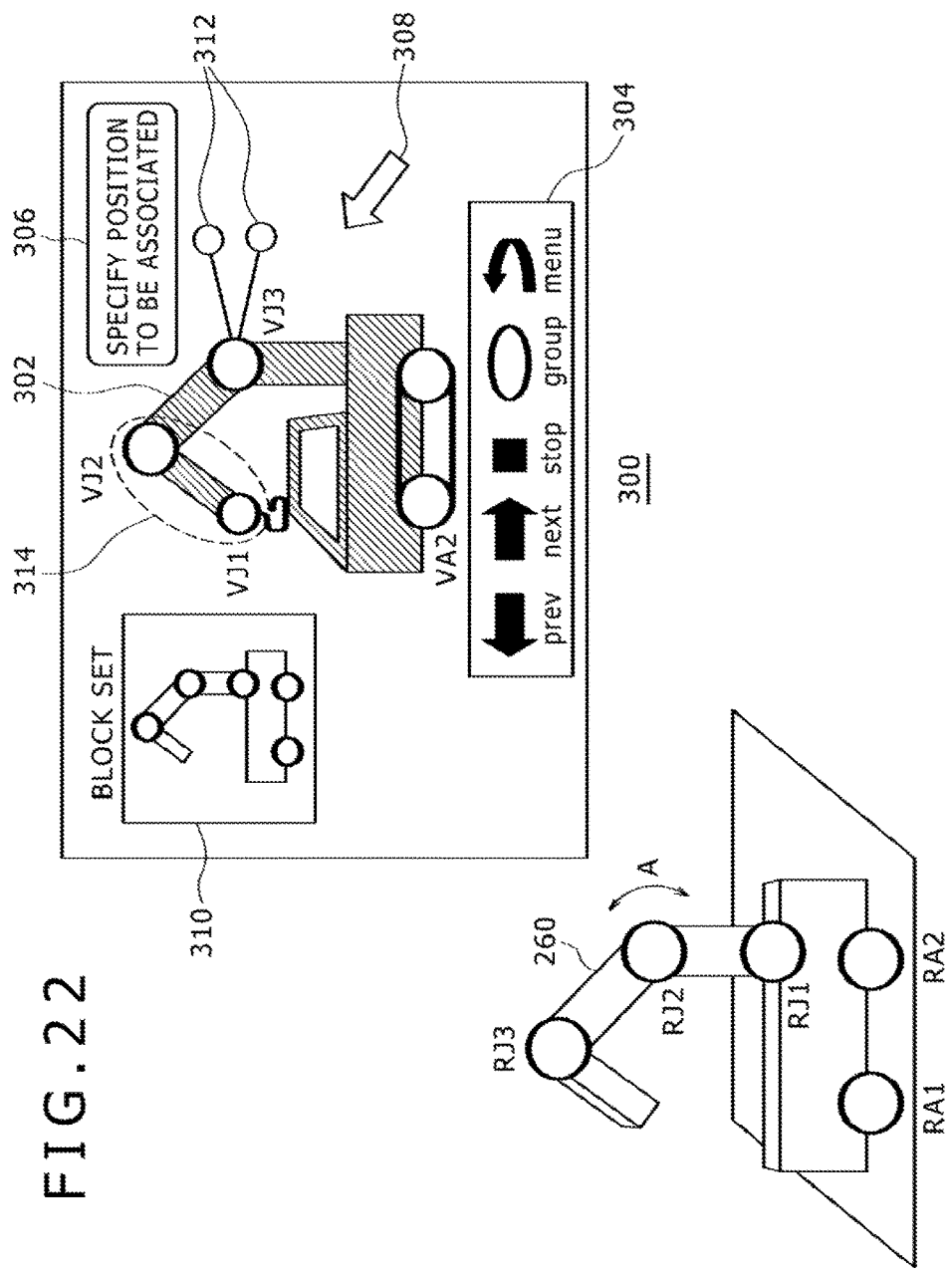
FIG. 22 is a diagram depicting the block set when the object is created by two blocks and an example of transition of a display screen at a time of registration in the present embodiment.

FIG. 22 depicts an example of a screen displayed on the display device 16 to set the corresponding positions of the block set and the 3D object in S50 in FIG. 19. A corresponding position setting screen 300 includes an image 302 of the 3D object, a command list section 304, a character string 306 that prompts for a setting input, and a cursor 308 movable by the input device 14. The 3D object on the screen is in the same orientation as the block set after going through the model display orientation setting receiving screen 290. Thus, the correspondence with the block set is easily understood by the user. The corresponding position setting screen 300 may further display an image 310 of the block set 260.

The image 310 is an image photographed by the camera 122 or an image in which the state of the block set 260 which state is recognized by the information processing device 10 is rendered as a 3D object. In the former case, when the user and the camera 122 are on opposite sides from each other with respect to the block set 260, the photographed image is flipped horizontally to reproduce the block set 260 as viewed from the user. In the latter case, when a non-communicating block makes it difficult to confirm the structure of the core, only an image of the core may be displayed.

First, the user moves a joint desired to be associated in the block set 260 by bending and stretching the joint, for example (for example an arrow A). The movement is recognized by the structure analyzing section 22. An input specifying the joint (for example RJ2) to be associated on the block set side is thereby realized. Next, the user indicates a joint (for example VJ3) to be associated on the 3D object side in the image 302 of the 3D object by the cursor 308, and performs a determination input by the input device 14. The joint RJ2 of the block set 260 and the joint VJ3 of the 3D object are thereby associated with each other. The information processing section 30 records and stores the correspondence relation of these joints in the correspondence information storage section 28.

Such a setting is made for all of joints of the block set 260 which joints the user desires to move. In addition, a similar setting may be made for wheels. The user may be allowed to check the movement of the 3D object when the block set 260 is actually moved on the basis of the thus set correspondence relation. Then, corrections may be allowed to be made as required. For this purpose, the command list section 304 displays a GUI such as a "prev" button for canceling the immediately previous setting of a corresponding position and making a setting again, a "next" button for confirming a present setting and setting a next corresponding position, a "stop" button for storing all of settings at the present time and ending the setting processing, and the like. Further, a "menu" button for making a transition to a screen displaying various kinds of setting screens as a menu is also displayed. Incidentally, movement confirmation processing may be performed after movement correspondences to be described later are set, and whether or not to cancel the settings may be confirmed accordingly by the "prev" button or the "next" button.

Incidentally, when joints of the 3D object which joints may be associated with a specified joint of the block set 260 can be automatically narrowed down from the movable angle of the joint or a structural constraint condition, the information processing section 30 may suggest the joints as candidates to the user. That is, at a point in time that a joint to be associated on the block set side is specified, joints as candidates for association in the image 302 of the 3D object displayed on the corresponding position setting screen 300 are changed in color or the like, and the user is allowed to select one of the joints. Thus, even when free correspondence settings by the user are allowed, impossible association can be avoided.

In addition, as described above, a plurality of joints of the block set are allowed to be associated with one joint of the 3D object, or one joint of the block set is allowed to be associated with a plurality of joints of the 3D object. In the example of FIG. 22, two marks 312 indicating that two joints of the block set are associated with the joint VJ3 of the 3D model are provided to the joint VJ3 of the 3D model. This is for example realized by an operation of associating the joint RJ1 of the block set 260 with the joint VJ3 of the 3D object by moving the joint RJ1 of the block set 260 and further associating the joint RJ2 with the same joint VJ3 of the 3D object by moving the joint RJ2.

On the other hand, the joints VJ1 and VJ2 of the 3D object are grouped into one group, and are enclosed by an ellipse 314 indicating that the joints VJ1 and VJ2 of the 3D object are associated with one joint of the block set. For a purpose of thus grouping the plurality of joints of the 3D object into one group, the command list section 304 also displays a GUI of a "group" button for rendering the ellipse 314 indicating the group. For example, the user moves the joint RJ3 of the block set 260. Then, the "group" button on the screen is selected by the cursor 308, and the ellipse 314 is drawn so as to enclose the joints VJ2 and VJ1 of the 3D object. The joint RJ3 of the block set 260 is thereby associated with the joints VJ2 and VJ1 of the 3D object.

The information processing section 30 may determine a few suitable grouping patterns from a viewpoint of the overall structures of the block set and the 3D object, movable angles, or the like, and display the grouping patterns as candidates on the corresponding position setting screen 300. In this case, the user determines grouping by selecting one pattern from the candidates. Alternatively, grouping pattern candidates may be created as metadata of the 3D object, and displayed on the corresponding position setting screen 300 so that the user makes a selection. Incidentally, when the image 310 of the block set is displayed on the corresponding position setting screen 300, the joint of the block set may be specified on the image 310 by the cursor 308. In addition, the associated joints may be displayed in a same color in the image 302 of the 3D object and the image 310 of the block set, or correspondence relation thereof may be clearly indicated by connecting the associated joints to each other by a line.

Figure 23:
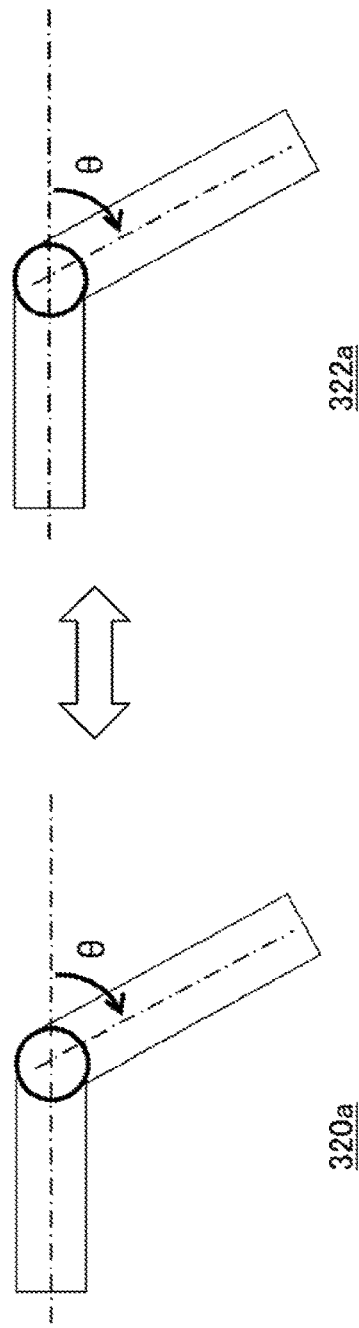
FIG. 23 is a diagram illustrating a case where joints associated with each other on a one-to-one basis move by a same angle in the present embodiment.

The movement correspondences of the thus associated joints will next be described. The correspondences are set by the information processing section 30, the user, or cooperation of both of the information processing section 30 and the user in S52 in FIG. 19. FIG. 23 depicts, as a basic mode, a case where joints of the block set and the 3D object are associated with each other on a one-to-one basis, and the joints move to a same angle. The left of FIG. 23 depicts a joint part 320a of the block set, and the right of FIG. 23 depicts a corresponding joint part 322a of the 3D object. That is, when the joint part 320a of the block set is bent by an angle θ from a state in which the joint is not bent, the corresponding joint part 322a of the 3D object is also bent by the angle θ. Depending on the processing performed by the information processing section 30, when the joint part 322a of the 3D object is bent by the angle θ, the corresponding joint 322a may be bent by the angle θ by driving an actuator, which is the driving section 148 of the block set, or the like via the driving control section 34.

Figure 24:
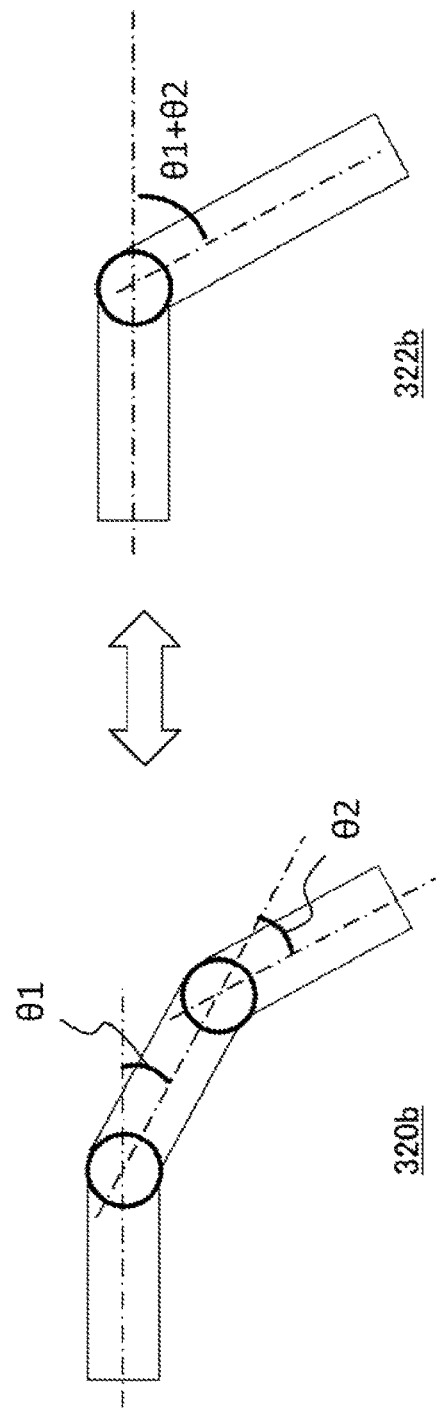
FIG. 24 is a diagram depicting an example of correspondence between angles of respective joints in a case where two grouped joints are associated with one joint in the present embodiment.

On the basis of such a mode, various settings are realized according to a constraint condition, such as movable angles, the number of joints to be associated, or the like, an intention of the user, or the like. FIG. 24 depicts an example of correspondence between angles of respective joints in a case where two grouped joints are associated with one joint. The left of FIG. 24 depicts joint parts 320b of the block set, and the right of FIG. 24 depicts a corresponding joint part 322b of the 3D object. In the present example, the two joint parts 320b of the block set are associated with one joint part 322b of the 3D object. Then, when one of the joints of the block set is bent by an angle θ1, and the other joint is bent by an angle θ2, the corresponding joint part 322b of the 3D object is bent by an angle (θ1+θ2), which is a sum of the angle θ1 and the angle θ2. That is, the changes in the joint angles by the two joints of the block set are realized by the one joint of the 3D object.

This mode is effective when the movable angle of each joint of the block set is smaller than a change in the joint angle which change is required of the corresponding joint of the 3D object. Changes in three or more joint angles of the block set may be summed. Angle correspondence relation is similar also in a case where a plurality of joints of the 3D object are grouped and associated with one joint of the block set. This mode is effective when the number of joints of the block set is smaller than the number of joints of the 3D object.

In addition, conversely, when the joint part 322b of the 3D object is bent by the angle (θ1+θ2), the two corresponding joint parts 320b of the block set may be bent by the respective angles θ1 and θ2. In this case, the information processing section 30 can determine a ratio between the angles θ1 and θ2 according to a constraint condition such as the movable angles of the respective joints, actual movement of the thing that the block set is assumed to represent, that is, the thing represented by the 3D object, or the like. When the movable angles of the two joints of the block set are in a ratio of 1:2, for example, the angles θ1 and θ2 are also set in the ratio of 1:2.

The same is true for a case where a change in angle of one joint of the block set is allocated to the angles of a plurality of joints of the 3D object. When the crane truck depicted in FIG. 22 is assumed, for example, it is natural that a hook connected to the joint VJ1 of the 3D object is oriented vertically downward at all times. Hence, the information processing section 30 calculates the angles θ1 and θ2 so as to maintain such a state. Such an allocation rule is created together with the data of the 3D object. Incidentally, when the mode in which a sum of changes in angles of one of the block set and the 3D object is reflected in a change in angle of the other and the mode in which a change in angle of one of the block set and the 3D object is reflected so as to be allocated to changes in a plurality of angles of the other are combined with each other, a plurality of joints of the block set can also be associated with a plurality of joints of the 3D object.

Figure 25:
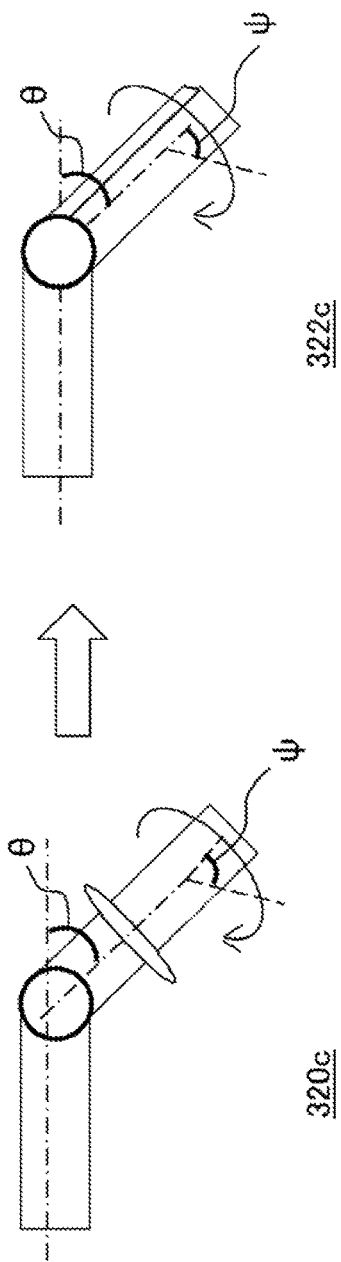
FIG. 25 is a diagram depicting another example of correspondence between angles of respective joints in a case where two joints are grouped and associated with one joint in the present embodiment.

FIG. 25 depicts another example of correspondence between angles of respective joints in a case where two joints are grouped and associated with one joint. The left of FIG. 25 depicts joint parts 320c of the block set, and the right of FIG. 25 depicts a corresponding joint part 322c of the 3D object. Suppose in the present example that the two joints of the block set have axes of rotation different from each other, that one of the two joints changes in angle about an axis perpendicular to the plane of the figure, and that the other of the two joints changes in angle about the axis of a link. On the other hand, suppose that one joint of the 3D object which joint is associated with the two joints of the block set is a joint having two degrees of freedom that enable angles to be changed about two axes corresponding to the axes of the block set.

Then, when one joint of the joint parts 320c of the block set is changed by an angle θ, and the other joint is changed by an angle ψ, the corresponding joint part 322c of the 3D object is changed by the angles θ and ψ about the respective axes. In addition, conversely, when the joint part 322c of the 3D object is changed by the angles θ and ψ about the respective axes, the two corresponding joints of the block set 320c may be changed by θ and ψ, respectively.

Figure 26:
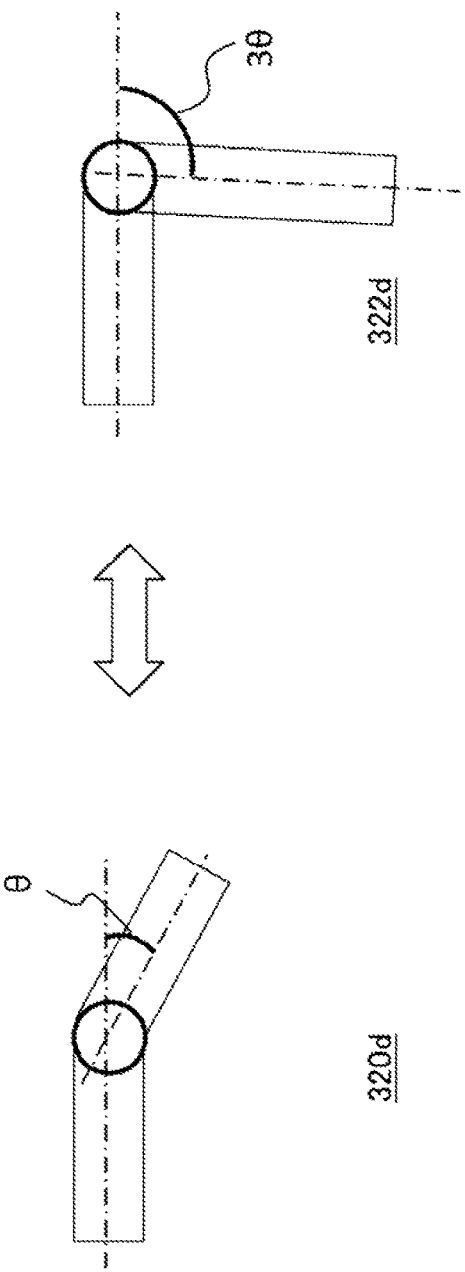
FIG. 26 is a diagram illustrating a case where changes in angles of joints associated with each other on a one-to-one basis are made different in the present embodiment.

FIG. 26 illustrates a case where changes in angles of joints associated with each other on a one-to-one basis are made different from each other. The left of FIG. 26 depicts a joint part 320d of the block set, and the right of FIG. 26 depicts a corresponding joint part 322d of the 3D object. In the present example, when the joint of the block set is changed by an angle θ, the corresponding joint of the 3D object is changed by an angle 3 θ, which is three times the angle θ. When the movable angle of the joint of the block set is smaller than a change in angle which change is required of the corresponding joint of the 3D object, for example, the 3D object may not move as expected even when the block set is moved to a limit. There is also a case where the 3D object is desired to be moved dynamically without much effort of moving the block set.

Such a problem can be solved by changing the joint angle of the 3D object by an angle obtained by multiplying a change in angle of the joint of the block set by a predetermined value larger than one as depicted in the figure. Alternatively, the joint angle of the 3D object may be changed by an angle smaller than that of the block set by multiplying the change in angle of the block set by a predetermined value smaller than one. This mode is effective for example when the 3D object is desired to move minutely with higher precision than the movement of a hand moving the block set as in operation of a manipulator, for example. It suffices to make a similar setting also in a case where a change in angle of the joint of the 3D object is reflected in a change in the angle of the block set. Incidentally, the mode in which a change in angle of one of the joints is multiplied by a predetermined value to obtain a change in angle of the other can be combined with the modes depicted in FIG. 24 and FIG. 25. In this case, a same value may be multiplied for all of the grouped joints, or values different according to the joints may be multiplied.

Figure 27:
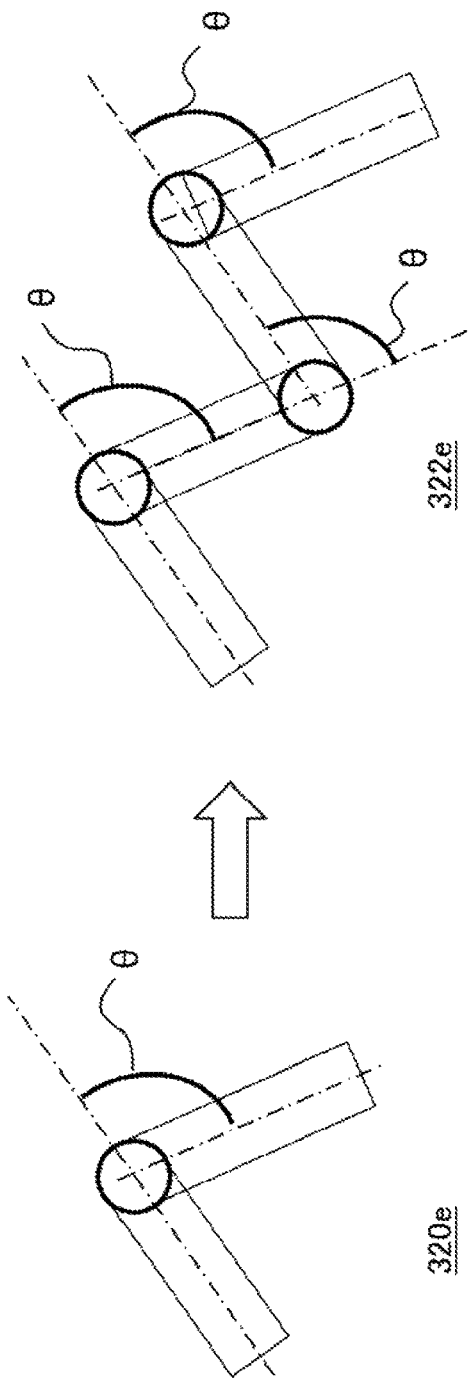
FIG. 27 is a diagram depicting an example in which one joint of a block set is associated with a plurality of joints of a 3D object in the present embodiment.

FIG. 27 depicts another example of associating one joint of the block set with a plurality of joints of the 3D object. The left of FIG. 27 depicts a joint part 320e of the block set. The right of FIG. 27 depicts corresponding joint parts 322e of the 3D object. In the present example, one joint part 320e of the block set is associated with three joint parts 322e of the 3D object. Then, when the joint of the block set is bent by an angle θ, the three corresponding joints of the 3D object are each bent by the same angle θ.

Thus, even in a case of a block set having a simple configuration, the movement of the block set can be reflected in a wide area of the 3D object. For example, when one joint of the block set is associated with all of joints of a large snake having a shape formed by further connecting a plurality of joint parts 322e of the 3D object, a movement such as an advancing movement of the large snake can be expressed even by the block set constituted of only the joint part 320e in FIG. 27. As described earlier, when moving images in which the large snake is made to move in various manners are stored, the large snake can be used as a character in a game or an animation in later arbitrary timing. Such an advanced image expression can be realized by such a simple block set as has the joint part 320e. Incidentally, the joints associated in the 3D object in this mode are not limited to adjacent relation to each other as depicted in the figure, but may be a plurality of joints present at distant positions of the 3D object.

Figures 28, 29:
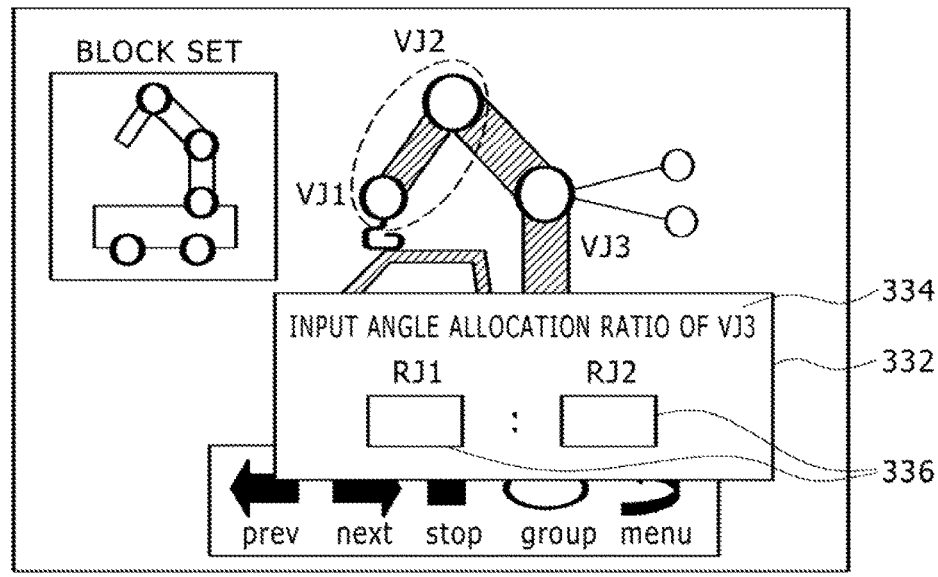
FIG. 28 is a diagram depicting an example of a screen displayed on the display device to set correspondence between the movements of the block set and the 3D object in S52 in FIG. 19.
FIG. 29 is a diagram depicting an example of a data structure of information on corresponding positions of the block set and the 3D object and correspondences between movements of the respective corresponding positions in the present embodiment.

FIG. 28 depicts an example of a screen displayed on the display device 16 to set a movement correspondence between the block set and the 3D object in S52 in FIG. 19. A movement correspondence setting screen 330 is a screen obtained by making overlay display of a dialog box 332 for inputting a movement correspondence on the corresponding position setting screen 300 depicted in FIG. 22 each time the user sets a corresponding position on the screen. The present example assumes that after the joints RJ1 and RJ2 of the block set are grouped and associated with the joint VJ3 of the 3D object, an allocation ratio when a change in the angle of VJ3 is allocated to changes in the angles of RJ1 and RJ2 of the block set is set. For this purpose, the dialog box 332 displays a character string 334 that prompts for inputting the ratio and a text box 336 for inputting each numerical value of the ratio.

When the user inputs concrete numerical values to the text box via the input device 14 or the like, the information processing section 30 further associates the ratio with the association of the joints RJ1 and RJ2 of the block set with the joint VJ3 of the 3D object, and stores in the correspondence information storage section 28. The information set in the dialog box 332 is not limited to this. Necessary information among associations as in FIGS. 23 to 27 is allowed to be set sequentially according to whether or not joints are grouped. However, as described above, when the information processing section 30 can associate movements by a rule set in advance, setting by the user can be omitted. Alternatively, the user may be allowed to correct an association performed by the information processing section 30 in a similar dialog box.

FIG. 29 depicts an example of a data structure of information on corresponding positions of the block set and the 3D object and correspondences between movements of the respective corresponding positions, the information being stored in the correspondence information storage section 28. A correspondence information table 340 includes a block set information section 342 depicting corresponding positions and movements on the block set side and a 3D object information section 344 depicting corresponding positions and movements on the 3D object side, the corresponding positions and the movements on the 3D object side corresponding to the positions and the movements of the block set, the positions and the movements of the block set being entered in the section. In the present example, joints of the block set are associated with joints of the 3D object, and further correspondences between changes in angles of these joints are set.

The correspondences are basically entered in row units. Respective "joint" sections of the block set information section 342 and the 3D object information section 344, for example, show that the joints RJ1 and RJ2 of the block set are associated with the joint VJ3 of the 3D object. When the movement of the block set is reflected in the 3D object in this correspondence, a sum of changes in angles of the joints RJ1 and RJ is defined as representing a change in angle of the joint VJ3 of the 3D object.

Respective "angle change" sections of the block set information section 342 and the 3D object information section 344 show that when the movement of the 3D object is conversely reflected in the block set, and the angle of the joint VJ3 of the 3D object is changed by θ, the angles of the joints RJ1 and RJ2 are each changed by θ/2, that is, the allocation ratio is 1:1. The joint RJ3 of the block set is associated with the joints VJ2 and VJ1 of the 3D object, and when the movement of the block set is reflected in the 3D object, the angle change allocation ratio is 1:2. In the following section, the correspondences between the either movements described with reference to FIGS. 23 to 27 are similarly entered together with the corresponding positions.

The description thus far has been made mainly of concrete examples related to correspondences between the movements of joints. Description will next be made of association of movements of wheels. In the case of joints, although both of the block set and the 3D object have constraint conditions such as movable angles, overall structures, and the like, joints are basically independent of each other, and therefore the joints of the block set and the joints of the 3D object can be associated equally. On the other hand, in the case of wheels, there are differences in nature in that the block set have more constraint conditions than in the case of joints, while the 3D object can be expressed as if the 3D object were running even when the movement of the wheels is not defined precisely. That is, in order to make the block set and the 3D object appear to be interlocked with each other, it suffices to associate traveling directions and approximate speeds with each other. Such correspondence relations are obtained by setting the common coordinate system in S48 in FIG. 19.

When the user moves the block set 260, and the movement is reflected in the 3D object, the reflection of the movement of the block set in the 3D object can be realized easily on the basis of only such correspondence relations. Specifically, it suffices to obtain an amount of movement and a traveling direction of the block set from a photographed image of the camera 122 or the like, and express the 3D object such that the 3D object is also moving similarly on the basis of the amount of movement and the traveling direction of the block set. When the movement of the 3D object is to be reflected in the block set, on the other hand, settings according to constraint conditions are necessary. For example, a vehicle cannot be made to run when the wheels are not performing cooperative operation. In addition, a rotational speed of the wheels for obtaining a desirable speed changes according to the diameter of the wheels. Thus, when an appropriate adjustment is not made, the vehicle may reach too high a speed, and collide with a wall, for example.

Thus, in associating the movement of the wheels, there is less room for free setting by the user than in the case of joints because there are more constraint conditions on the block set side. Hence, mainly the information processing section 30 associates movements. Specifically, at a point in time that the front and rear and the left and right of the block set become clear, driving wheels, driven wheels, and steered wheels are determined according to a driving system set in advance. Further, grouping is performed so as to satisfy a constraint condition that the left and right driving wheels and the left and right steered wheels have a same rotational speed and a same steering angle. In addition, the rotational speed and steering angle of the wheels of the block set are associated with the virtual speed and change of direction of the 3D object so that the block set runs with a suitable speed and a suitable change of direction corresponding to the speed and change of direction of the 3D object expressed in the virtual world.

Figure 30:
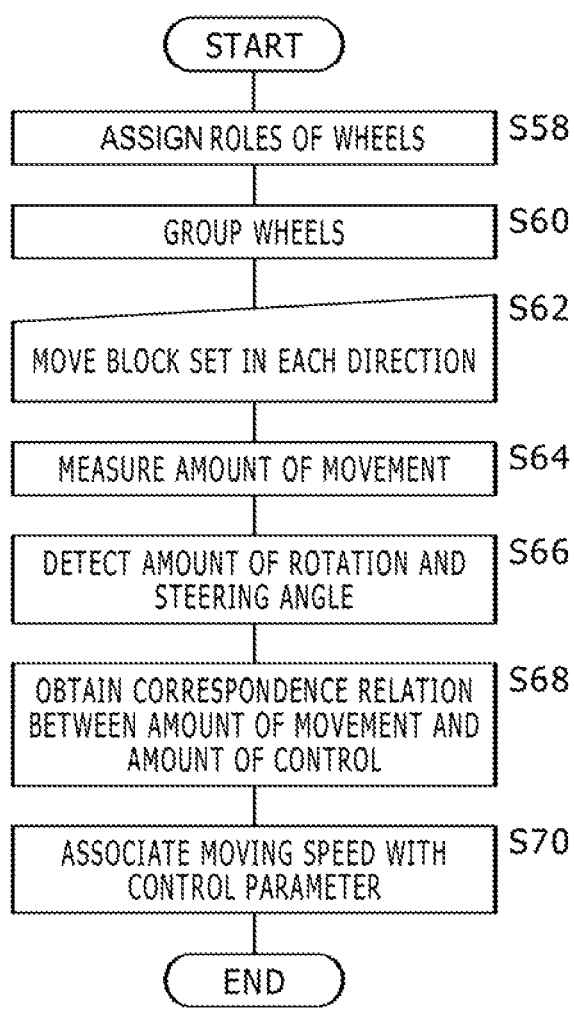
FIG. 30 is a flowchart depicting a processing procedure for setting correspondence between the movements of the 3D object and the block set in the present embodiment.

FIG. 30 is a flowchart depicting a processing procedure for setting correspondences between the movements of the 3D object and the block set in the mode in which the movement of the 3D object is reflected in the block set. This processing corresponds to the processing of S50 and S52 in FIG. 19. When the information processing section 30 first detects that wheels are fitted to the block set on the basis of information from the structure analyzing section 22, the information processing section 30 assigns a role of wheels such as driving wheels, steered wheels, or the like to the front wheels or the rear wheels according to the front-rear and left-right orientation and driving system of the block set (S58). Further, at least two wheels arranged in parallel with each other which wheels are assigned the role of the driving wheels or the steered wheels are grouped into one group, and are thereby made to perform cooperative operation (S60).

Incidentally, when the two wheels arranged in parallel with each other rotate about one axle, the two wheels naturally perform cooperative operation, and therefore the processing of S60 can be omitted. Next, control parameters for obtaining a suitable moving speed and a suitable change of direction that reflect virtual running of the 3D object are obtained. The control parameters in this case are the rotational speed of an actuator that rotates the axle of the driving wheels, an amount of movement of an actuator that changes the steering angle of the steered wheels, and the like. Incidentally, the plurality of actuators that control the driving wheels and the steered wheels grouped in S60 are controlled so as to perform an identical operation according to control signals from the information processing device 10.

In order to obtain the control parameters, first, the user is made to actually move the block set in a predetermined direction. An amount of movement of the block set is measured, and an amount of rotation of the axle and a steering angle at the time of the movement are measured (S62, S64, and S66). The user may drive the block set electronically by a control mechanism prepared separately, or may move the block set manually by pushing the body of the block set by hand, for example. In the latter case, the axle and a mechanism for changing the steering angle are released from control of the actuators. The amount of movement of the block set can be obtained from the photographed image of the camera 122 or a depth image generated from the photographed image of the camera 122.

The amount of rotation can be obtained from a signal from a rotary encoder provided to a wheel. The steering angle can be obtained by a steering angle sensor provided to a wheel. Incidentally, when the sensors such as the rotary encoder and the like are not provided, for example, the amount of rotation and the steering angle may be calculated on the basis of the diameter of the wheels, a traveling distance, and a traveling direction.

Then, on the basis of the actual amount of rotation and the actual steering angle for the amount of movement including a change of direction, amounts of control such as an amount of rotation of a motor, an amount of movement of an actuator, and the like for obtaining the amount of movement are obtained (S68). This correspondence relation is converted into a value per unit time or per unit angle. A moving speed and a unit steering angle are thereby associated with the values of the control parameters (S70). The moving speed in this case is a suitable moving speed of the block set itself. However, when the block set is interlocked with the 3D object on the screen, the moving speed is a value determined by a moving speed in the virtual world. The same is true for the steering angle. Hence, the movement of the 3D object is associated with the movement of the block set by the processing of S70.

Incidentally, when the diameter of the wheels connected to the block set is known from the identification number of the wheels, correspondence relation between the moving speed and the control parameter can be obtained by operation. Thus, the processing of S62 to S68 may be omitted. In addition, the example described thus far assumes that the block set assumed to represent a crane truck and the 3D object of the crane truck are associated with each other. Description has therefore been made of association of movements of wheels. However, the flowchart depicted in FIG. 28 is similarly applied even when the 3D object does not have wheels.

That is, even in a case where the 3D object is a human, an animal, an insect, a vehicle other than a car, or the like, when movement in the virtual world is reflected in the movement of the block set, the block set can be moved at a speed and in a direction which speed and direction correspond to the virtual movement of the 3D object, by associating the moving speed and the steering angle with the control parameters by the processing procedure of FIG. 28. Further, it is applicable to not only the mode in which the movement of the 3D object is reflected but also a mode in which the block set is simply moved according to a result of processing performed by the information processing device 10.

FIG. 31 is a diagram of assistance in explaining a case where the above-described settings related to the wheels of the block set are extended to a composite link. In a composite link 350 depicted in the figure, joints are not completely independent of each other, but links are interlocked with each other. That is, when one joint of the composite link 350 is moved as indicated by an arrow, the four joints are all moved (composite link 352). In such a case, it is not possible to move only one joint by an actuator. Thus, as in the case of driving wheels, the four joints are grouped, and made to perform cooperative operation. When the composite link is incorporated into the block set, the user clearly indicates the presence of the composite link on a correspondence setting screen or the like, or the information processing section 30 recognizes the presence of the composite link when the composite link in the real thing of the block set is moved. Then, when a movement correspondence with the 3D object is set, all of the joints included in the composite link are grouped.

According to the present embodiment described above, blocks that can be assembled freely are used as an input device or an output device for processing in the information processing device. Details such as the skeletons and positions of the blocks after assembly or the like are obtained by using various kinds of sensors for obtaining a position and a posture and communicating blocks having a communicating function. Further, the surface shape of blocks after the assembly is obtained by using means for detecting the presence of the blocks in the real space, such as an image photographed by the camera or the like. The position, posture, and shape of the blocks after the assembly can be identified with high accuracy by integrating these pieces of information even when a non-communicating block without a communicating function is used as a part of the blocks.

As a result, the shape, material, color, and the like of the blocks are not limited, even things made by the user himself/herself can be used, and an object having an external appearance serving a purpose of the user can be created freely. In addition, the information processing device can obtain the position, the posture, and the shape with high accuracy irrespective of the external appearance. Thus, various kinds of information processing can be performed with an assembling or moving action by the user as input information. In addition, the assembled blocks can be moved as a result of information processing.

For example, a 3D object having a same external appearance as the assembled blocks can be displayed, or a 3D object having a more realistic external appearance which 3D object corresponds to the assembled blocks can be displayed. In the latter case, the user may form the 3D object itself by specifying a part of the 3D object for each part of the blocks, or the whole of the blocks may be made to correspond to one 3D object. At this time, by associating positions of joints to be interlocked or the like, it is possible to mutually reflect not only a change in position but also a change in posture or shape. The setting corresponding positions and movement associations can be set on the basis of constraint conditions such as the shapes of the block set and the 3D object, the number of joints, the movable angles of the joints, the cooperative operation of wheels, and the like. Such associations are established by the information processing device automatically, or an environment allowing the user to make the settings is provided. It is thereby possible to form a link between the real world and the virtual world freely while reducing a load on the user.

The present invention has been described above on the basis of embodiments thereof. The foregoing embodiments are illustrative, and it is to be understood by those skilled in the art that combinations of constituent elements and processing processes of the embodiments are susceptible of various modifications and that such modifications also fall within the scope of the present invention.

For example, the corresponding position setting screen 300 described with reference to FIG. 22 assumes the block set as an object to be associated with the 3D object on the screen. However, a thing other than the block set, such for example as the user himself/herself or the like, can be associated similarly. When the user is associated, the camera 122 photographs the user, a depth image is generated on the basis of the photographed image, for example, and the position of the skeleton is estimated. The position of the skeleton can be tracked by applying a conventional technology such as skeleton tracking or the like. When the user then moves a part such as an arm or the like about a joint desired to be associated such as a shoulder, an elbow, or the like, the information processing device 10 recognizes the joint as in the case of the block set. Further, a joint of the 3D object is specified on the screen, whereby the joints of the user and the 3D object can be associated with each other.

A mode can be thereby realized in which the 3D object moves according to the movement of the user. Alternatively, when the block set is assembled into the form of a human, and is associated with the 3D object as in the present embodiment, the joint of the user and the joint of the block set are indirectly associated with each other via the joint of the 3D object. When this state is utilized, and is combined with the mode in which the movement of the 3D object is reflected in the block set in the present embodiment, a mode in which the block set is moved according to the movement of the user can also be realized.

As a modification of this mode, an image of the user and an image depicting positions of the skeleton may be generated in real time from the photographed image, and displayed on a corresponding position setting screen, so that joints of the user and joints of the 3D object are associated with each other on the screen. At this time, both of the images may be displayed simultaneously, or displayed alternately to receive specifications of joints whose correspondences are to be set one by one. Incidentally, these modifications assume that the user associates the joints of the user himself/herself with the joints of the 3D object. However, when the 3D object is a human, a robot, or the like, and correspondences with the joints of the user are obvious, the settings by the user may be omitted, and the information processing device may make all of the settings.

In addition, in the present embodiment, the wheels are fitted to the axle in a state in which the front and rear of the vehicle are known, and the information processing device accordingly determines the roles of driving wheels, driven wheels, and steered wheels. Then, the movement of actuators that control the operation of the vehicle is changed according to the roles. This mode may be extended to realize a block including an actuator that changes movement thereof according to a thing connected thereto. For example, when a part constituted of an axle and a wheel is fitted, the vehicle of the block set is moved by rotating the axle. When a part constituted of a cam and a spring or the like is fitted, the spring is released by rotation of the cam, and an arrow in a set state or the like is shot. When a part including a joint as described above is fitted, the part is made to operate as a joint.

In this case, the information processing device 10 changes the movement of the actuator appropriately by recognizing the kind of the connected thing from a photographed image, and transmitting a control signal corresponding to the kind of the connected thing to the block set. Thus, the versatility of blocks including actuators is increased, and a wide variety of block sets can be realized at lower cost than preparing different blocks for different kinds.

REFERENCE SIGNS LIST

2 Information processing system, 10 Information processing device, 14 Input device, 16 Display device, 20 Core information receiving section, 22 Structure analyzing section, 24 Block information storage section, 26 Model data storage section, 28 Correspondence information storage section, 30 Information processing section, 32 Display processing section, 34 Driving control section, 102a Quadrangular prism block, 122 Camera, 120 Block set, 126a Block, 128a Battery, 130a Communicating mechanism, 132a Memory, 134 Position sensor, 136a Motion sensor, 138 Angle sensor, 139a Actuator, 141 Rotary encoder, 142a First block, 143a First communicating section, 144a Element information obtaining section, 146a Second communicating section, 148 Driving section.

INDUSTRIAL APPLICABILITY

As described above, the present invention is applicable to toys, game devices, assembled devices, learning materials, content display terminals, information processing devices, robots, and the like.

The invention claimed is:

1. An information processing device comprising:
a structural information obtaining section obtaining, from an assembled external object formed by coupling blocks prepared individually to each other, information related to respective positions and amounts of movement of a plurality of movable parts in an overall structure of the assembled external object; and
an information processing section displaying, on a display device, a setting screen for receiving a setting input related to an interlocking rule for the plurality of movable parts from a user in order to interlock the assembled external object with an object model associated with the assembled external object, generating information related to the interlocking rule on a basis of the received setting input, and storing the information related to the interlocking rule in a storage device,
wherein the information provides operational details for the information processing section to interlock the assembled external object and the object model with each other by reflecting, on a basis of information on correspondence between the plurality of movable parts of the assembled external object and another plurality of movable parts of the object model, changes in the other plurality of movable parts of the object model in response to changes in the plurality of movable parts of the assembled external object,
wherein a first subset containing a first number of the plurality of movable parts of the assembled external object may be grouped and set to be in correspondence with a second subset containing a second number of the other plurality of movable parts of the object model, and
the first and second numbers are selectable from among the following relationships: (i) first and second numbers are the same; (ii) the first and second numbers are different from one another; (iii) first number is larger than the second number; and (iv) the second number is larger than the first number.

2. The information processing device according to claim 1, wherein
the structural information obtaining section obtains information related to a position of a part moved by the user among the plurality of movable parts of the assembled external object, and
the information processing section obtains the part moved by the user and a part of the object model displayed on the setting screen, the part of the object model being specified by the user via an input device, as movable parts to be associated with each other, and generates the correspondence information by associating the movable parts with each other.

3. The information processing device according to claim 1, wherein the information processing section assists in the setting input by the user by showing the plurality of movable parts capable of being associated on the setting screen according to constraint conditions individually given to the movable parts of the assembled external object and the object model.

4. The information processing device according to claim 1, wherein the information processing section displays, together with an image of the object model, an image of the assembled external object on the setting screen on a basis of the information related to the positions of the plurality of movable parts in the overall structure of the assembled external object, obtains the plurality of movable parts in the image of the assembled external object and the plurality of movable parts in the image of the object model as movable parts to be associated with each other, the plurality of movable parts in the image of the assembled external object and the plurality of movable parts in the image of the object model being specified by the user via an input device, and generates the correspondence information by associating the plurality of movable parts with each other.

5. The information processing device according to claim 1, wherein the information processing section further displays, on the display device, an object model selecting screen displaying images of a plurality of object models as candidates to be made to correspond to the assembled external object, and receives an input for selecting one object model to be made to correspond to the object from the user.

6. The information processing device according to claim 5, wherein the information processing section extracts an object model to be displayed as a candidate from a plurality of object models prepared in advance by comparing information related to the plurality of movable parts of the assembled external object with information related to the plurality of movable parts of the plurality of object models and evaluating degrees of similarity.

7. The information processing device according to claim 1, wherein the information processing section allows the user to confirm a result of the association by moving one or more of the plurality of movable parts on a side of the object model according to movement of associated one or more of the plurality of movable parts on a side of the assembled external object after the setting input, and cancels the immediately previous association when the user performs an input for performing the association again.

8. An information processing method performed by an information processing device, the information processing method comprising:
  obtaining, from an assembled external object formed by coupling blocks prepared individually to each other, information related to respective positions and amounts of movement of a plurality of movable parts in an overall structure of the assembled external object;
  displaying, on a display device, a setting screen for receiving a setting input related to an interlocking rule for the plurality of movable parts from a user in order to interlock the assembled external object with an object model associated with the assembled external object, generating information related to the interlocking rule on a basis of the received setting input, and storing the information related to the interlocking rule in a storage device,
  wherein the information provides operational details for the information processing section to interlock the assembled external object and the object model with each other by reflecting, on a basis of information on correspondence between the plurality of movable parts of the assembled external object and another plurality of movable parts of the object model, changes in the other plurality of movable parts of the object model in response to changes in the plurality of movable parts of the assembled external object,
  wherein a first subset containing a first number of the plurality of movable parts of the assembled external object may be grouped and set to be in correspondence with a second subset containing a second number of the other plurality of movable parts of the object model, and
  the first and second numbers are selectable from among the following relationships: (i) first and second numbers are the same; (ii) the first and second numbers are different from one another; (iii) first number is larger than the second number; and (iv) the second number is larger than the first number.

9. A non-transitory, computer readable storage medium containing a computer program, which when executed by a computer, causes the computer to implement elements, comprising:
  obtaining, from an assembled external object formed by coupling blocks prepared individually to each other, information related to respective positions and amounts of movement of a plurality of movable parts in an overall structure of the assembled external object;
  displaying, on a display device, a setting screen for receiving a setting input related to an interlocking rule for the plurality of movable parts from a user in order to interlock the assembled external object with an object model associated with the assembled external object, generating information related to the interlocking rule on a basis of the received setting input, and storing the information related to the interlocking rule in a storage device,
  wherein the information provides operational details for the information processing section to interlock the assembled external object and the object model with each other by reflecting, on a basis of information on correspondence between the plurality of movable parts of the assembled external object and another plurality of movable parts of the object model, changes in the other plurality of movable parts of the object model in response to changes in the plurality of movable parts of the assembled external object,
  wherein a first subset containing a first number of the plurality of movable parts of the assembled external object may be grouped and set to be in correspondence with a second subset containing a second number of the other plurality of movable parts of the object model, and
  the first and second numbers are selectable from among the following relationships: (i) first and second numbers are the same; (ii) the first and second numbers are different from one another; (iii) first number is larger than the second number; and (iv) the second number is larger than the first number.

* * * * *